United States Patent [19]

Suzuki et al.

[11] Patent Number: 4,867,136
[45] Date of Patent: Sep. 19, 1989

[54] ENDOSCOPE APPARATUS

[75] Inventors: Akira Suzuki, Hachioji; Susumu Takahashi, Kunitachi; Takeaki Nakamura; Tatsuya Yamaguchi, both of Hino; Takashi Tsukaya, Hachioji; Tsutomu Yamamoto, Hachioji; Masanao Murata, Hachioji; Kazunari Kobayashi, Hachioji; Yoshikazu Tojo, Hachioji; Kenichi Kikuchi, Hachioji; Koji Kanbara, Hachioji; Yoshihito Shimizu, Sagamihara; Akira Hasegawa, Hachioji; Shinichiro Hattori, Akishima; Iwao Kanamori, Hachioji; Akira Yokota, Sagamihara; Kimihiko Nishioka, Hachioji; Minoru Okabe, Musashino; Katsuyuki Kanehira, Hachioji; Nobuo Yamashita, Hachioji; Masayoshi Naito, Hachioji; Tomoaki Sato, Higashiyamato; Koichi Matsui, Tokyo; Kenji Hirooka; Hiroki Hibino, both of Hachioji, all of Japan

[73] Assignee: Olympus Optical Co., Ltd., Tokyo, Japan

[21] Appl. No.: 183,223

[22] Filed: Apr. 19, 1988

[30] Foreign Application Priority Data

| Apr. 23, 1987 | [JP] | Japan | 62-98497 |
| May 20, 1987 | [JP] | Japan | 62-121019 |
| Jun. 1, 1987 | [JP] | Japan | 62-134956 |
| Jun. 1, 1987 | [JP] | Japan | 62-134957 |
| Jun. 1, 1987 | [JP] | Japan | 62-134958 |
| Jul. 8, 1987 | [JP] | Japan | 62-168790 |
| Jul. 9, 1987 | [JP] | Japan | 62-169781 |
| Jul. 17, 1987 | [JP] | Japan | 62-177304 |
| Jul. 17, 1987 | [JP] | Japan | 62-109117[U] |
| Jul. 29, 1987 | [JP] | Japan | 62-115936[U] |
| Jul. 29, 1987 | [JP] | Japan | 62-187838 |
| Jul. 29, 1987 | [JP] | Japan | 62-187840 |
| Aug. 18, 1987 | [JP] | Japan | 62-124735[U] |
| Aug. 31, 1987 | [JP] | Japan | 62-215130 |
| Sep. 3, 1987 | [JP] | Japan | 62-219259 |
| Oct. 27, 1987 | [JP] | Japan | 62-269169 |
| Mar. 8, 1988 | [JP] | Japan | 63-52510 |
| Mar. 10, 1988 | [JP] | Japan | 63-54751 |
| Mar. 12, 1988 | [JP] | Japan | 63-57353 |
| Mar. 14, 1988 | [JP] | Japan | 63-58246 |
| Mar. 17, 1988 | [JP] | Japan | 63-62034 |
| Mar. 18, 1988 | [JP] | Japan | 63-63702 |
| Mar. 25, 1988 | [JP] | Japan | 63-38476[U] |
| Mar. 28, 1988 | [JP] | Japan | 63-39733[U] |
| Mar. 30, 1988 | [JP] | Japan | 63-74730 |

[51] Int. Cl.[4] .................................................. A61B 1/00
[52] U.S. Cl. .................................................. 128/4
[58] Field of Search .......................... 128/4, 6; 358/98

[56] References Cited

U.S. PATENT DOCUMENTS 4,618,884 10/1986 Nagasaki .......................... 128/6 X Primary Examiner—William H. Grieb
Attorney, Agent, or Firm—Stevens, Davis, Miller & Mosher

[57] ABSTRACT

An endoscope apparatus for inspecting an object including an insertion section insertable into the object and having a distal end and a proximal end, an image guide arranged within the insertion section and having entrance and exit ends arranged at the distal and proximal ends of insertion section, respectively, an objective lens system arranged at the distal end of insertion section for forming an optical image of the object onto the entrance end of image guide, an eyepiece lens system arranged at the proximal end of insertion section for projecting the optical image transmitted through the image guide onto an observating position, a first piezoelectric bimorph arranged at the distal end of insertion section for vibrating the entrance end of image guide in a direction perpendicular to a longitudinal axis of the insertion section over a given distance, a second piezoelectric element arranged at the proximal end of insertion section for vibrating the exit end of image guide in the same direction and over the same distance as those of the entrance end of image guide, so that annoying black mesh and Moire fringe are removed.

36 Claims, 92 Drawing Sheets

FIG_1
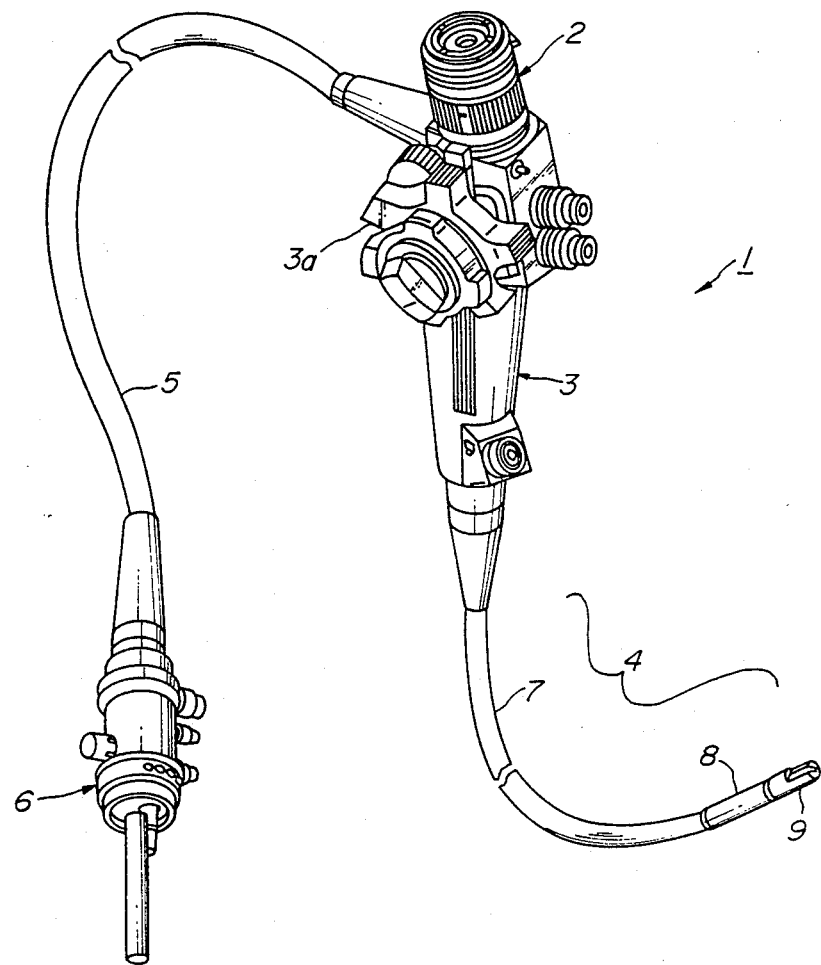

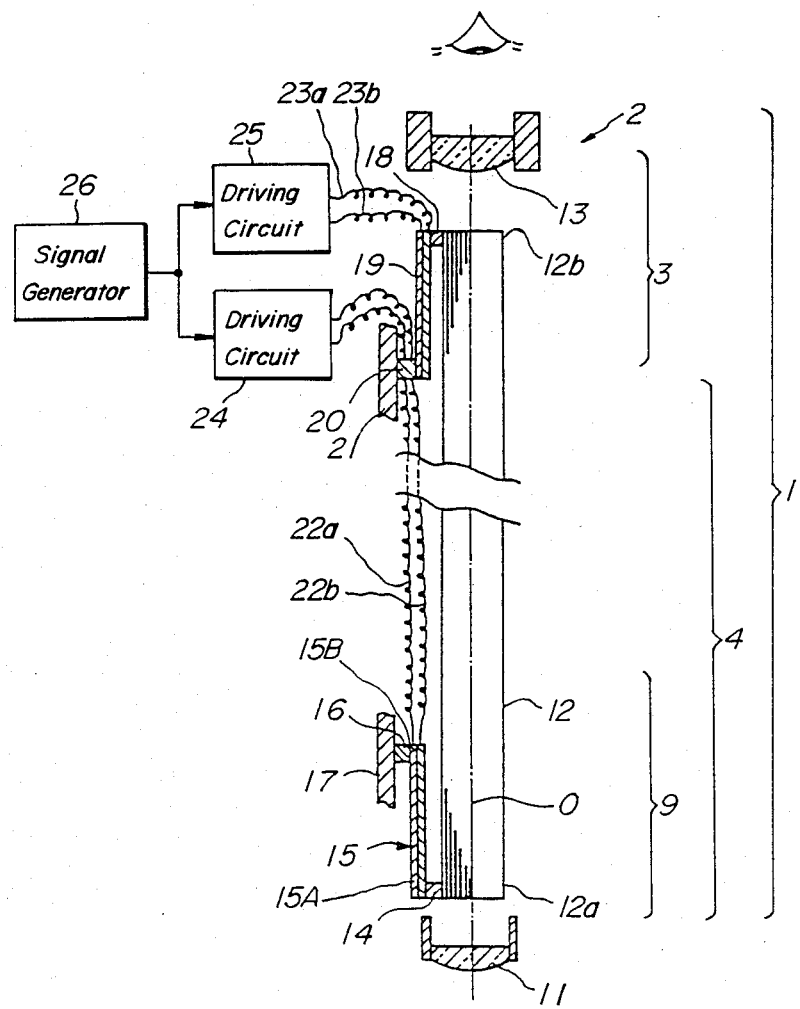
FIG_2

FIG._3
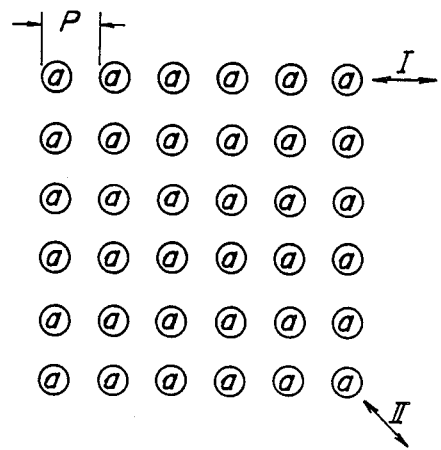
FIG._4
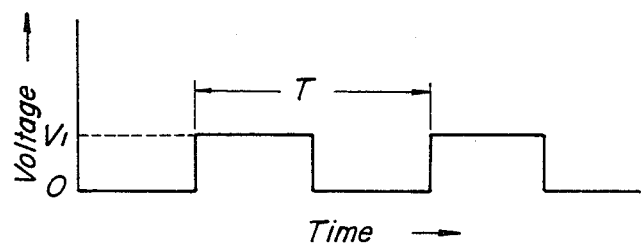

FIG_5
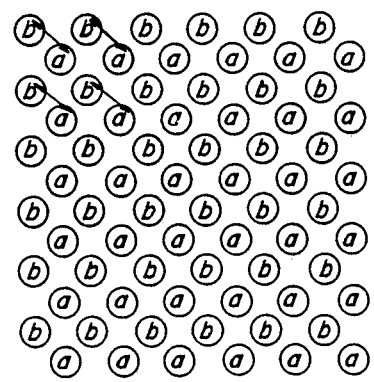
FIG_6

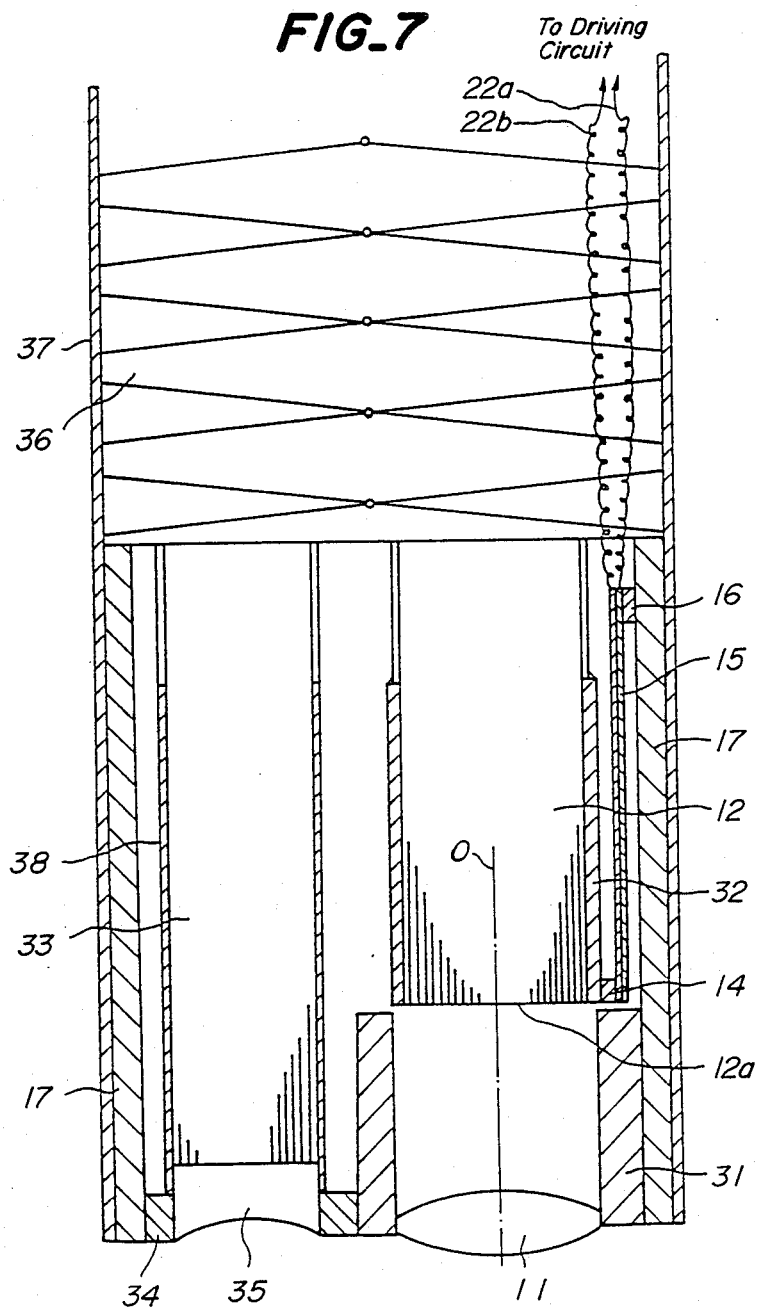

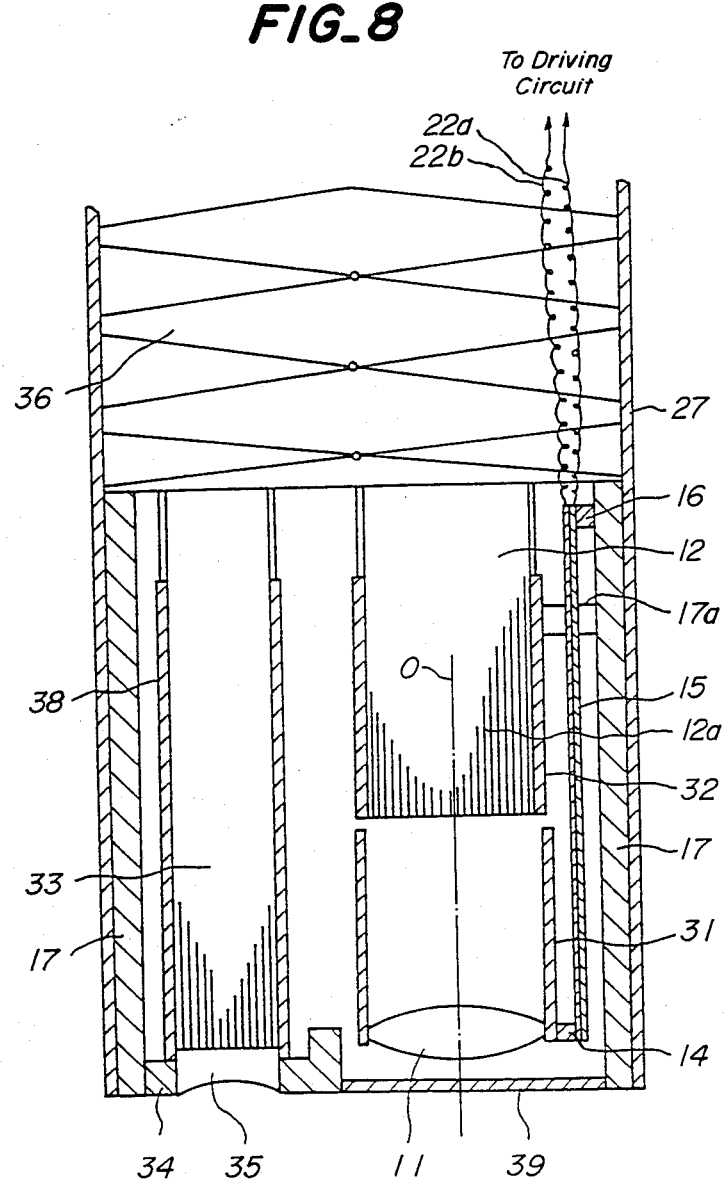
FIG_8

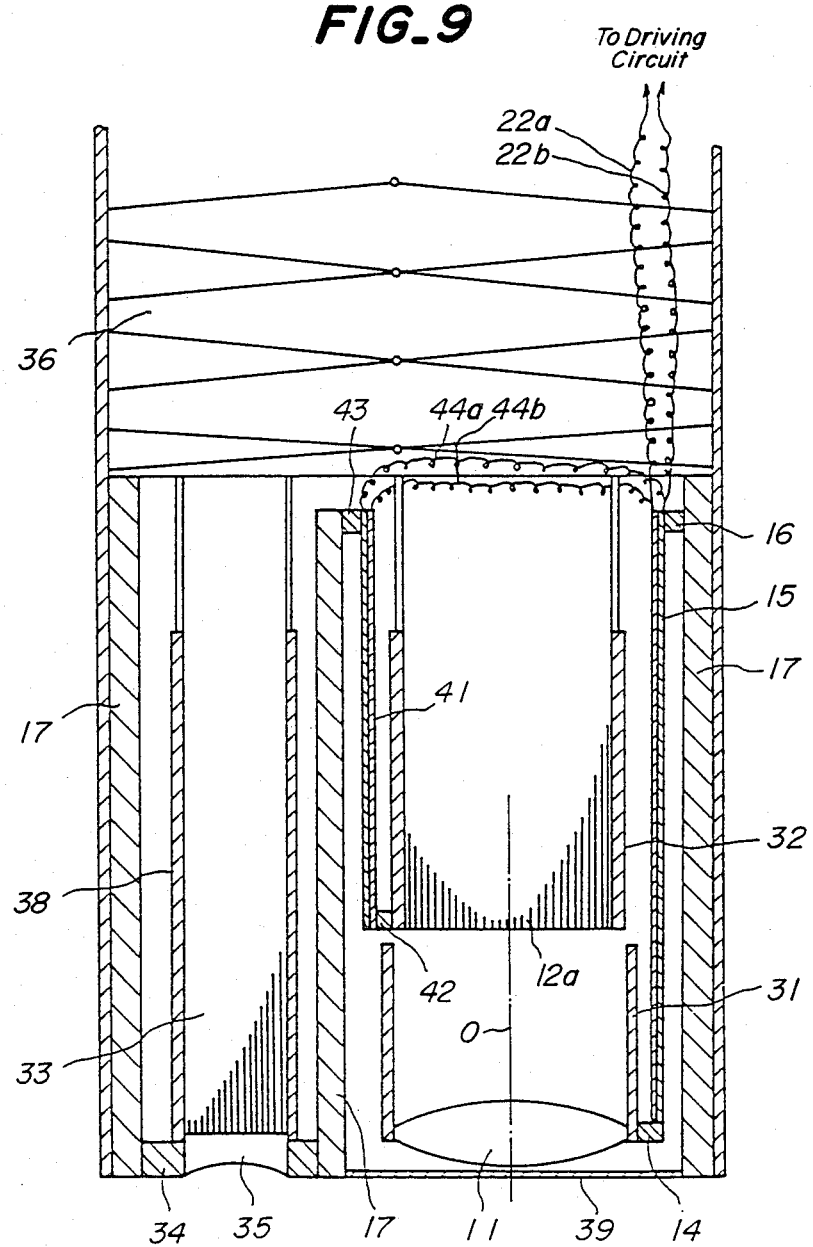

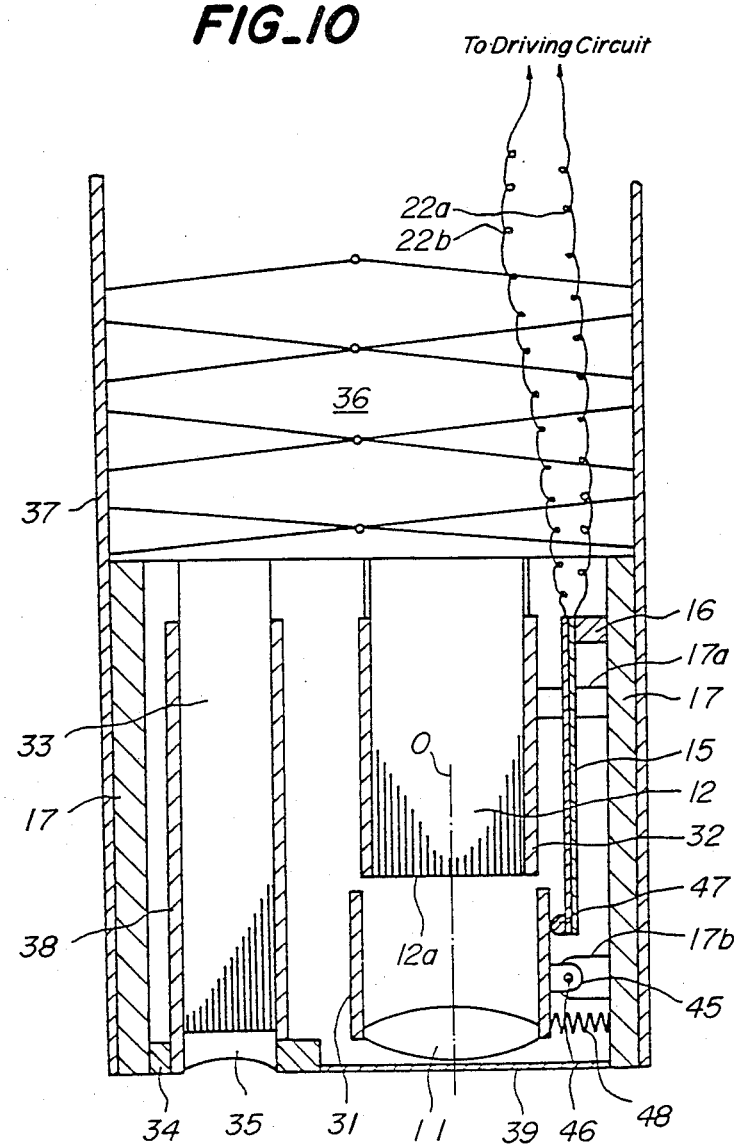

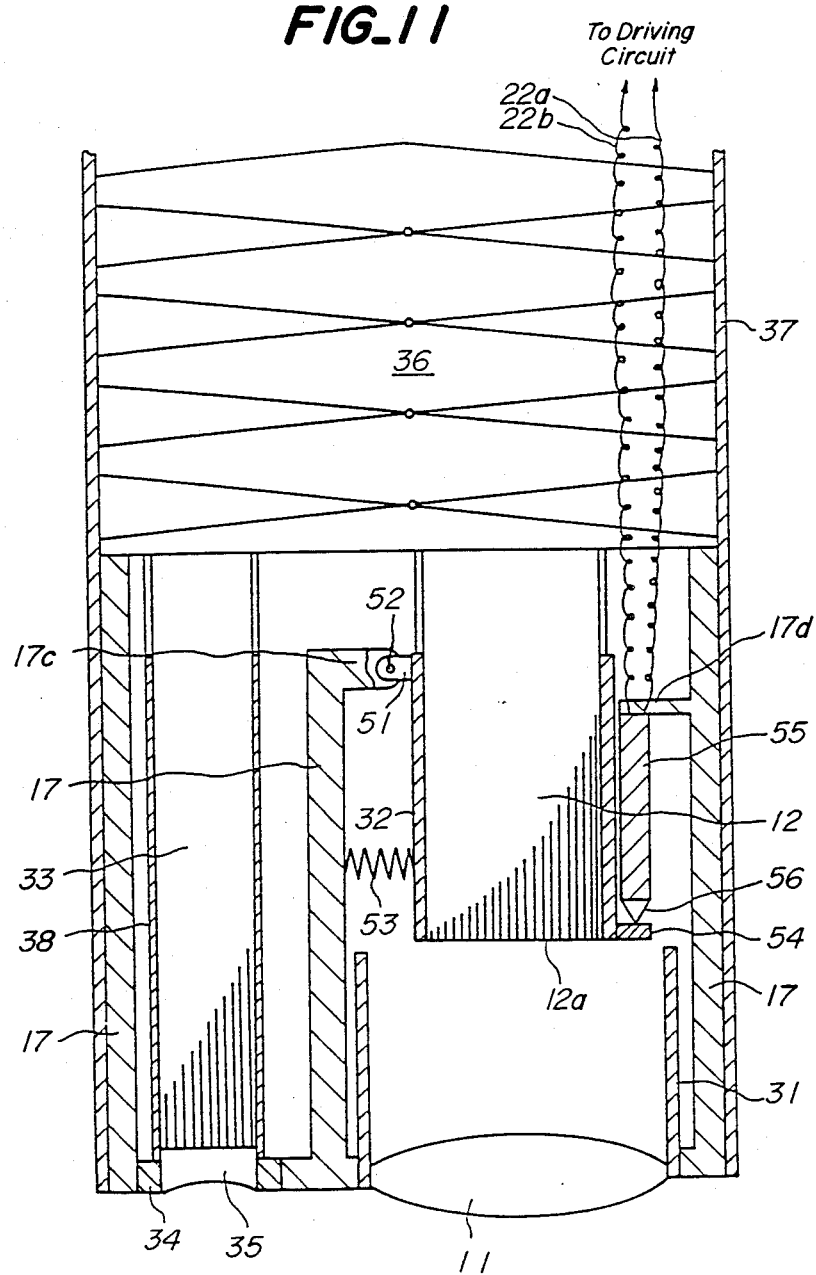

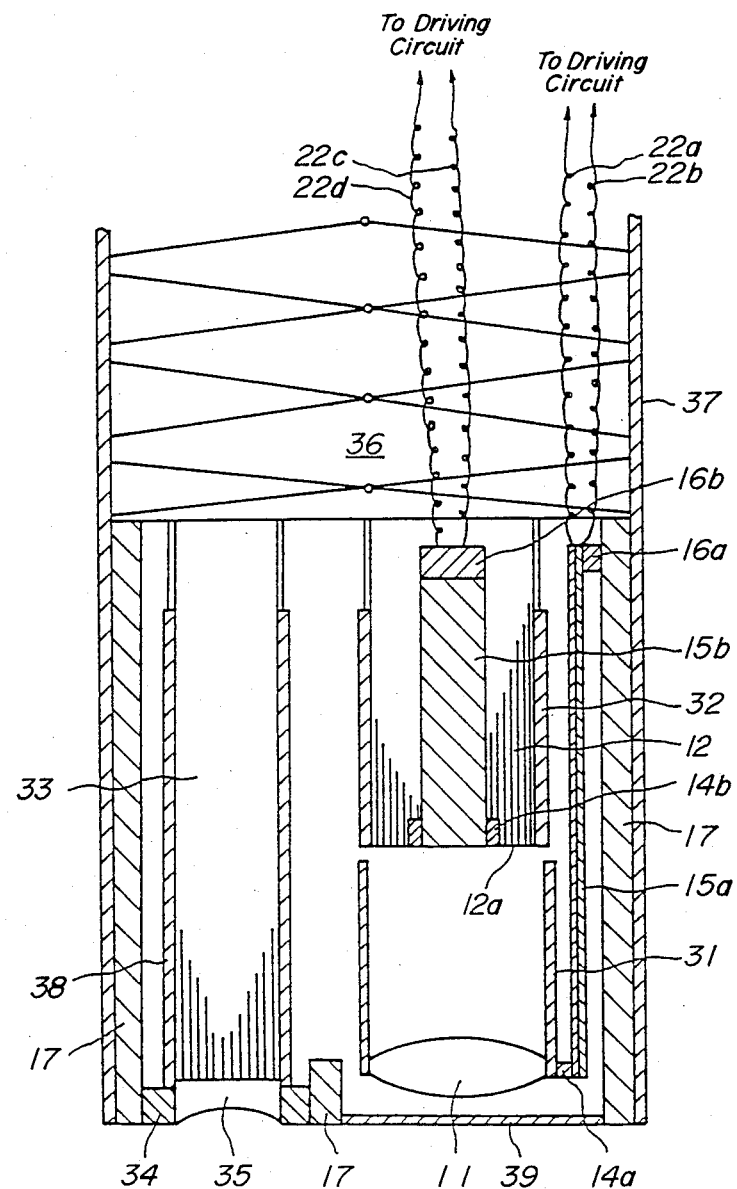
FIG_12

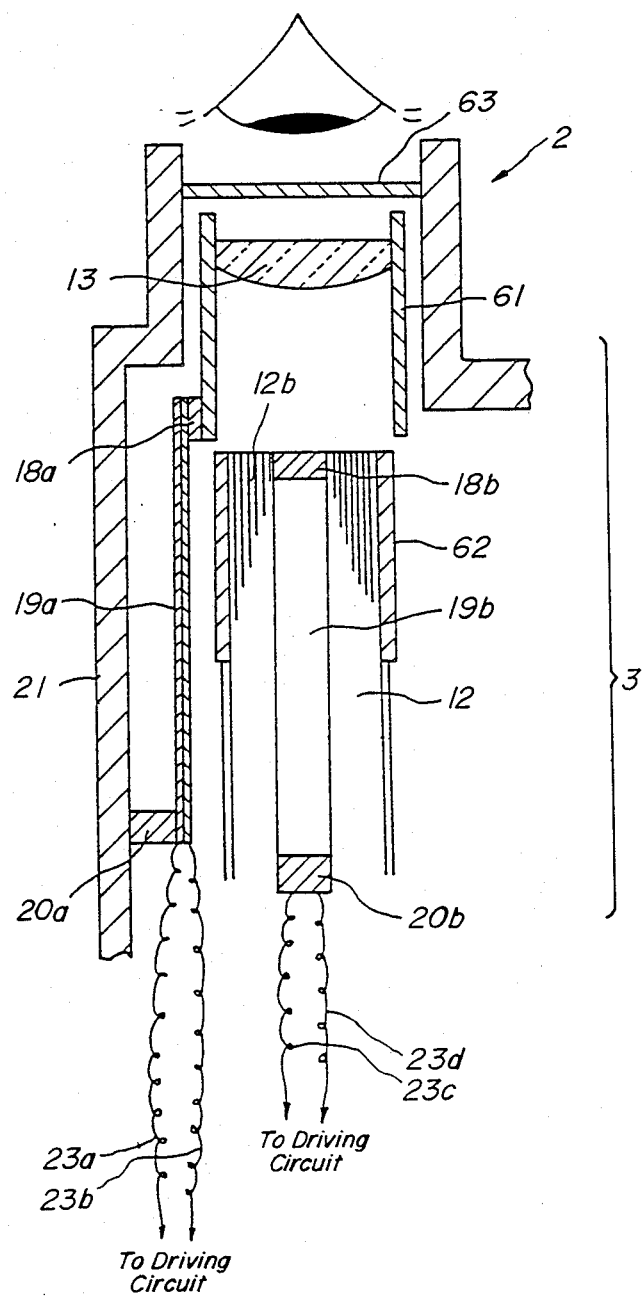
FIG_13

FIG_14A
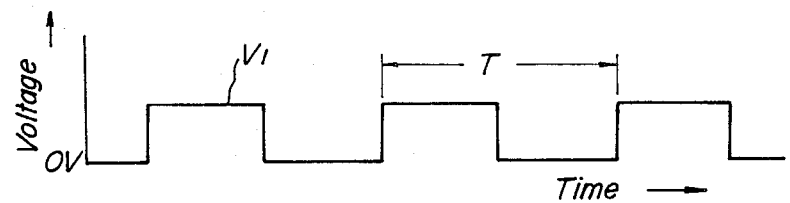
FIG_14B
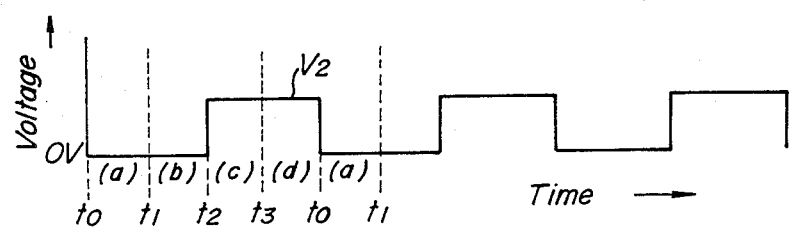
FIG_15
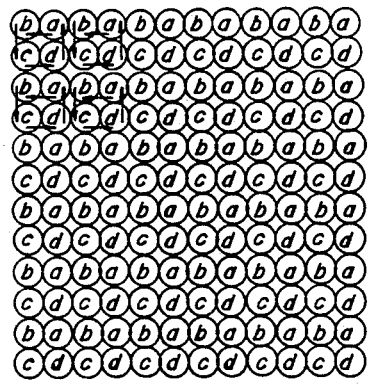

FIG_16
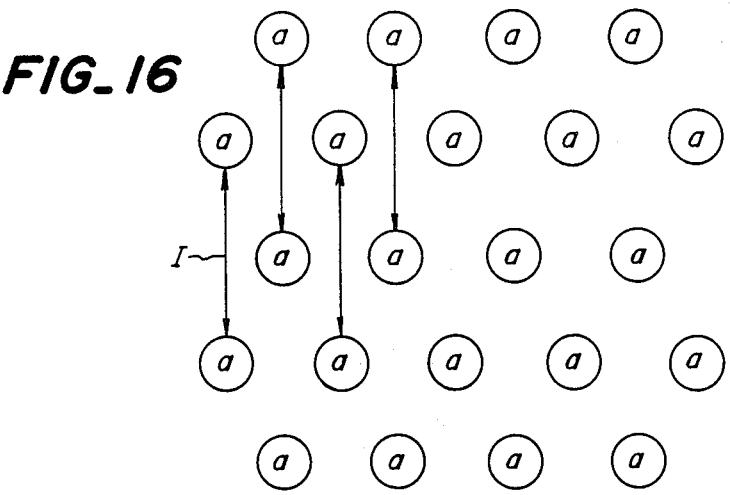
FIG_17
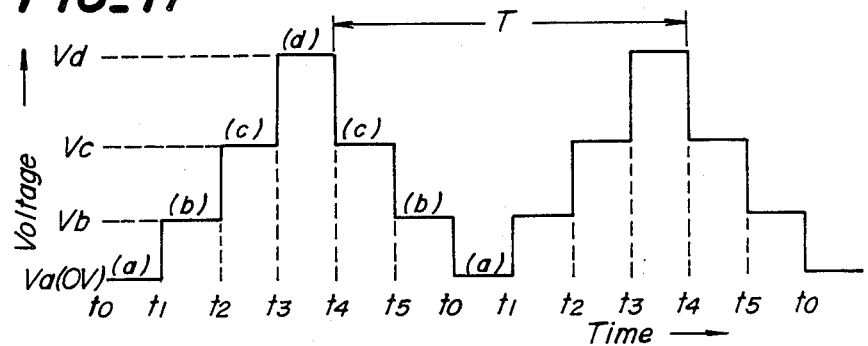
FIG_18
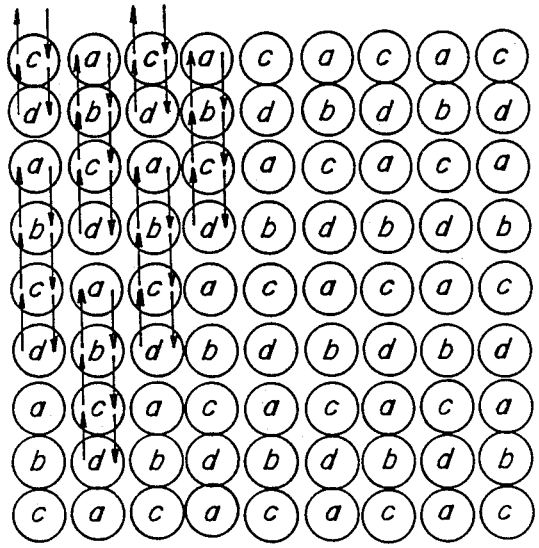

FIG_19
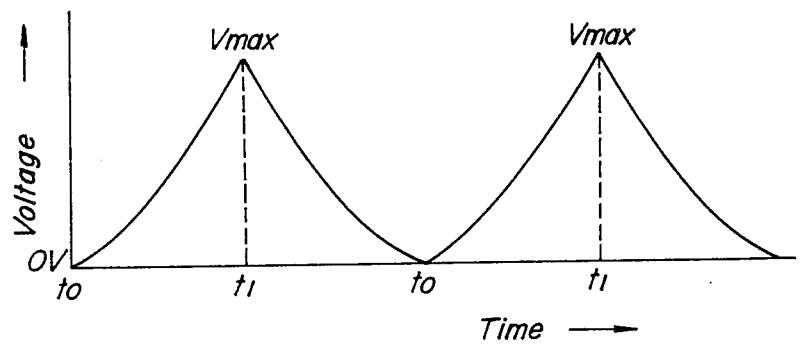
FIG_20
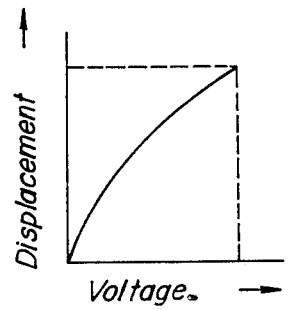
FIG_21
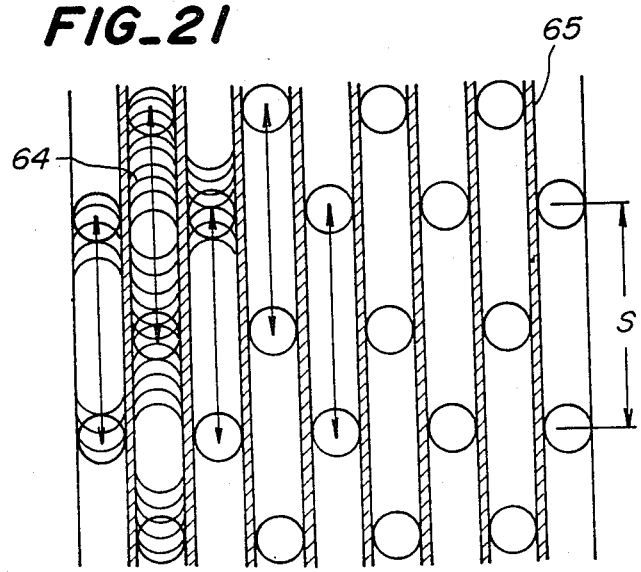

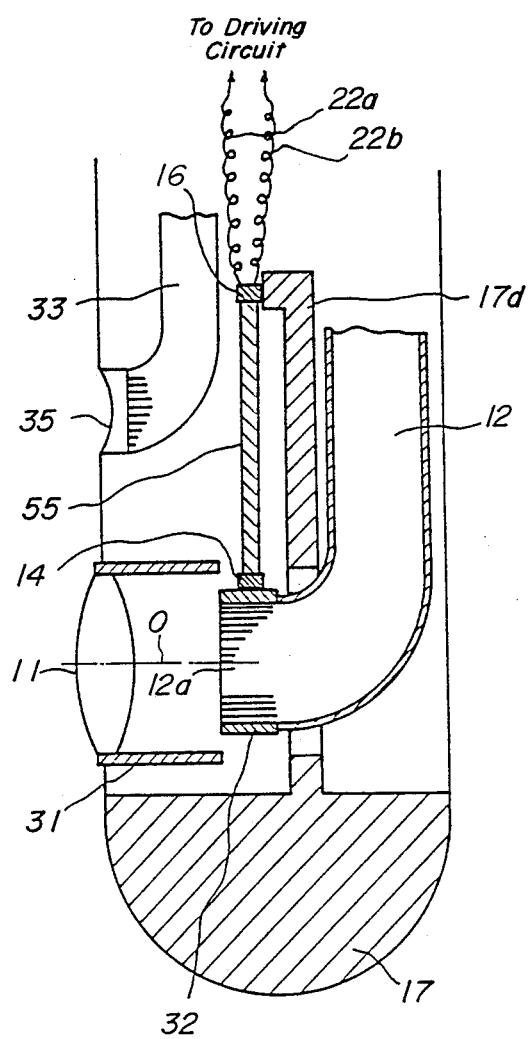
FIG_22

FIG_23A
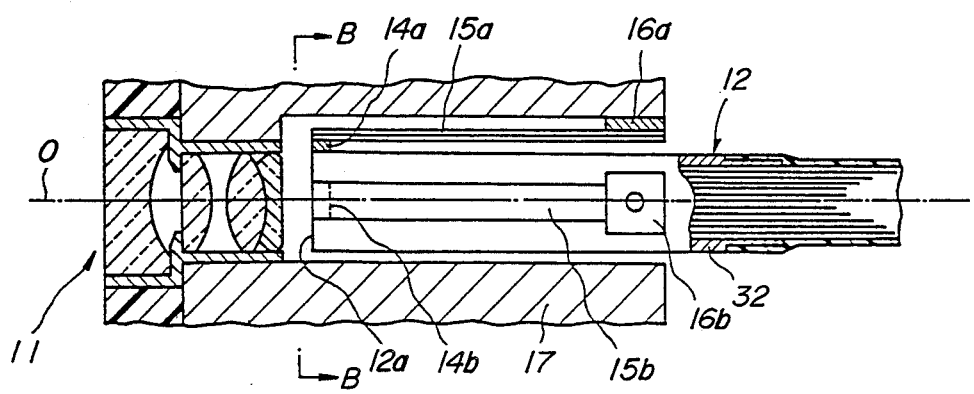
FIG_23B
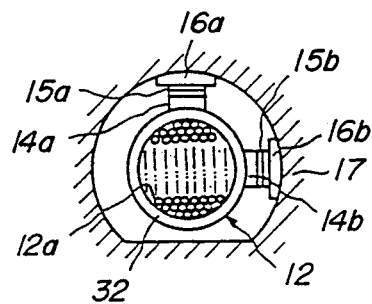

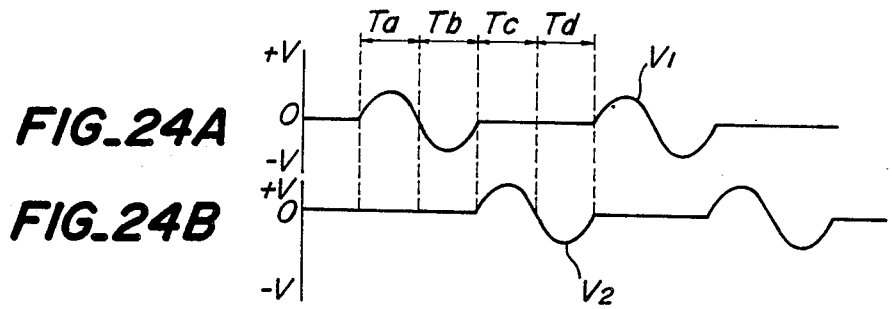
FIG.24A
FIG.24B
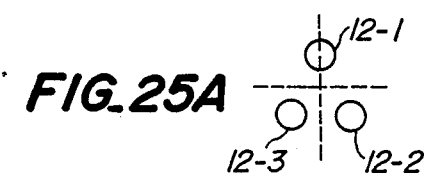
FIG.25A
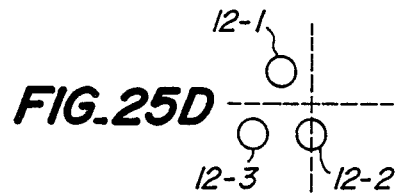
FIG.25D
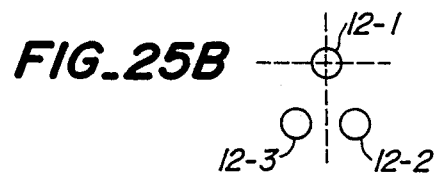
FIG.25B
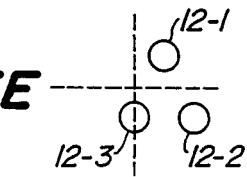
FIG.25E
FIG.25C

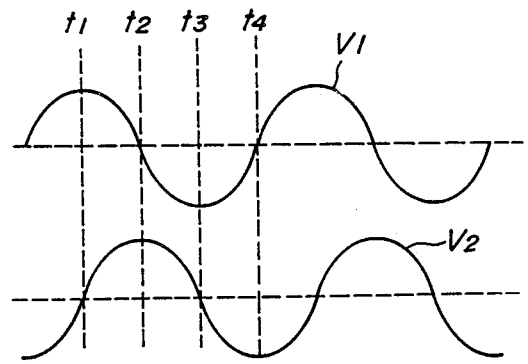
FIG._26A
FIG._26B
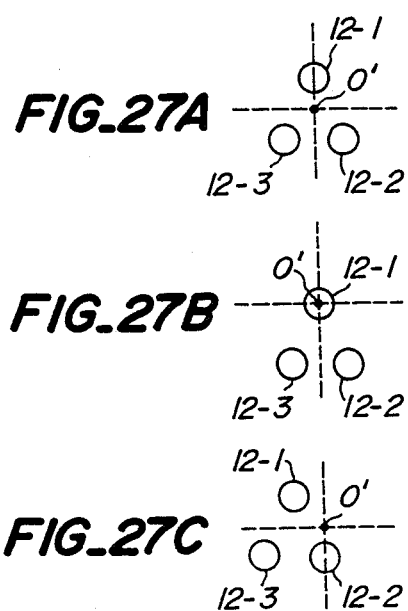
FIG._27A
FIG._27B
FIG._27C
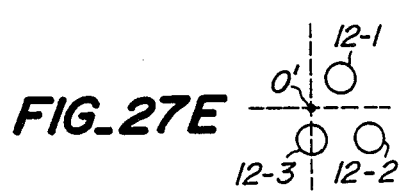
FIG._27D
FIG._27E

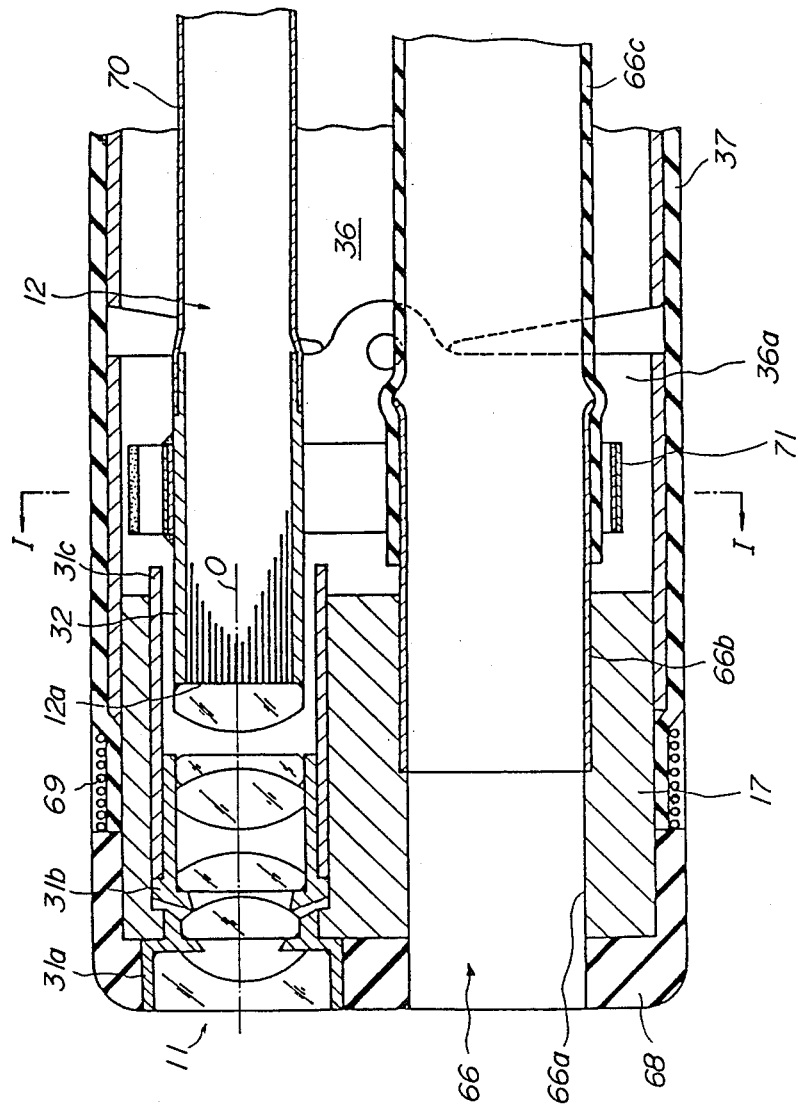

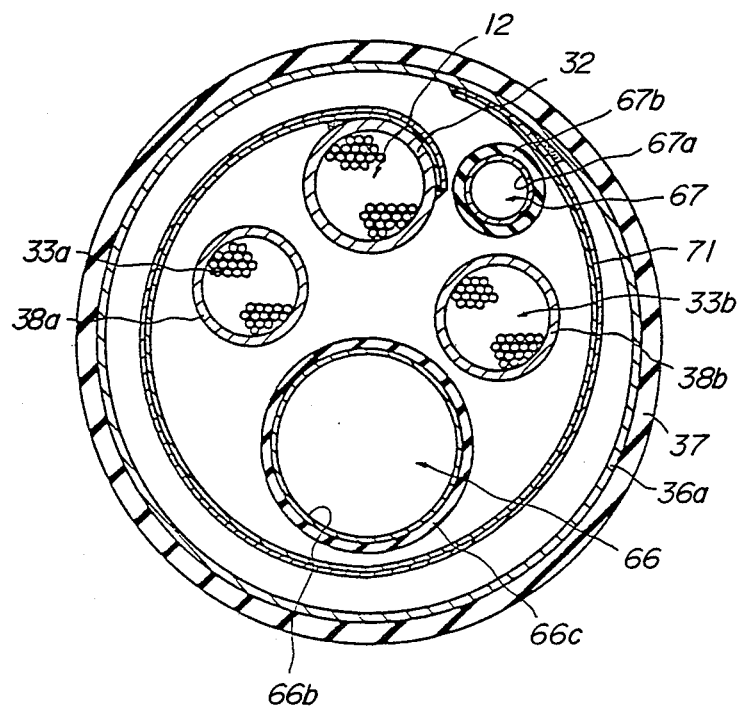
FIG_28B

FIG._29A
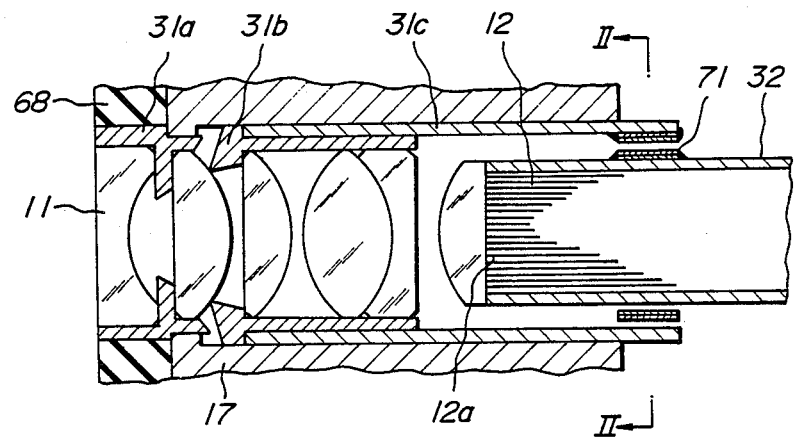
FIG._29B
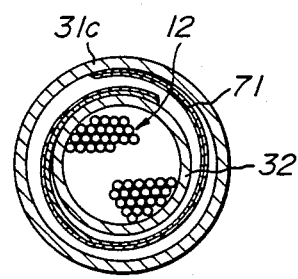

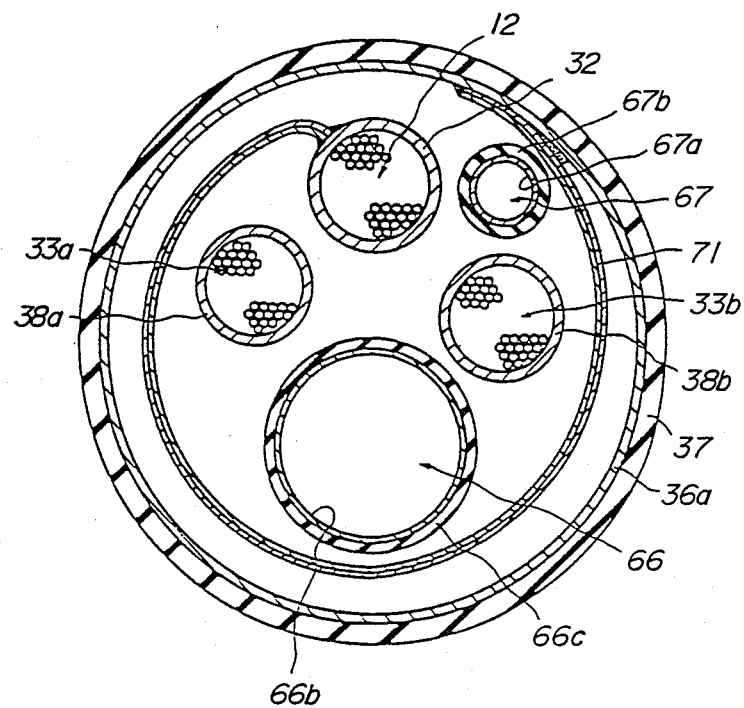
FIG_30

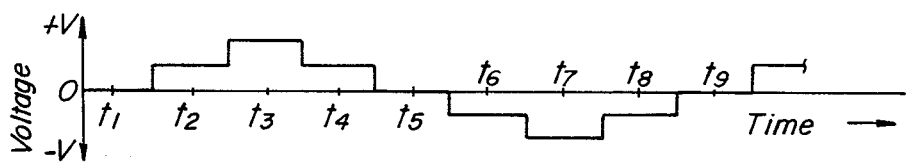
FIG._32A
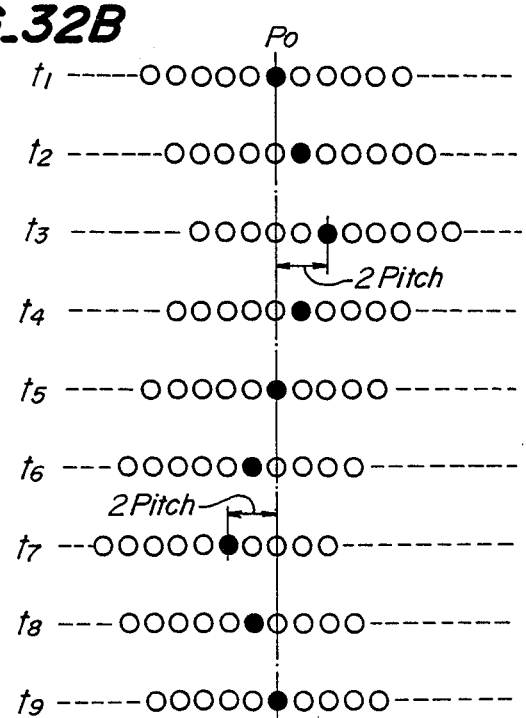
FIG._32B
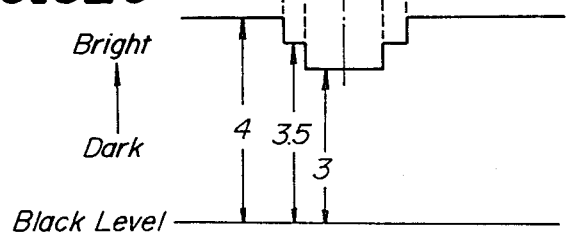
FIG._32C

FIG_34A
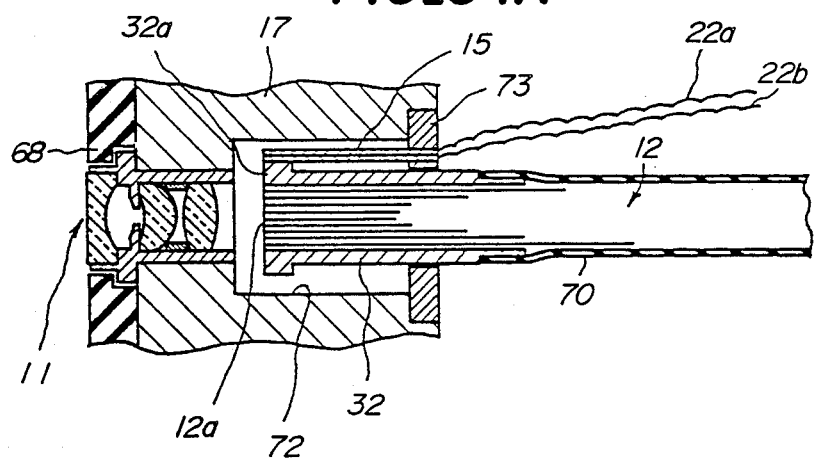
FIG_34B
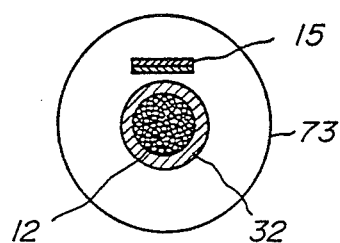
FIG_35
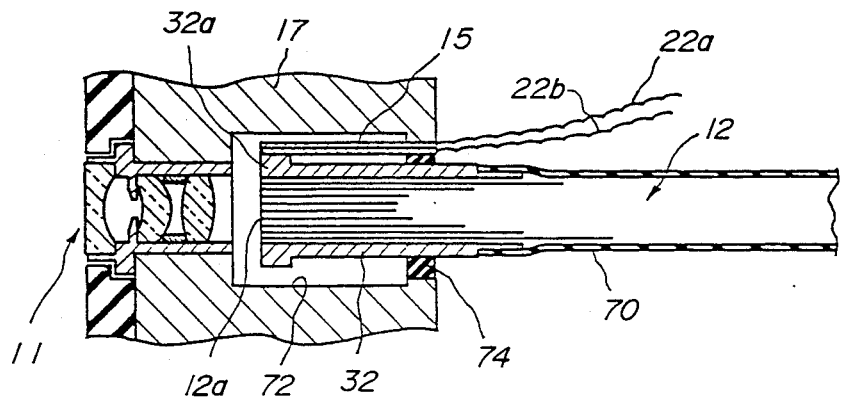

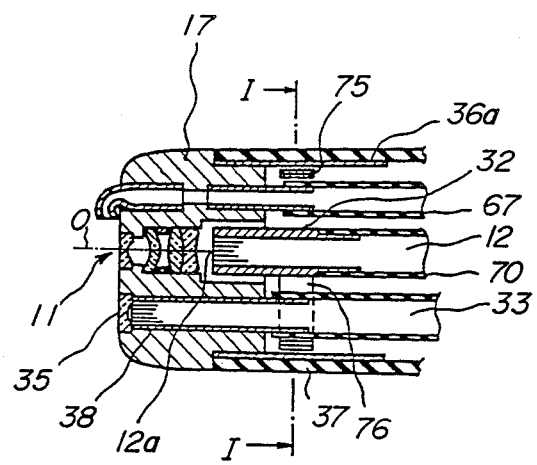
FIG_36A
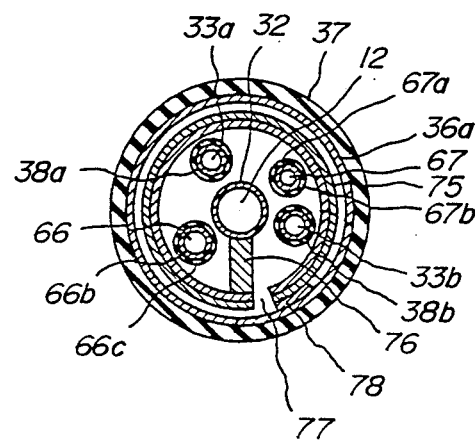
FIG_36B

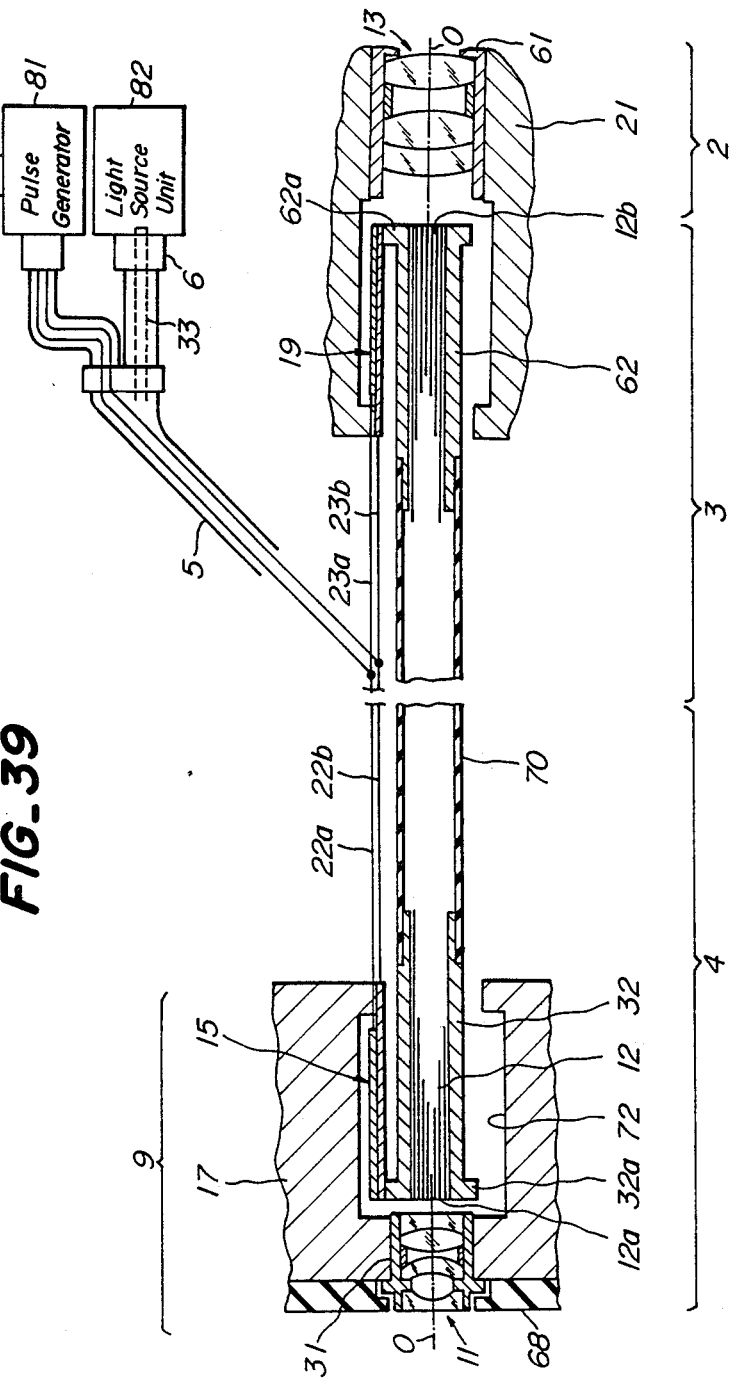
FIG_39

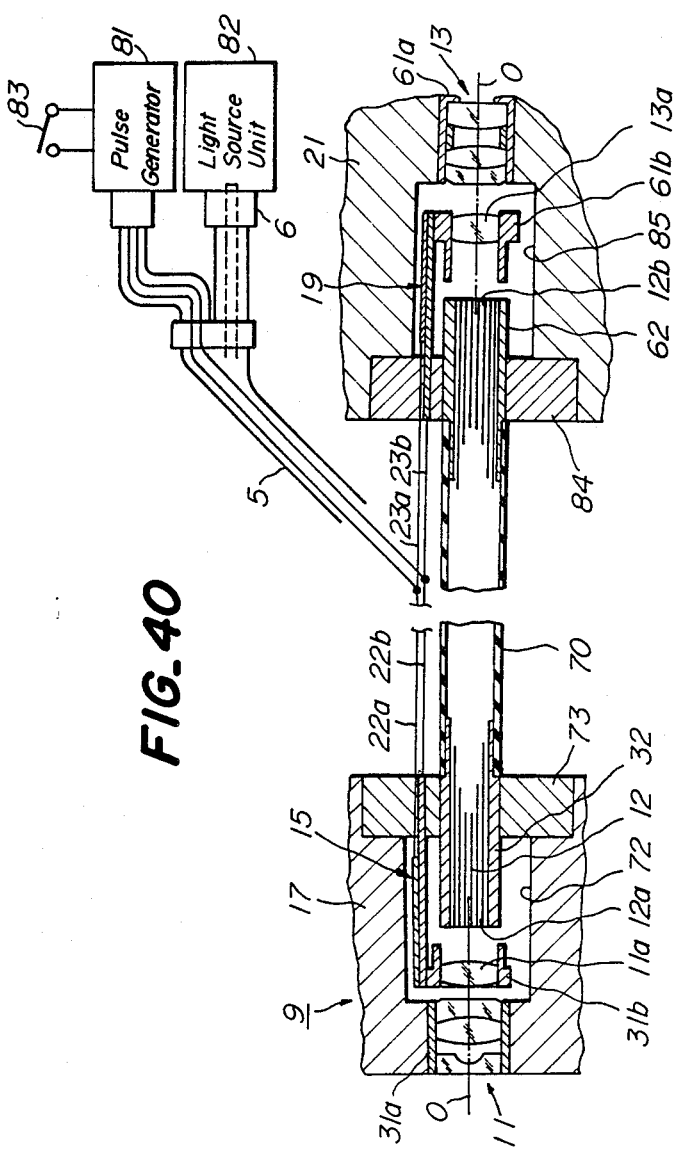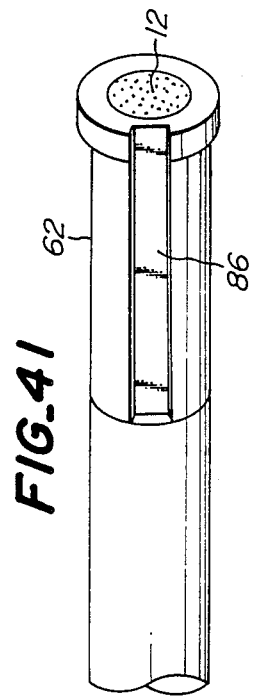

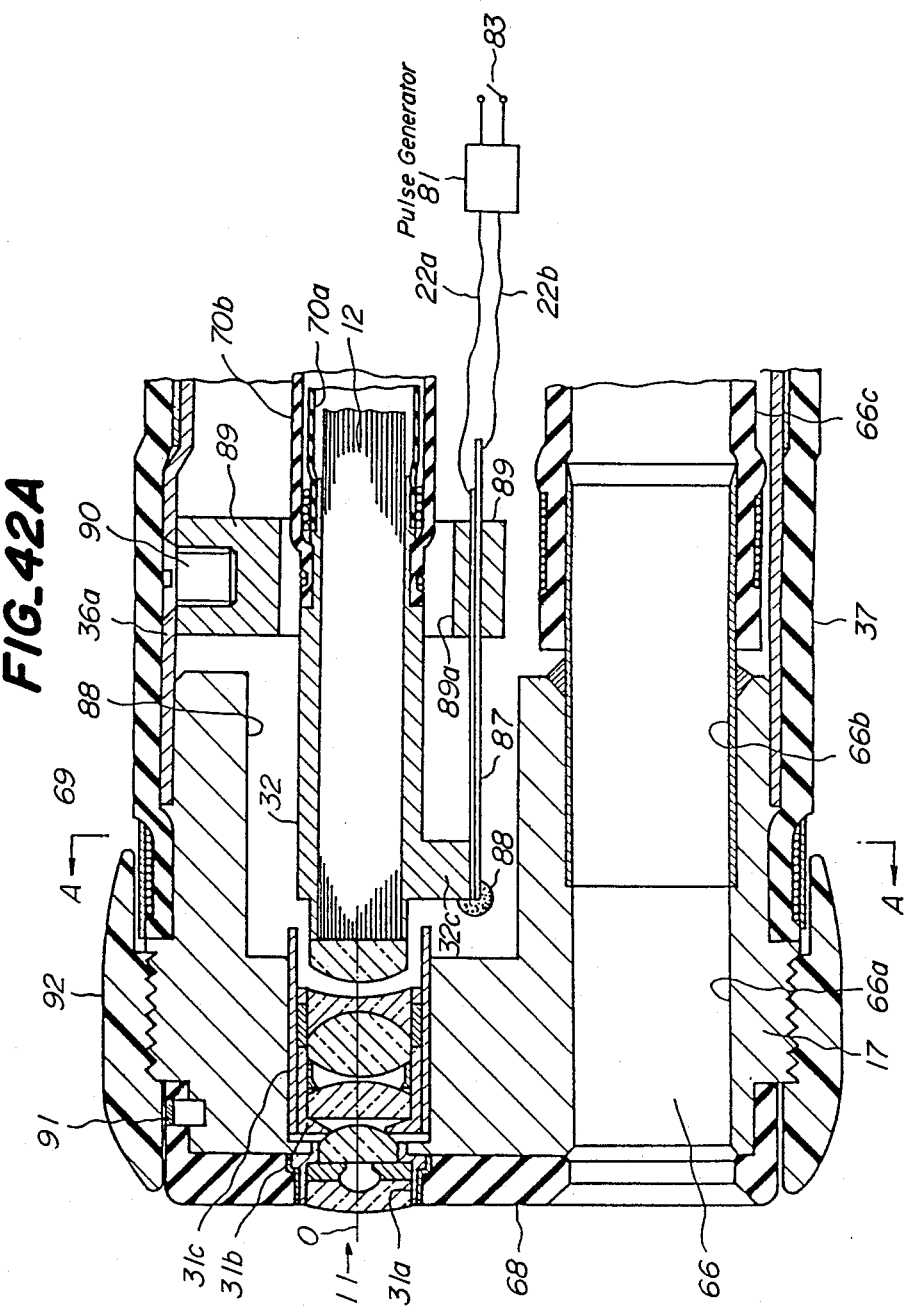

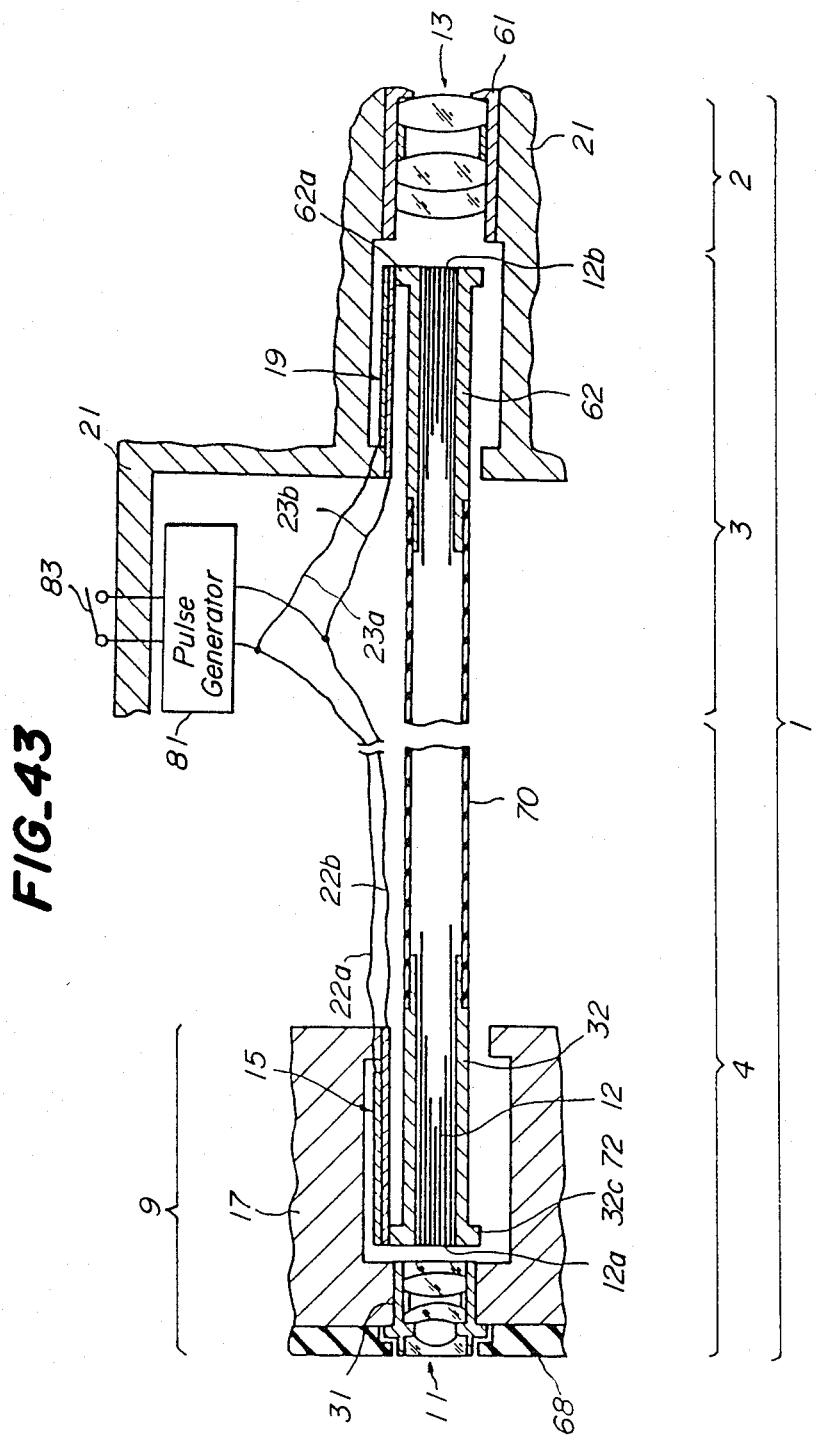
FIG._43

FIG_44
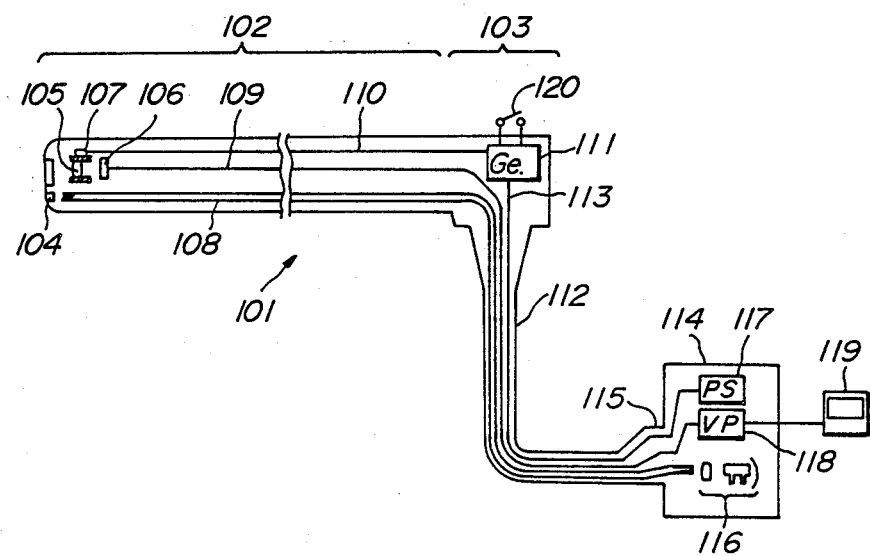

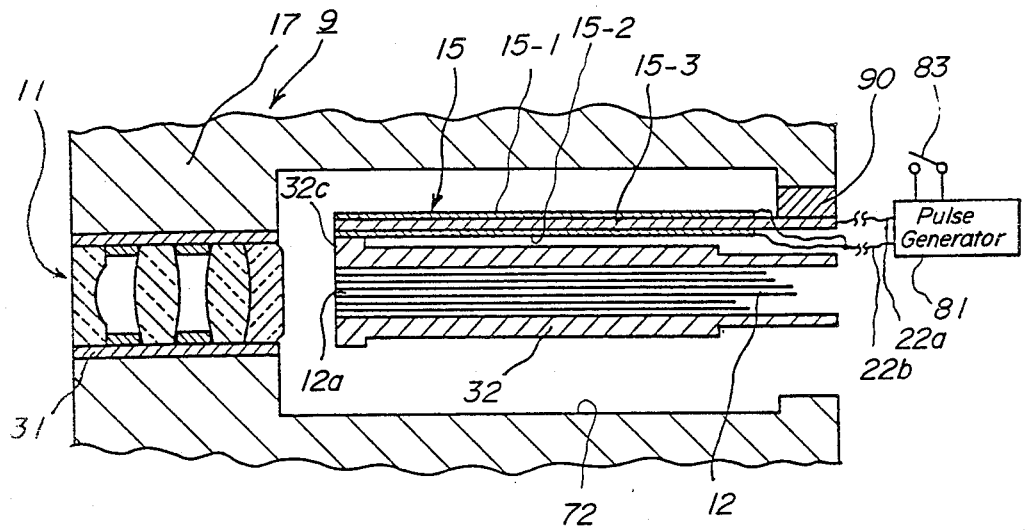
FIG_45
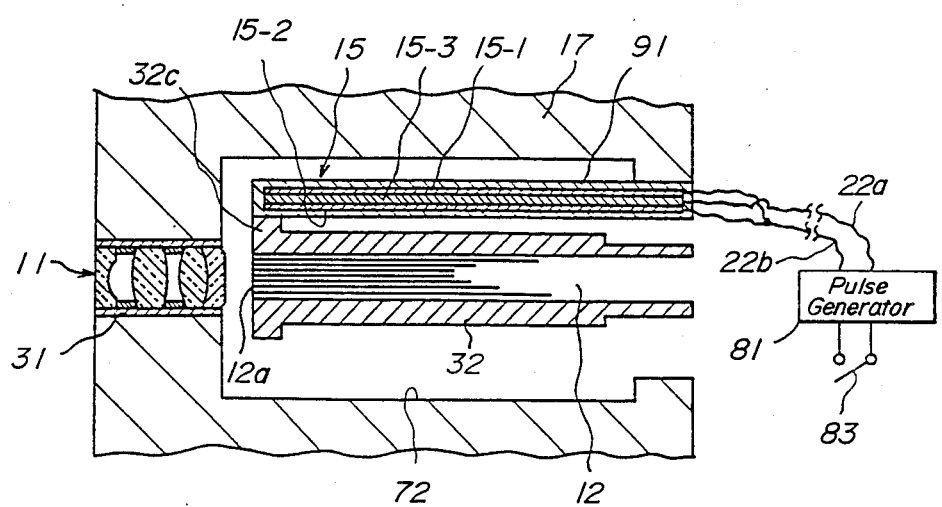
FIG_46

FIG_48
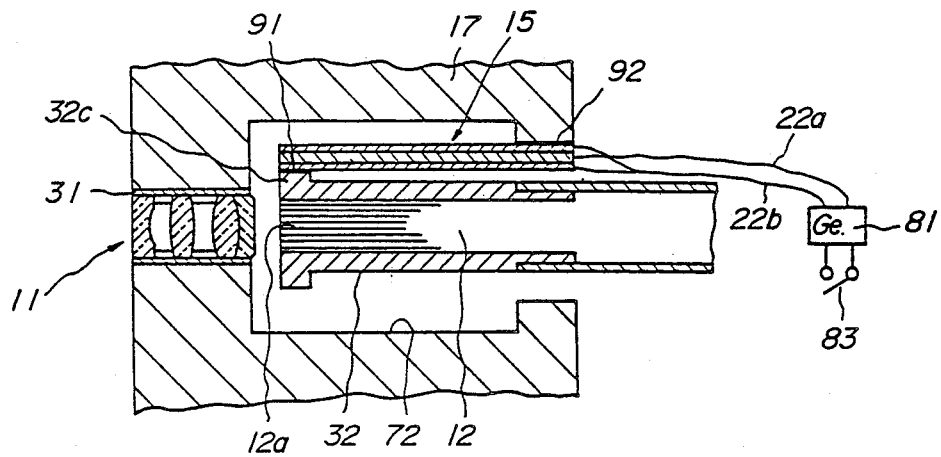
FIG_49
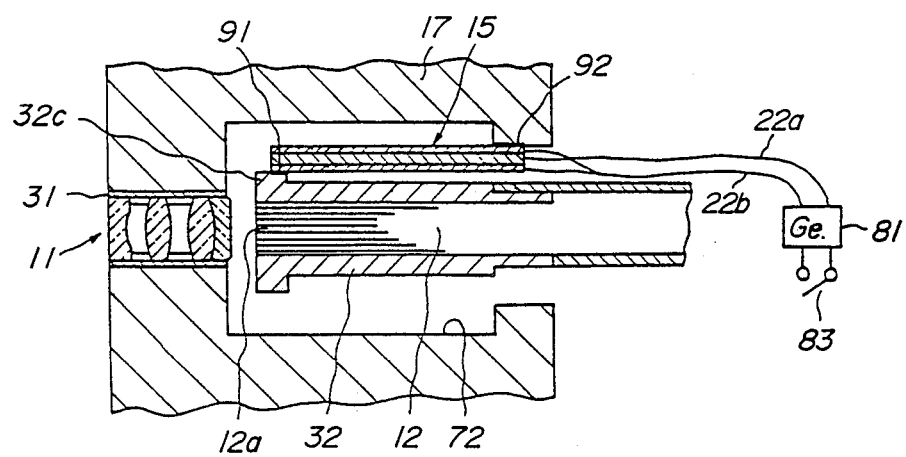

FIG_50A
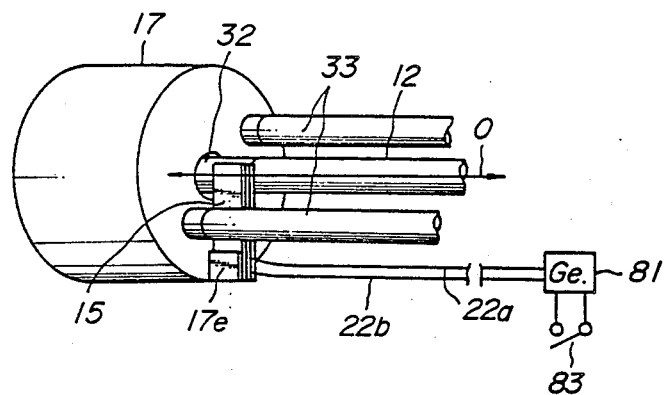
FIG_50B
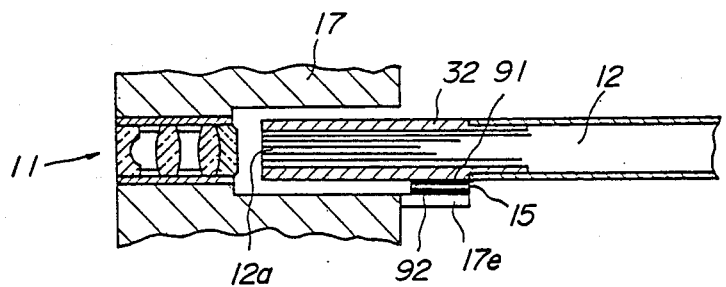

FIG_51A
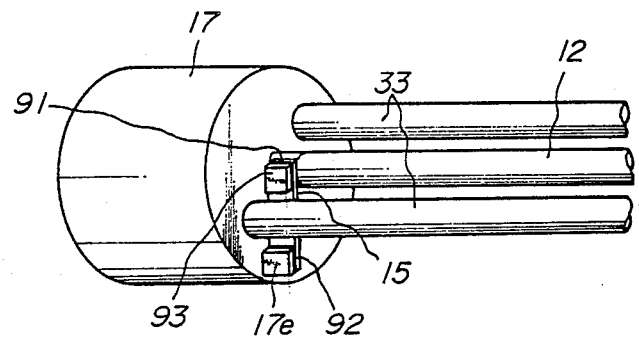
FIG_51B
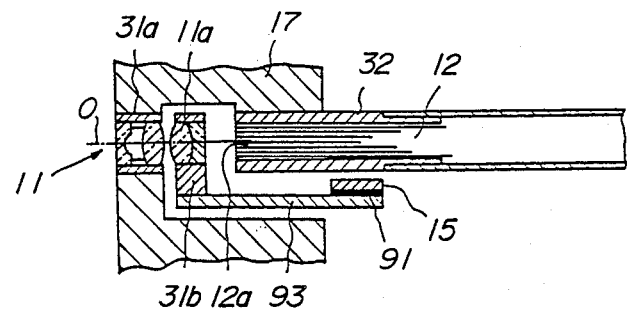

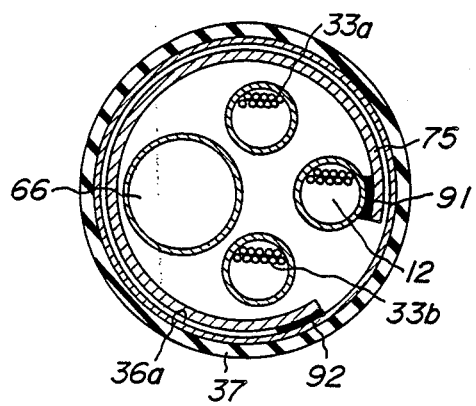
FIG_52
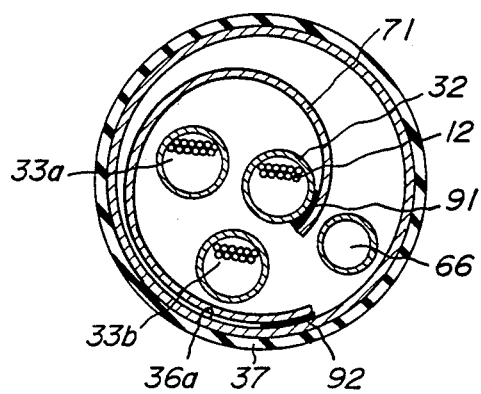
FIG_53

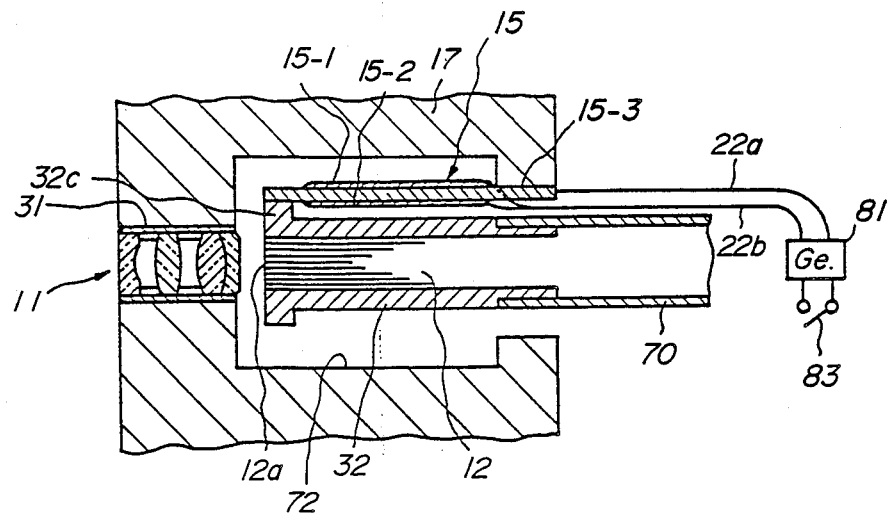
FIG_54
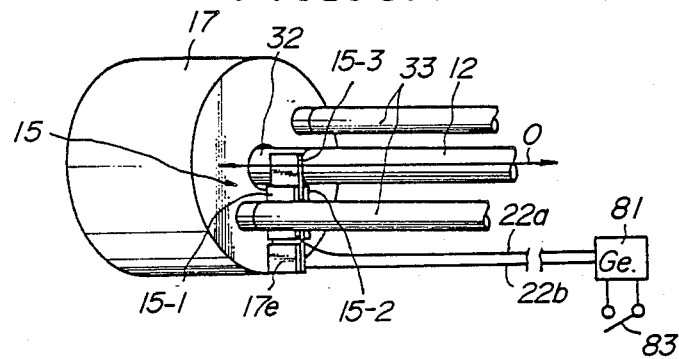
FIG_55A
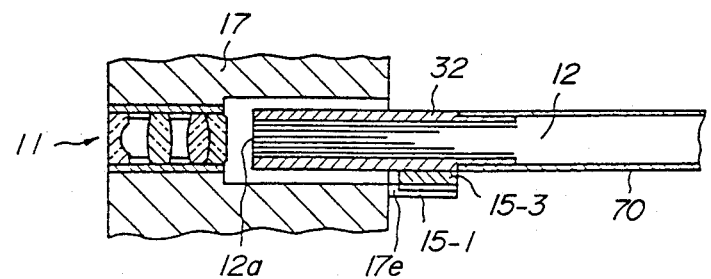
FIG_55B

FIG_61A
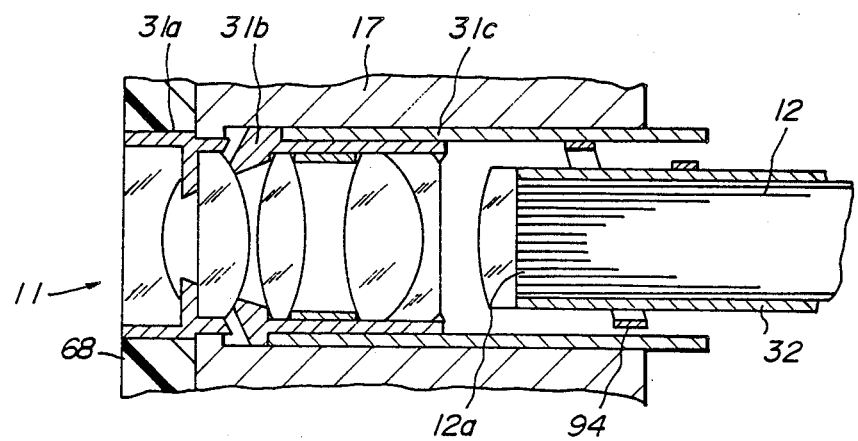
FIG_61B
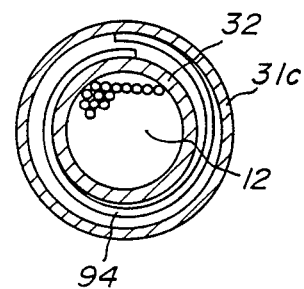

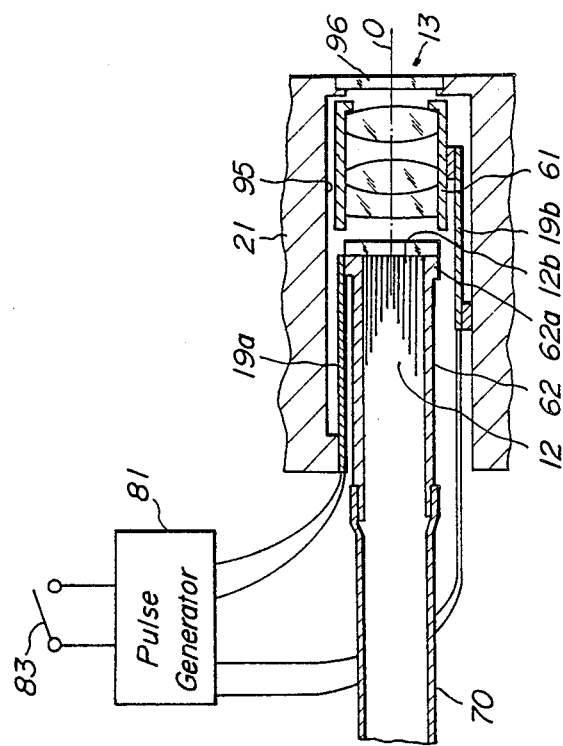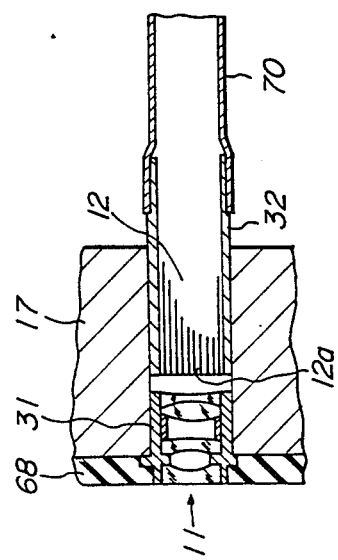
FIG. 64

FIG_67A
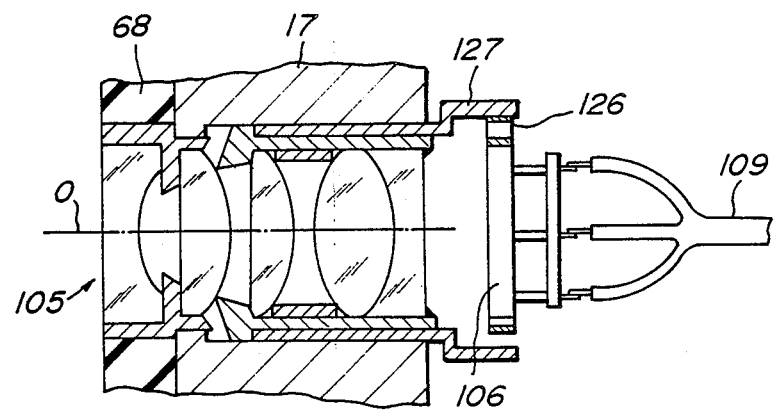
FIG_67B
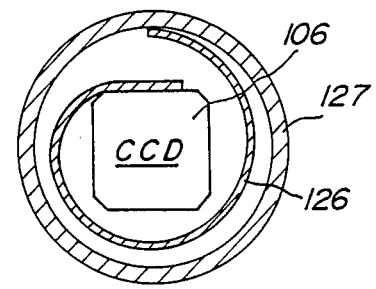

FIG_68
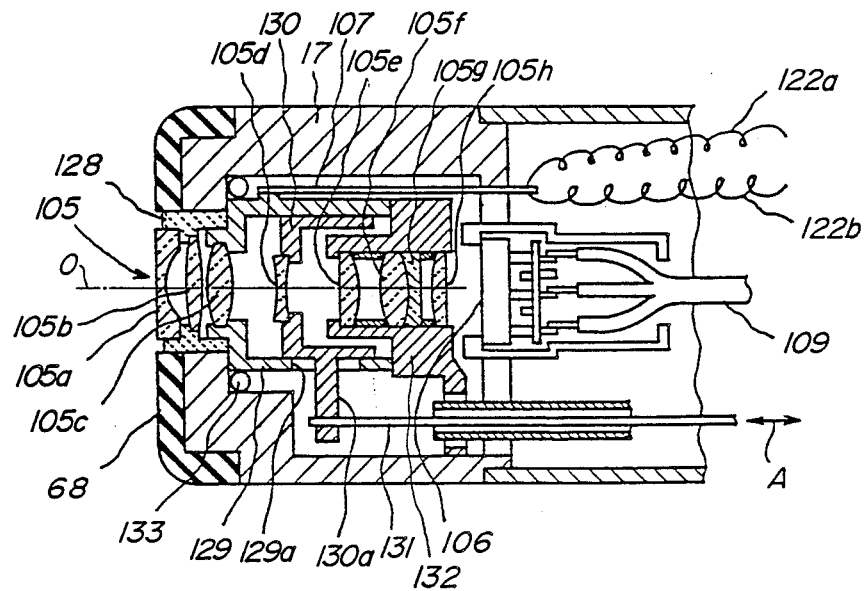
FIG_69
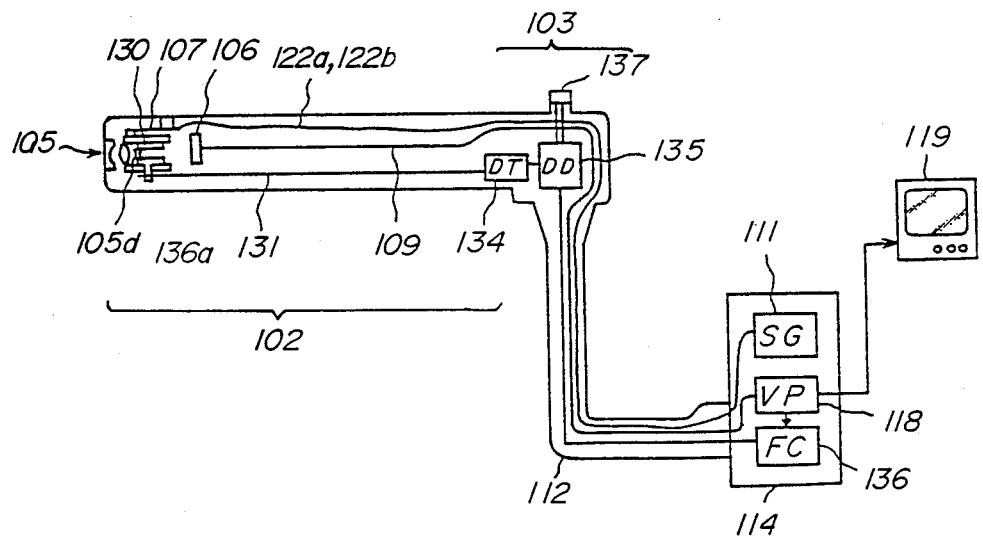

FIG_71A 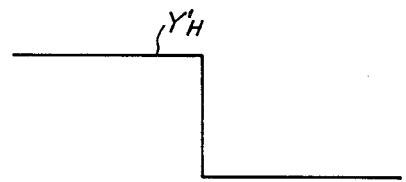
FIG_71B 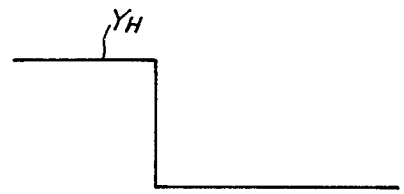
FIG_71C 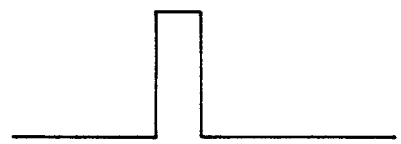
FIG_71D 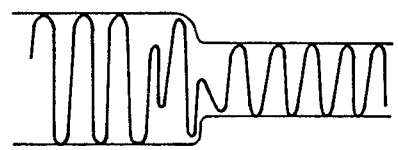
FIG_71E 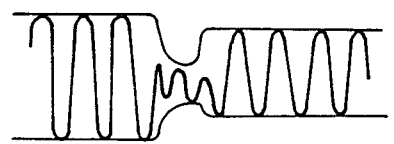

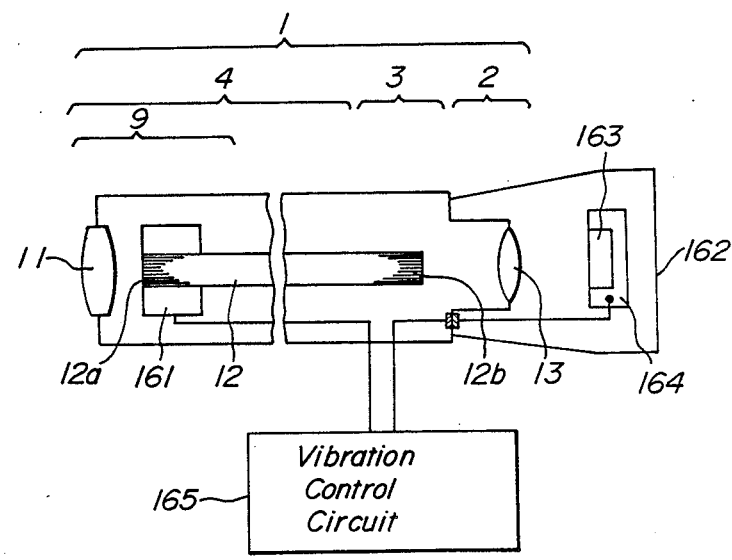
FIG_72

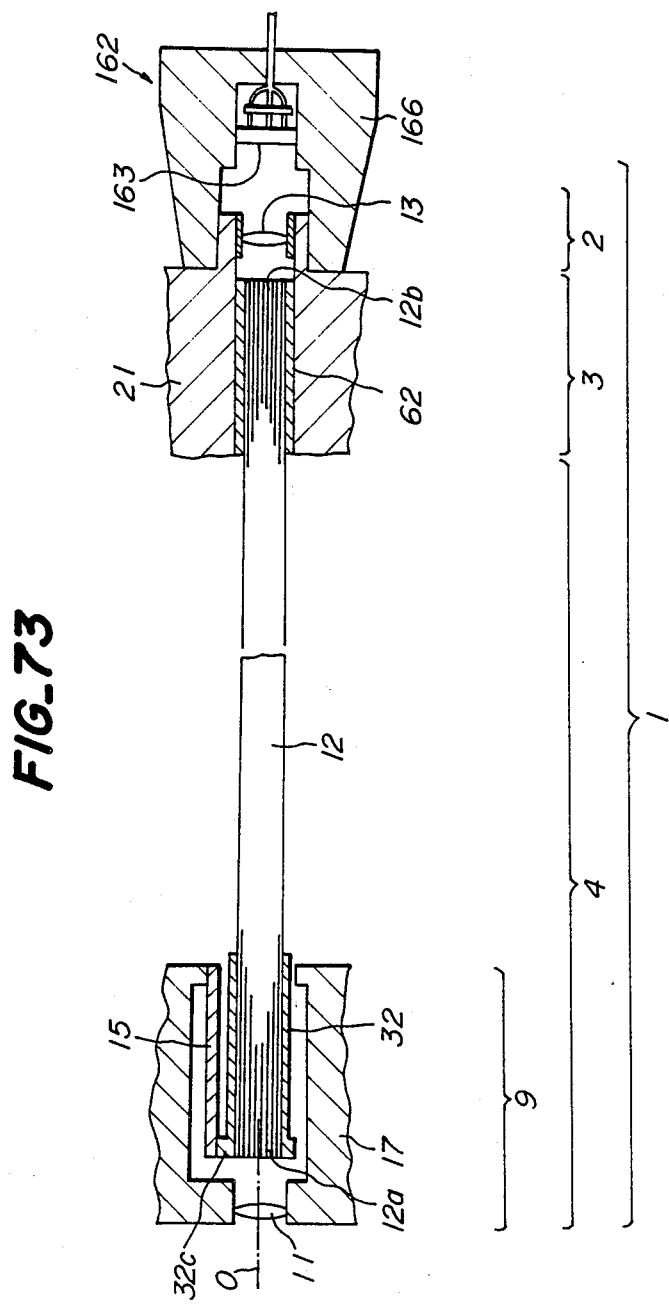

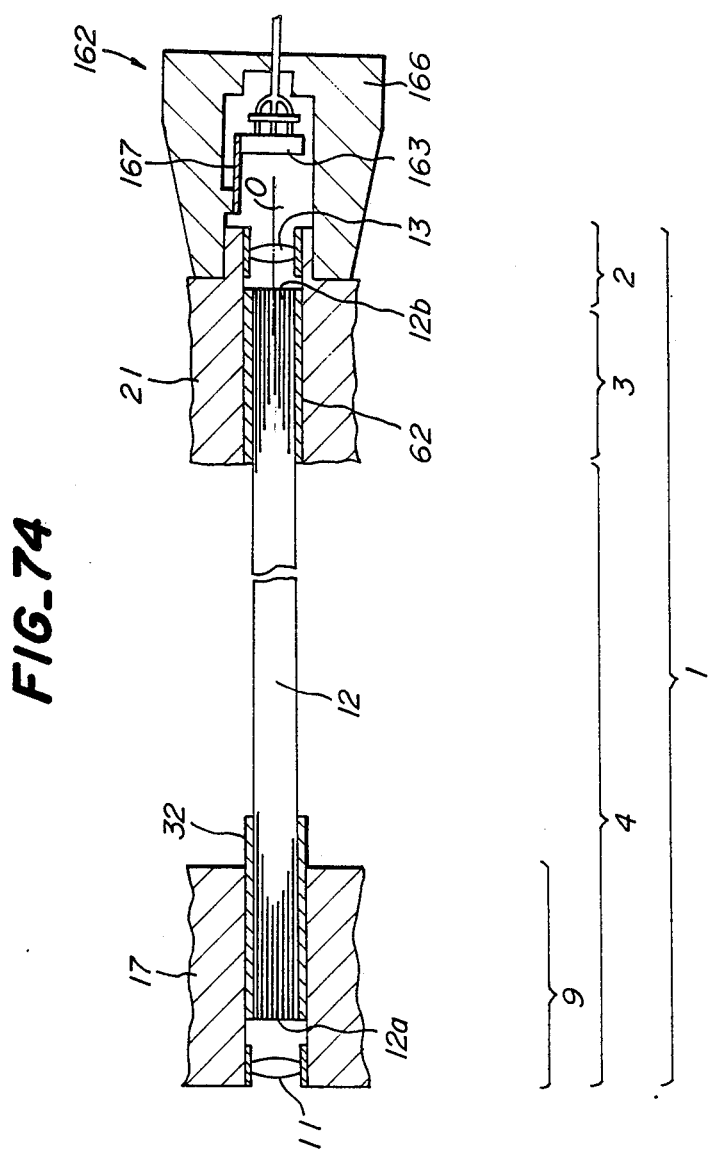
FIG._74

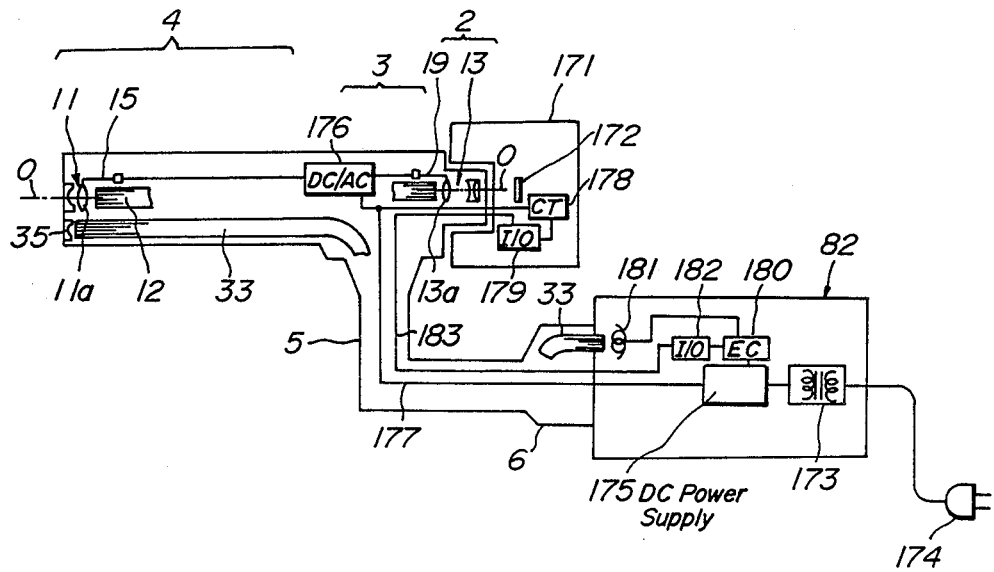
FIG_75
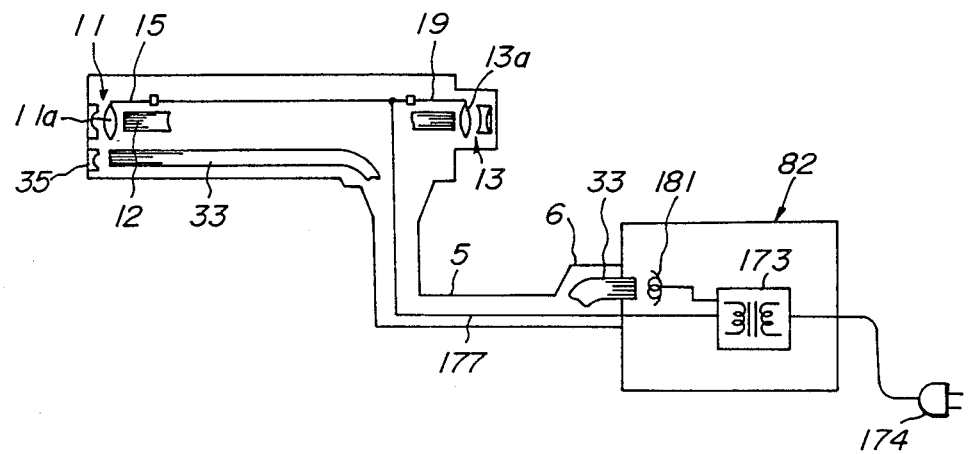
FIG_76

FIG_77
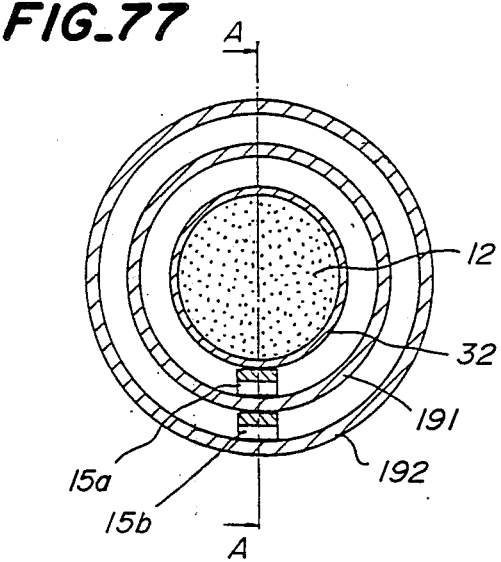
FIG_78A
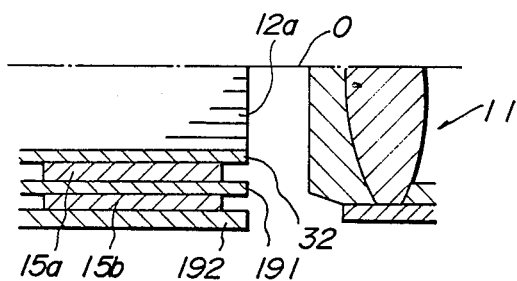
FIG_78B
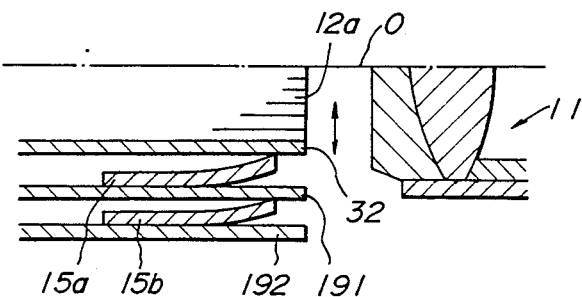

FIG_79
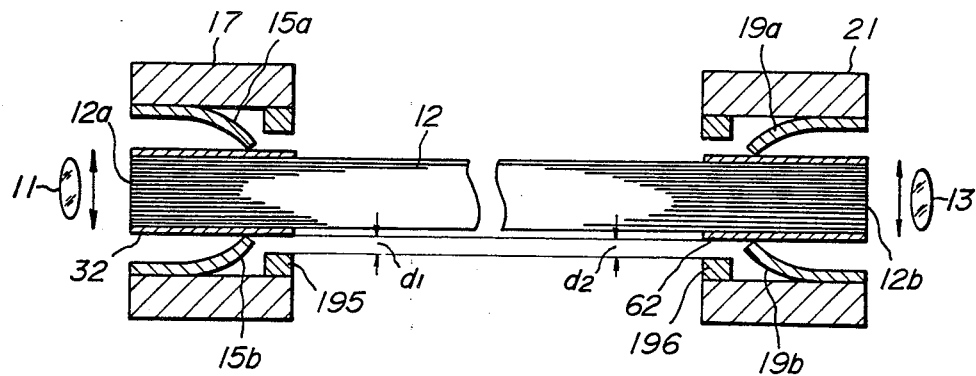
FIG_80
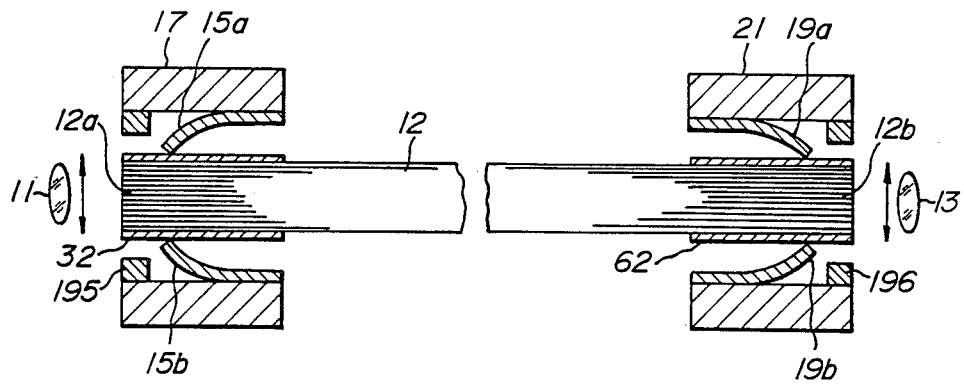

FIG_81
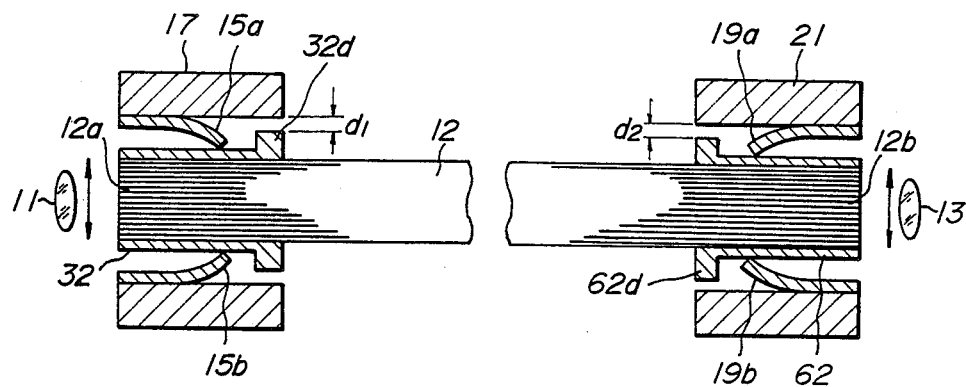
FIG_82
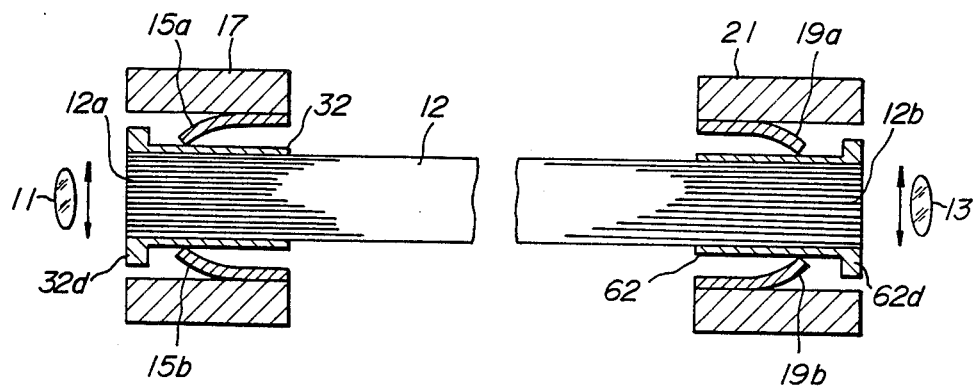

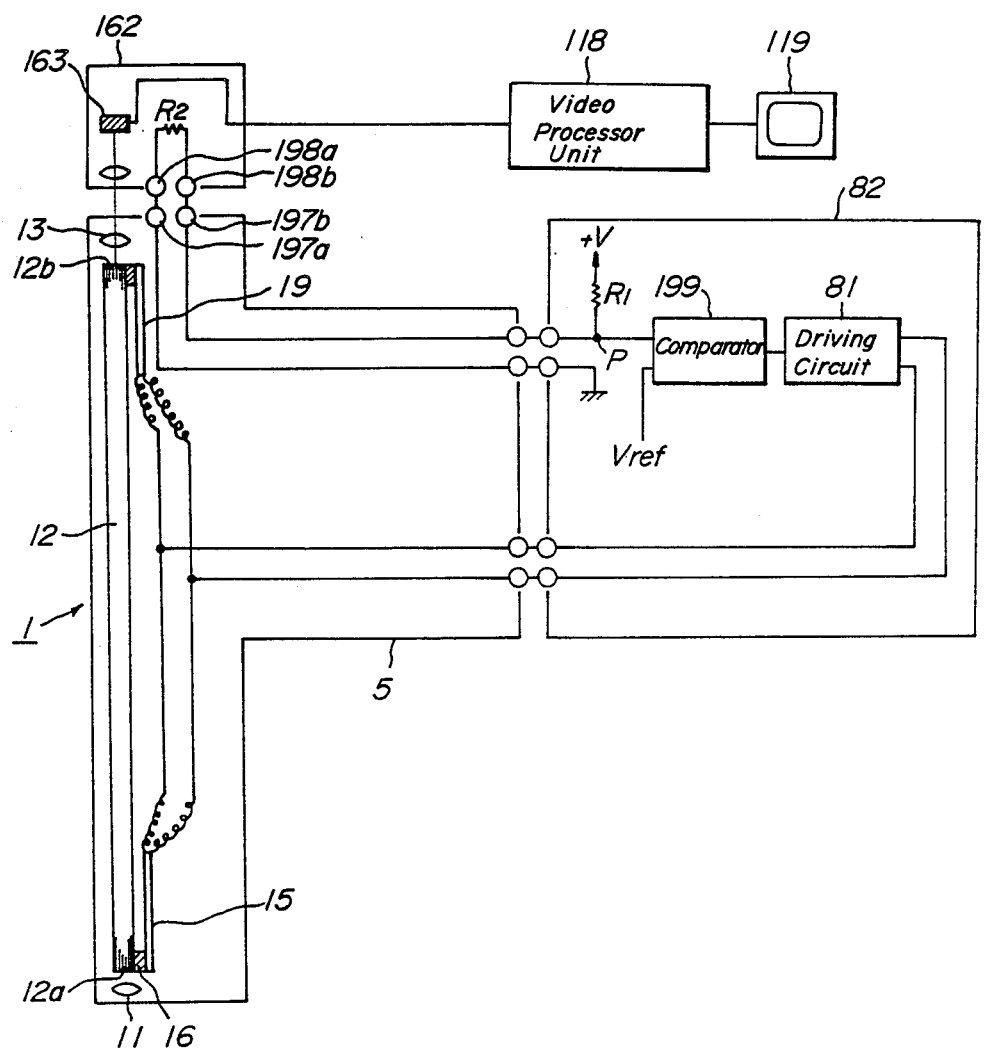
FIG_83

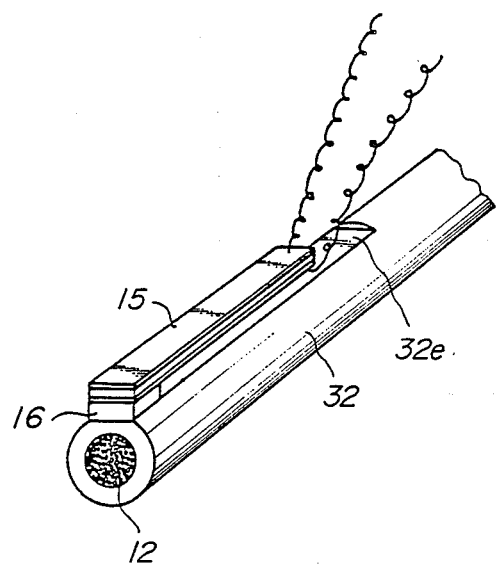
FIG_84

FIG_86
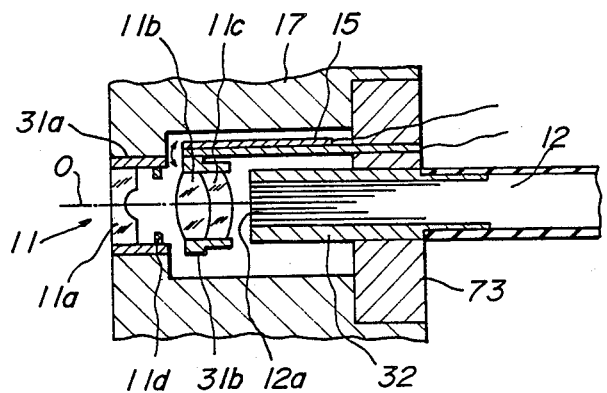
FIG_87
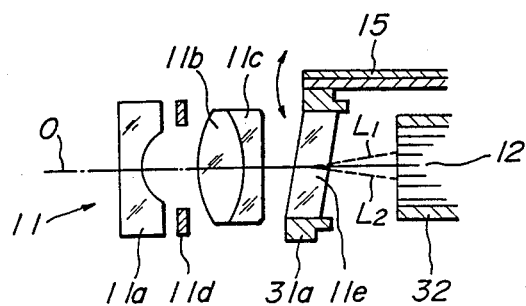

FIG_88
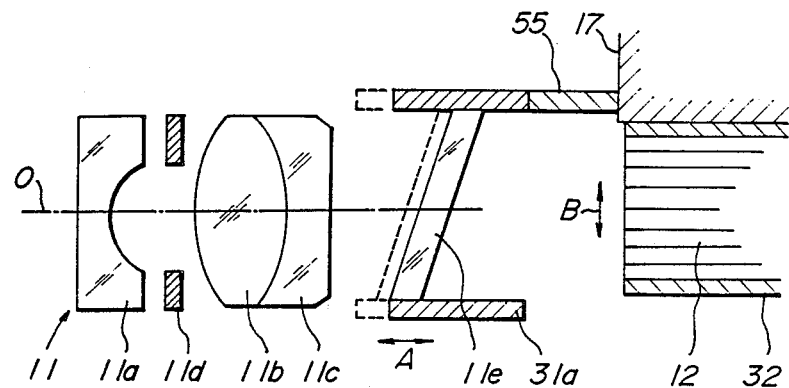
FIG_89
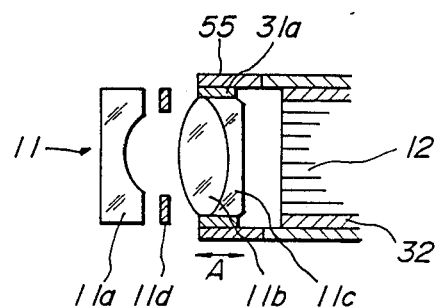

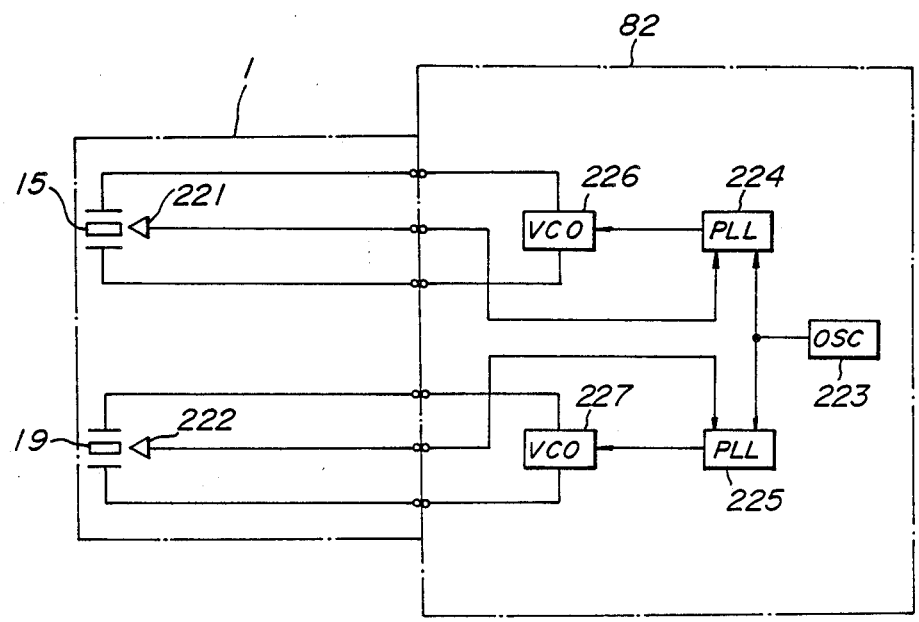
FIG_90

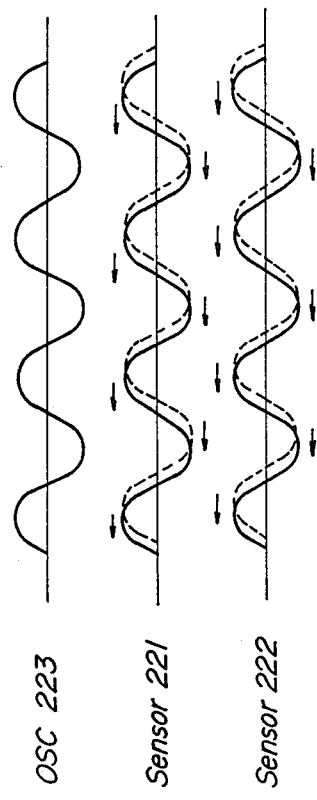
FIG_91A  OSC 223
FIG_91B  Sensor 221
FIG_91C  Sensor 222

FIG_92
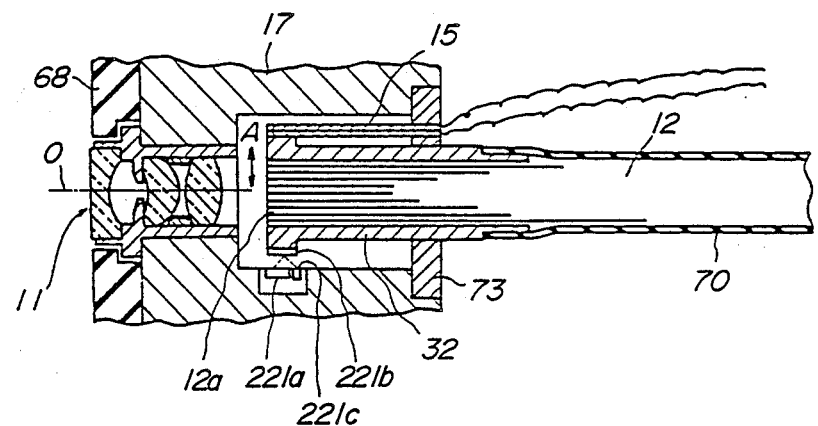
FIG_93
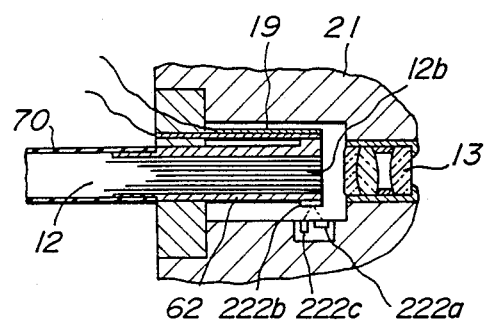

FIG_94
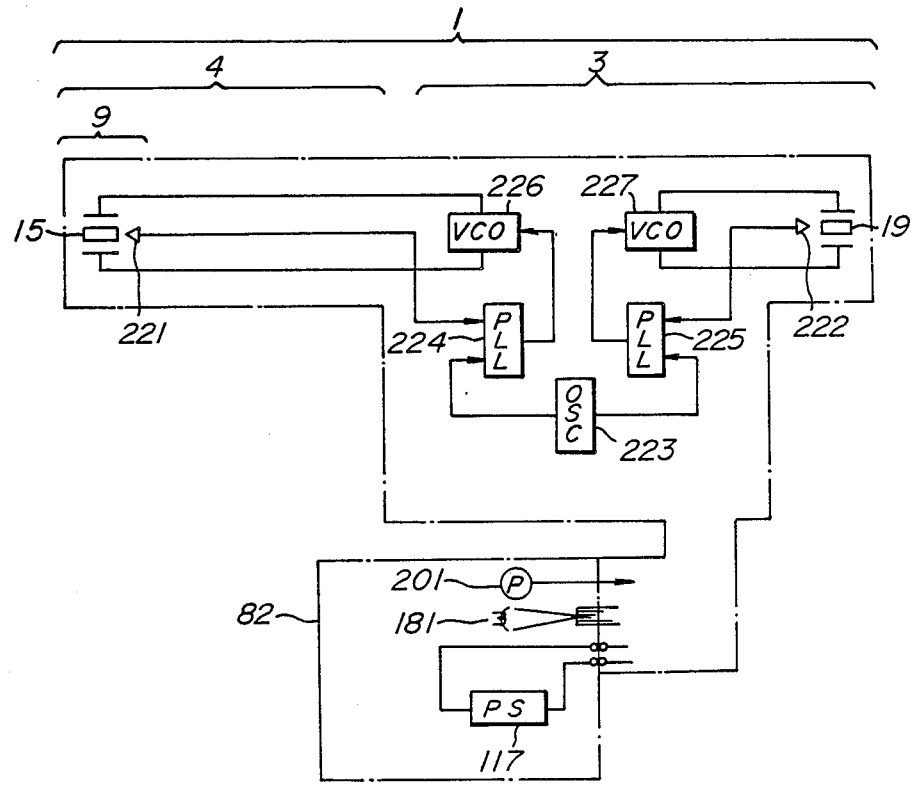

FIG_97
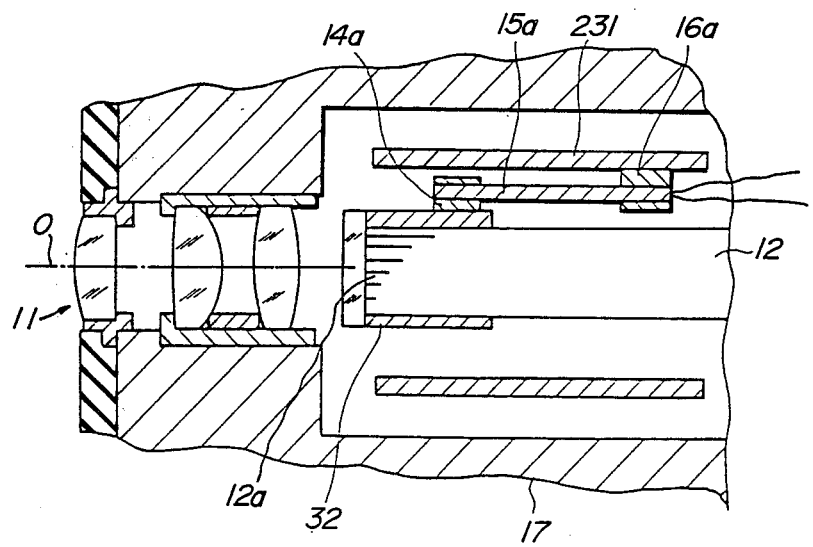
FIG_98
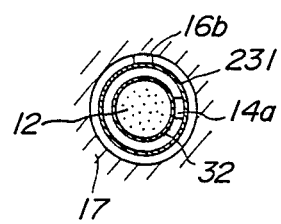

FIG_101
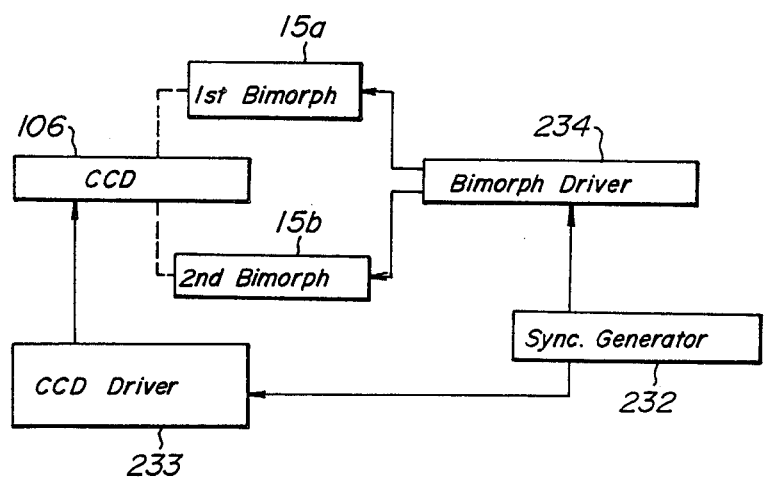
FIG_102A
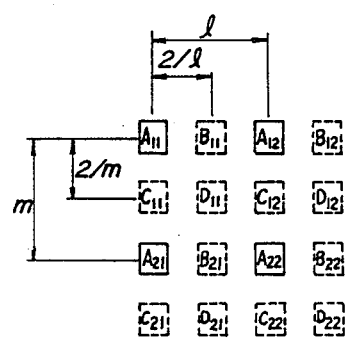
FIG_102B
FIG_102C
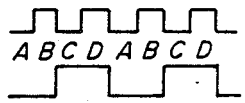

FIG_103
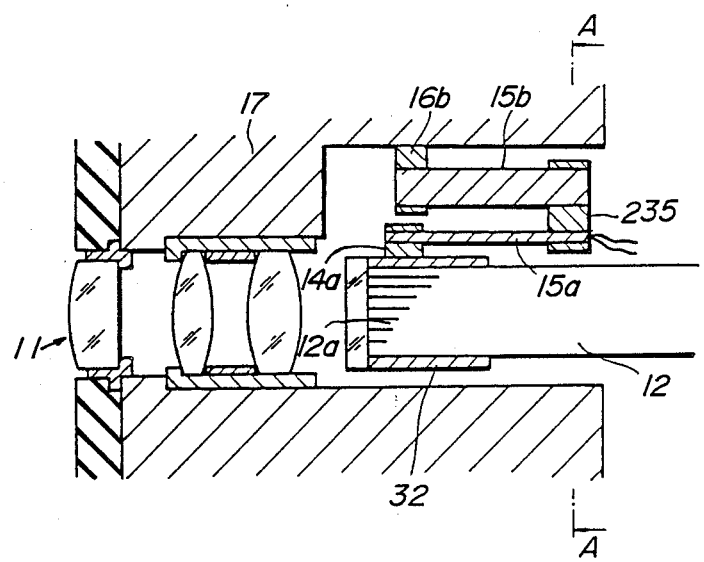
FIG_104
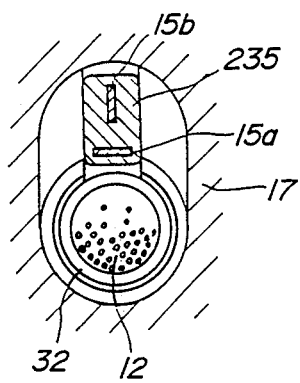

FIG_106
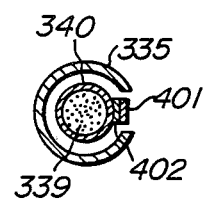
FIG_107
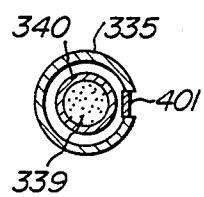

FIG_108
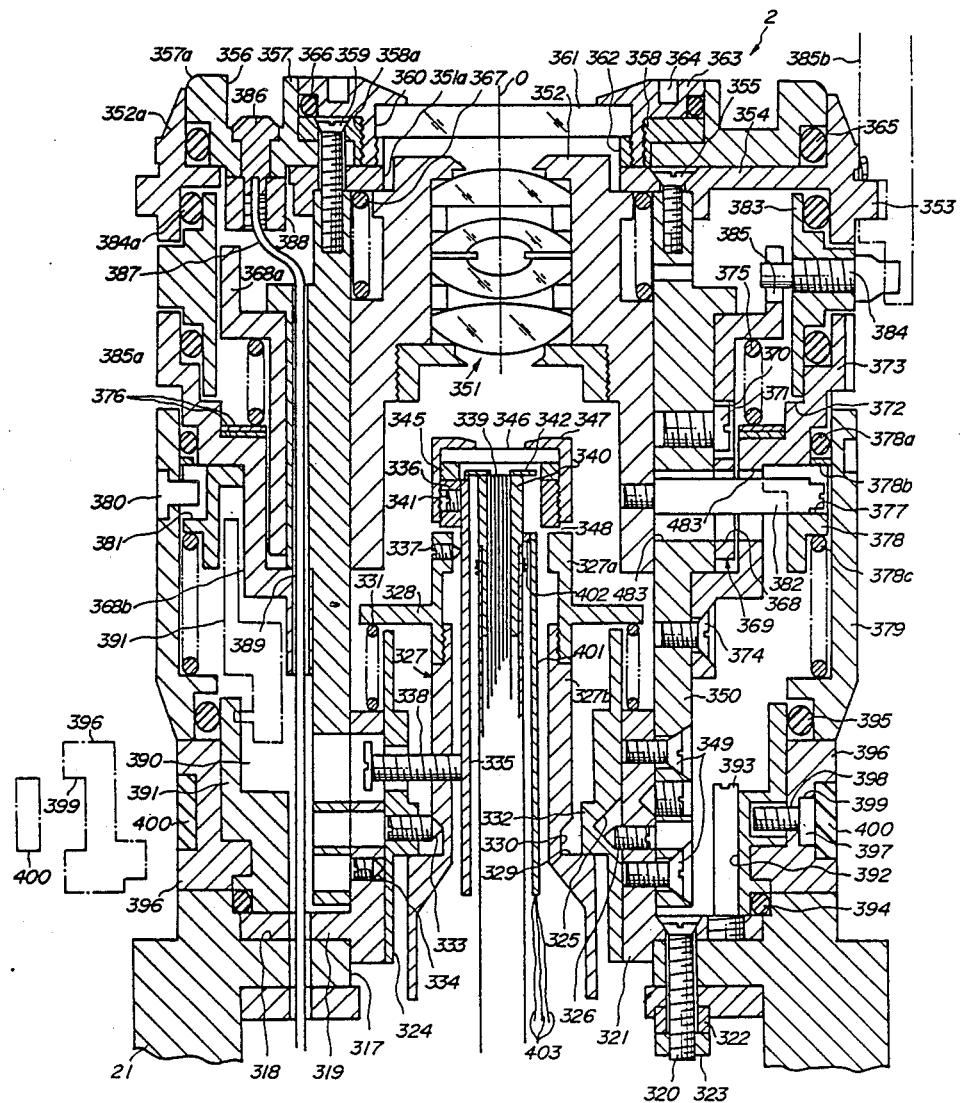

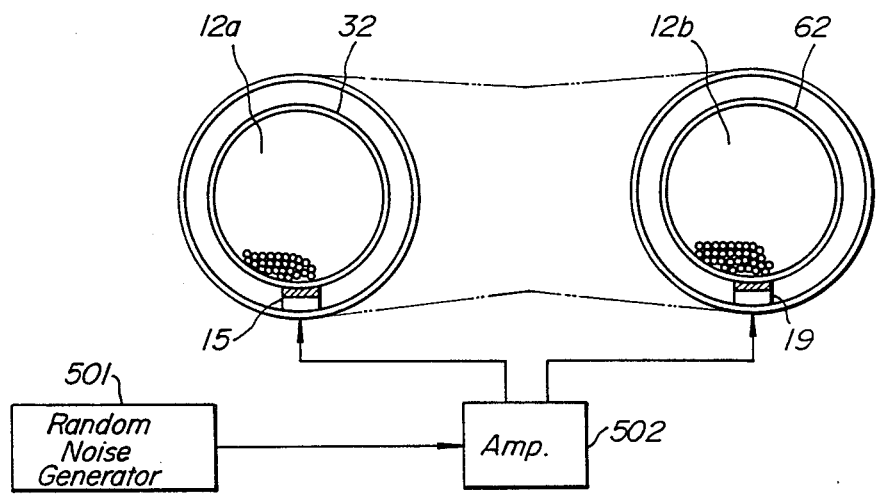
FIG_109

FIG_110
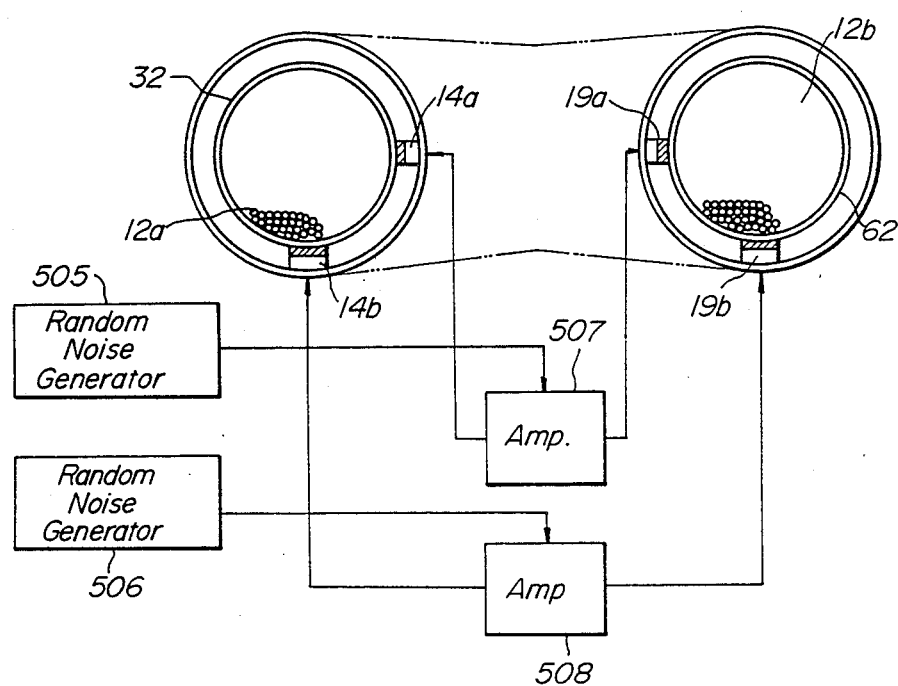

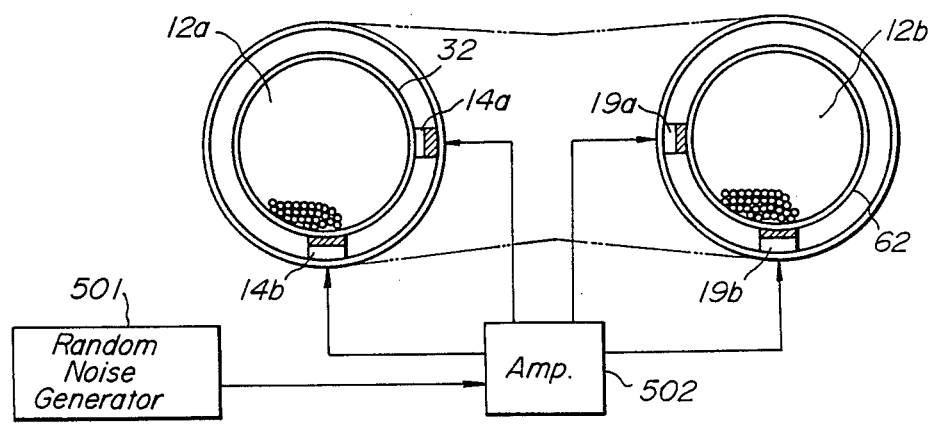
FIG_111

FIG_112
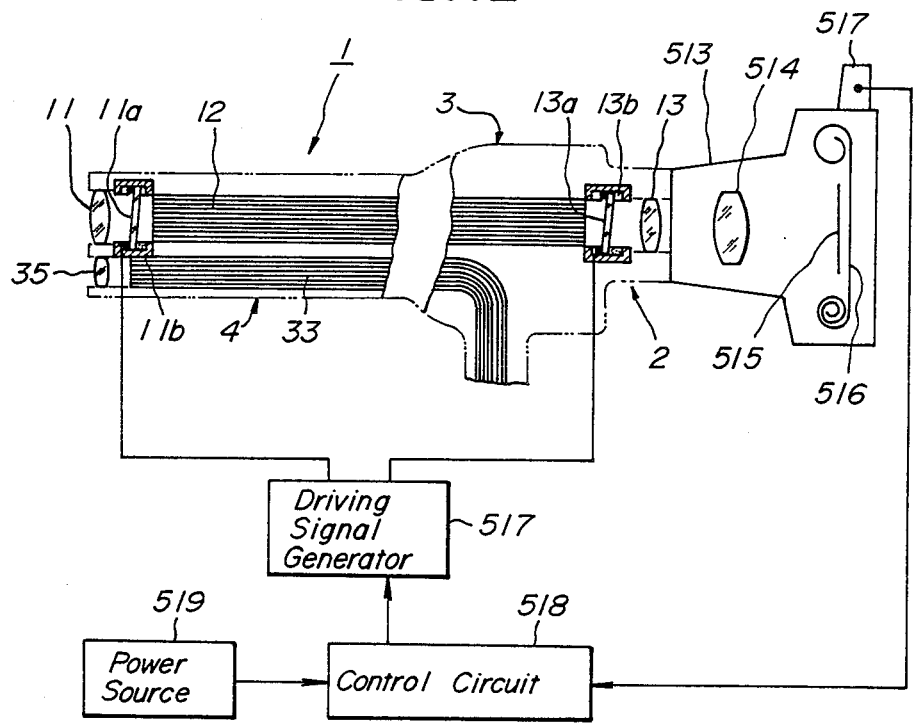
FIG_113
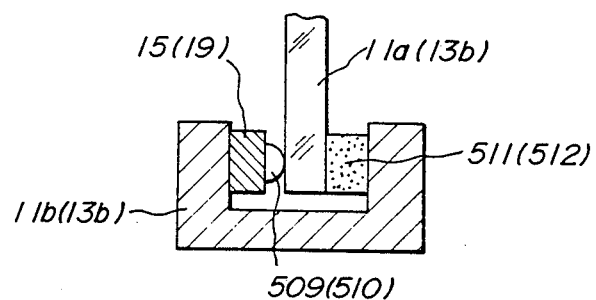

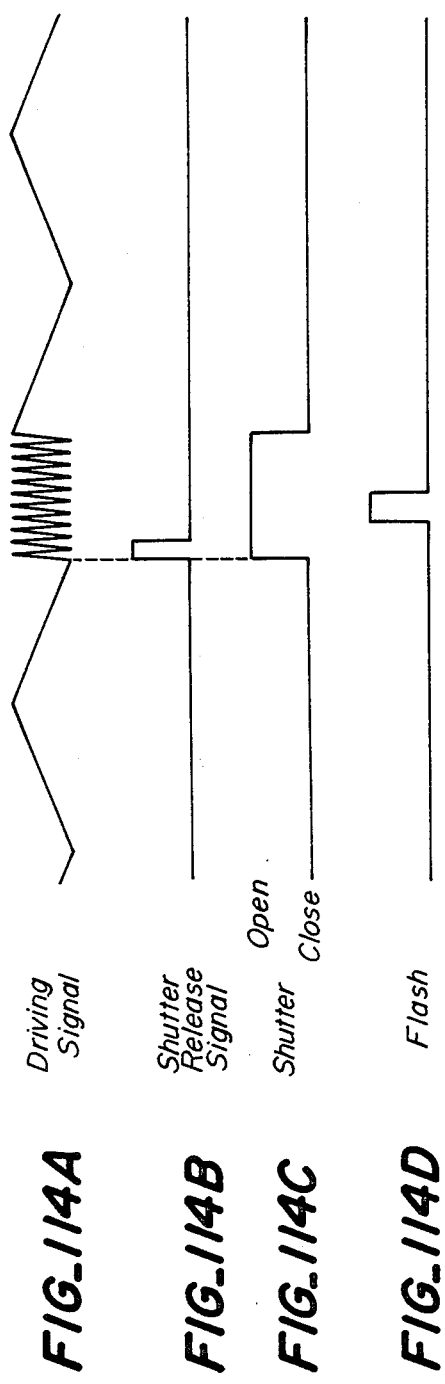

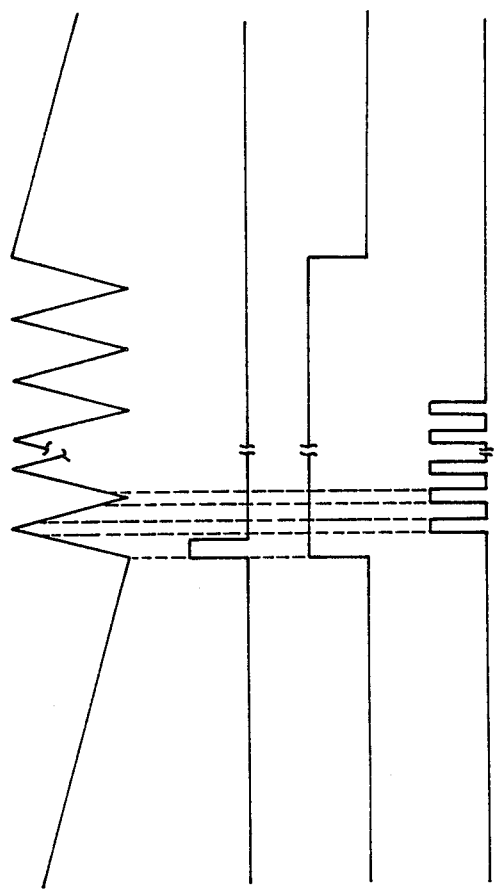

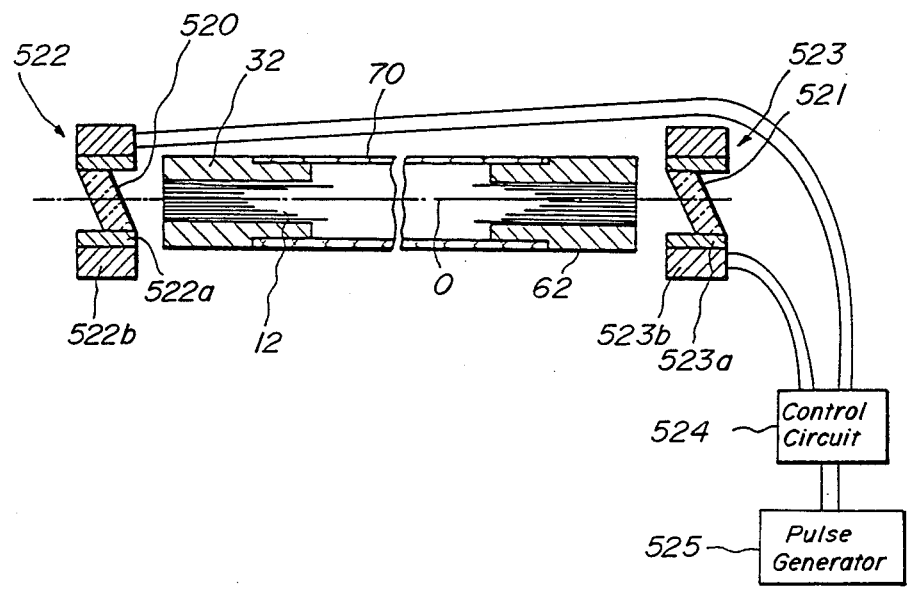
FIG_116

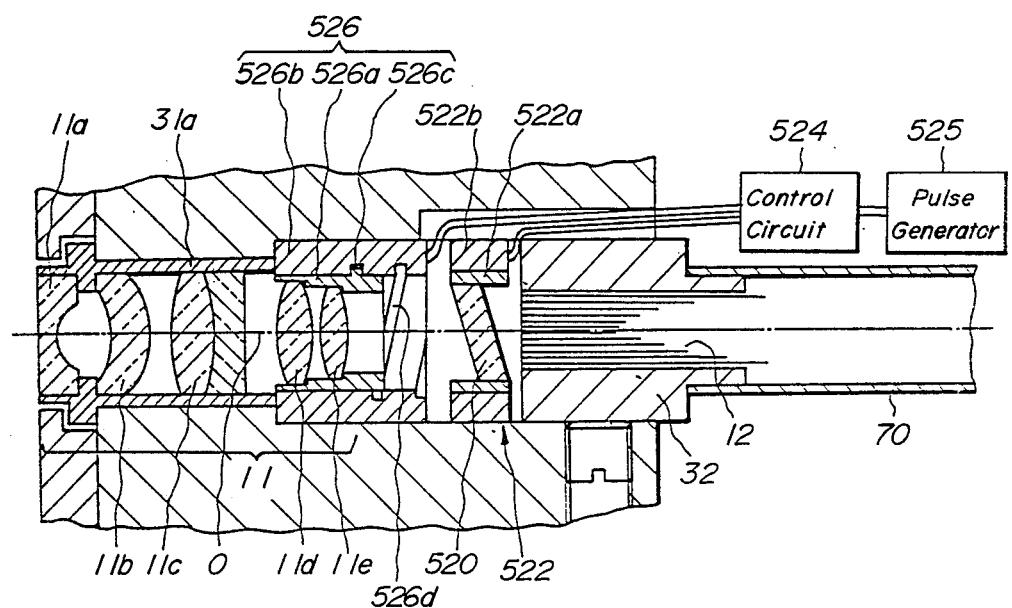
FIG_117

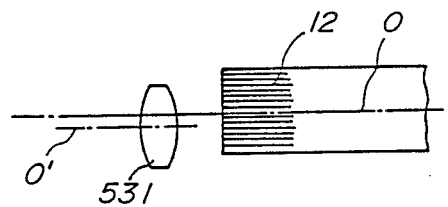
FIG_118A
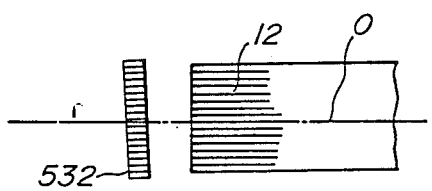
FIG_118B
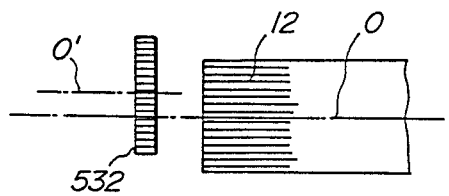
FIG_118C

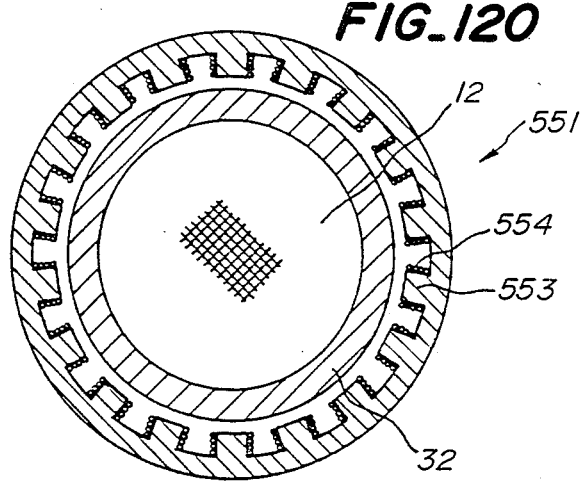
FIG_120
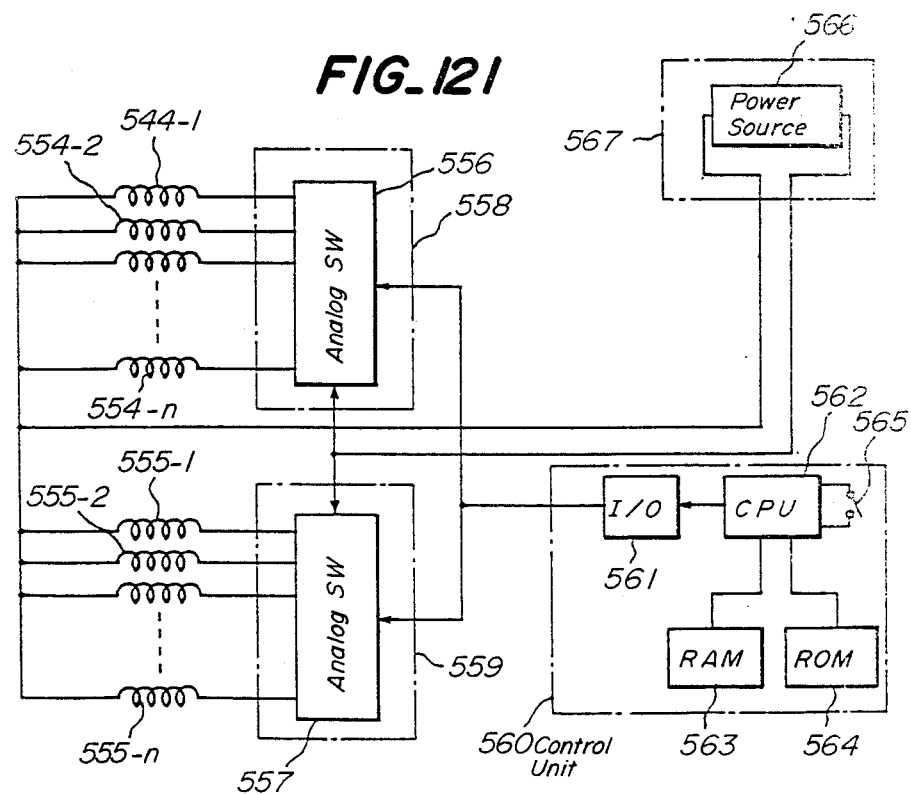
FIG_121

FIG_122
| | Enterance End | Exit End |
|---|---|---|
| Condition 1 | 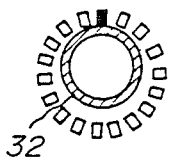 32 | 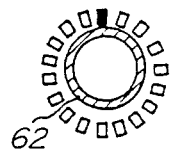 62 |
| Condition 2 | 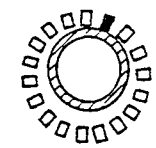 | 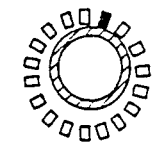 |
| Condition 3 | 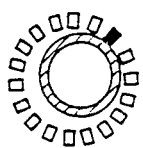 | 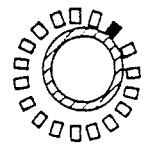 |
| Condition 4 | 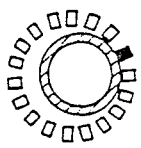 | 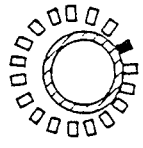 |
| ⋮ | ⋮ | ⋮ |

FIG_123
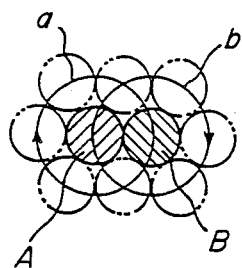
FIG_124
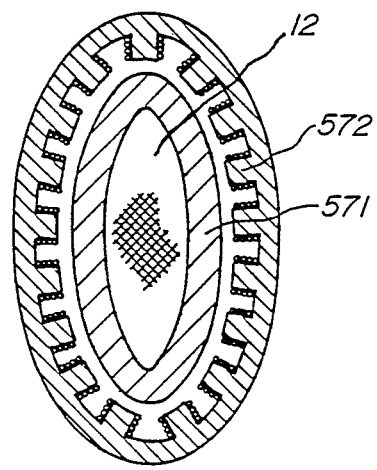
FIG_125
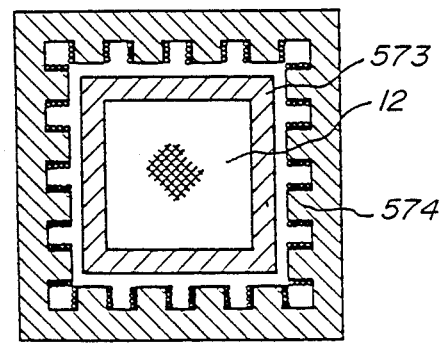

ENDOSCOPE APPARATUS

BACKGROUND OF THE INVENTION

Field of the Invention and Related Art Statement

The present invention generally relates to an endoscope apparatus for inspecting an inside of cavities of human bodies and pipes and others of mechanical constructions.

Heretofore, there have been proposed various kinds of endoscope apparatuses. Usually, the endoscope apparatus comprises an insertion section insertable into a cavity of a human body, a light guide for transmitting illumination light from a proximal end to a distal end of the insertion section, an objective lens system arranged at the distal end of the insertion section for forming an optical image of an illuminated object under inspection, and an image guide for transmitting the optical image from the distal end to the proximal end of the insertion section. The optical image transmitted through the image guide may be inspected with the naked eye by means of an eyepiece lens system or may be picked up by a television camera to derive an image signal which is supplied to a monitor to display the image of the object. In such an endoscope apparatus, the image guide is formed by a bundle of a number of optical fibers each of which is composed of a core and a clad applied around the core. Since the clad does not serve to transmit the light therethrough, the resolution of the fiber bundle is relatively low. Particularly, in the endoscope, since the insertion section should have the small diameter, the number of fibers of the image guide is limited and thus the resolution could not be made sufficiently high. Moreover, between adjacent fibers there is a binding layer which could not transmit the light, in the optical image transmitted through the image guide there appears a dark or black network-like mesh. This dark mesh is annoying particularly when the image is enlarged.

Further, in case of using the television camera having a solid state image sensor such as charge coupled device (CCD), photodiode image sensor, MOSFET image sensor and static induction transistor (SIT) image sensor, the resolution becomes further reduced, because the resolution of the solid state image sensor itself is low. Moreover, the solid state image sensor might produce undesired Moire fringes. There is further proposed a video endoscope apparatus in which a very small solid state image sensor is arranged in the distal end of the insertion section. In this video endoscope apparatus, there might be produced the Moire fringes when the object includes stripe patterns.

In order to avoid the above mentioned black network-like mesh, in U.S. Pat. No. 3,217,589, there is proposed an endoscope apparatus in which both ends of the image guide are supported rotatably and the image guide is rotated as a whole. However, in the endoscope for medical use, the insertion section has a small diameter, so that it is practically very difficult to arrange a driving mechanism for rotating the distal end of the image guide within the insertion section.

In U.S. Pat. No. 4,141,624, there is described an endoscope apparatus in which plane parallel plates are arranged between the objective lens system and the distal end of the image guide and between the proximal end of the image guide and the eyepiece lens system, respectively and these plane parallel plates are vibrated in the same direction viewed on the image in synchronism with each other. Mechanisms for vibrating the plates are formed by electromagnetic vibrating devices. In case of using the electromagnetic device, the diameter of the distal end portion of insertion section is liable to be large.

In German Gebranchsmuster Publication No. 7,315,025, there is further proposed an endoscope apparatus in which both ends of the image guide are vibrated by means of ultrasonic transducers arranged on respective ends of the image guide. However, in order to vibrate the image guide having a relatively large weight, it is necessary apply very large ultrasonic energy to the image guide so that the dimension of the ultrasonic vibrator becomes quite large, and thus the diameter of the insertion section might be large. Moreover, the ultrasonic vibration causes another problem of heat generation and the glass fibers composing the image guide might be broken by the high frequency ultrasonic energy.

In Japanese Patent Publication Kokai No. 58-168,015, there is described an endoscope apparatus in which piezo-electric vibrating elements are provided between the both ends of the image guide and supporting members so that the ends of the image guide are vibrated in a direction perpendicular to an optical axis of the image guide. The piezo-electric element is formed by a laminated piezo-electric element. In order to vibrate the image guide end by a sufficient amount, the laminated piezo-electric element has to be long, so that the insertion section is liable to have a long diameter.

In U.S. Pat. No. 4,618,884, there is disclosed still another endoscope apparatus in which the plane parallel plates are arranged in both ends of the insertion section like as the endoscope apparatus described in the above mentioned U.S. Pat. No. 4,141,624 and are tilted by means of piezo-electric elements. However, in this endoscope apparatus, the plane parallel plates could not be swung by a sufficiently large amount for effectively removing the black mesh, because the piezo-electric element is formed by a thickness vibration type element in order to swing the plate about a center axis extending perpendicularly to the optical axis of the image guide.

It should be noted that the above mentioned prior art publications do not teach how to remove the Moire fringes which are generated in the video endoscope apparatus comprising the solid state image sensor arranged in the distal end of the insertion section. It has been proposed to arrange filters such as spacial frequency filter and double refraction filter between the objective lens system and the solid state image sensor. However, this solution is expensive and further the dimension of the apparatus becomes complicated and large.

SUMMARY OF THE INVENTION

The present invention has for its object to provide a novel and improved endoscope apparatus in which the undesired black mesh can be removed effectively by means of the simple construction without increasing the diameter of the distal end of insertion section, so that the resolution of the observed image can be improved.

It is another object of the invention to provide an endoscope apparatus having the solid state image sensor, in which the undesired Moire fringes can be effectively removed by means of the simple and small construction.

It is still another object of the invention to provide an endoscope apparatus in which both the black mesh and Moire fringe can be removed by means of the simple construction without increasing the diameter of the insertion section.

According to the invention, an endoscope apparatus for inspecting an object comprises an insertion section insertable into the object under inspection and having a distal end and a proximal end;

an image guide arranged within the insertion section and having an entrance end arranged at the distal end of insertion section and an exit end arranged at the proximal end of insertion section;

an objective lens system arranged at the distal end of insertion section for forming an optical image of the object onto the entrance end of image guide;

an eyepiece lens system arranged at the proximal end of insertion section for projecting the optical image transmitted through the image guide onto an observating position;

a first driving means arranged at the distal end of insertion section and including at least one piezo-electric vibrating element which extends substantially in a longitudinal direction of the insertion section for causing a first vibrating movement of the optical image formed by the objective lens system and the entrance end of image guide relative to each other over a predetermined distance in a direction substantially perpendicular to an optical axis of the image guide; and a second driving means arranged at the proximal end of insertion section for causing a second vibrating movement of the optical image projected from the exit end of image guide and the eyepiece lens system relative to each other over said predetermined distance in the same direction as that of said first vibrating movement viewed on the optical image in synchronism with said first vibrating movement.

According to further aspect of the invention, an endoscope apparatus for inspecting an object comprises an insertion section insertable into the object under inspection and having a distal end and a proximal end;

an image guide arranged within the insertion section and having an entrance end arranged at the distal end of insertion section and an exit end arranged at the proximal end of insertion section;

an objective lens system arranged at the distal end of insertion section for forming an optical image of the object onto the entrance end of image guide;

an eyepiece lens system arranged at the proximal end of insertion section for projecting the optical image transmitted through the image guide onto an observating position;

a first driving means arranged at the distal end of insertion section and including at least one piezo-electric vibrating element which extends in a plane substantially perpendicular to an optical axis of the objective lens system and image guide for causing a first vibrating movement of the optical image formed by the objective lens system and the entrance end of image guide relative to each other over a predetermined distance in a direction substantially perpendicular to the optical axis of he image guide; and a second driving means arranged at the proximal end of insertion section for causing a second vibrating movement of the optical image projected from the exit end of image guide and the eyepiece lens system relative to each other over said predetermined distance in the same direction as that of said first vibrating movement viewed on the optical image in synchronism with said first vibrating movement.

According to another aspect of the invention, an endoscope apparatus for inspecting an object comprises an insertion section insertable into the object under inspection and having a distal end and a proximal end;

an image guide arranged within the insertion section and having an entrance end arranged at the distal end of insertion section and an exit end arranged at the proximal end of insertion section;

an objective lens system arranged at the distal end of insertion section for forming an optical image of the object onto the entrance end of image guide;

a first driving means arranged at the distal end of insertion section and including at least one piezo-electric vibrating element which is spirally wound in a direction of an optical axis of the objective lens system and image guide for causing a first vibrating movement of the optical image formed by the objective lens system and the entrance end of image guide relative to each other over a predetermined distance in a direction substantially perpendicular to the optical axis of the image guide; and a second driving means arranged at the proximal end of insertion section for causing a second vibrating movement of the optical image projected from the exit end of image guide and the eyepiece lens system relative to each other over said predetermined distance in the same direction as that of said first vibrating movement viewed on the optical image in synchronism with said first vibrating movement.

According to still another aspect of the invention an endoscope apparatus for inspecting an object comprises an insertion section insertable into the object under inspection and having a distal end and a proximal end;

an image guide arranged within the insertion section and having an entrance end arranged at the distal end of insertion section and an exit end arranged at the proximal end of insertion section;

an objective lens system arranged at the distal end of insertion section for forming an optical image of the object onto the entrance end of image guide;

an eyepiece lens system arranged at the proximal end of insertion section for projecting the optical image transmitted through the image guide onto an observating position;

a solid state image sensor arranged at the observating plane for picking-up the optical image of the object;

a first driving means arranged at the distal end of insertion section for causing a first vibrating movement of the optical image projected by the objective lens system and the entrance end of image guide relative to each other over a predetermined distance in a direction substantially perpendicular to the optical axis of the image guide; and a second driving means arranged at the proximal end of insertion section for causing a second vibrating movement of the optical image projected from the exit end of image guide and the solid state image sensor relative to each other over said predetermined distance in the same direction as that of said first vibrating movement viewed on the optical image in synchronism with said first vibrating movement.

In the above mentioned endoscope apparatuses according to the invention, there are provided the first and second driving means for causing the first and second vibrating movements, respectively, but according to another aspect of the invention, one of the first and second driving means may be deleted.

According to still another aspect of the invention, an endoscope apparatus for inspecting an object comprises an insertion section insertable into the object under inspection and having a distal end and a proximal end;

an objective lens system arranged at the distal end of insertion section for forming an optical image of the object onto the entrance end of image guide;

a solid state image sensor arranged in the distal end of insertion section for converting the optical image formed by the objective lens system; and a driving means arranged at the distal end of insertion section for causing a vibrating movement of the optical image formed by the objective lens system and the solid state image sensor relative to each other over a predetermined distance in a direction substantially perpendicular to the optical axis of the objective lens system.

BRIEF DESCRIPTION OF THE DRAWINGS

FIG. 1 is a perspective view showing an outer appearance of a first embodiment of the endoscope apparatus according to the invention;

FIG. 2 is a schematic view illustrating the internal construction of the endoscope shown in FIG. 1;

FIG. 3 is a schematic plan view depicting the core arrangement of the image guide;

FIG. 4 is a graph representing the driving voltage for the bimorph;

FIGS. 5 and 6 are schematic plan views illustrating the movement of the image guide;

FIG. 7 is a cross sectional view showing the detailed construction of the distal end of insertion section;

FIG. 8 is a cross sectional view depicting the distal end of a second embodiment of the endoscope apparatus according to the invention;

FIG. 9 is a cross sectional view illustrating the distal end of a third embodiment of the endoscope according to the invention;

FIG. 10 is a cross sectional view depicting the distal end of a fourth embodiment of the endoscope according to the invention;

FIG. 11 is a cross sectional view showing the distal end of a fifth embodiment of the endoscope according to the invention;

FIG. 12 is a cross sectional view illustrating the detailed construction of the distal end of a sixth embodiment of the endoscope according to the invention;

FIG. 13 is a cross sectional view depicting the detailed construction of the operation section of the endoscope shown in FIG. 12;

FIGS. 14A and 14B are graphs representing the driving voltages applied to the bimorphs illustrated in FIGS. 12 and 13;

FIG. 15 is a schematic plan view showing the movement of the image guide;

FIG. 16 is a schematic view representing the movement of the image guide in a modified embodiment of the endoscope shown in FIGS. 1 to 7;

FIG. 17 is a graph denoting the driving voltage for moving the image guide shown in FIG. 16 in the rectangular-step manner;

FIG. 18 is a schematic plan view showing the rectangular movement of the image guide;

FIG. 19 is a graph illustrating the waveform of the driving signal;

FIG. 20 is a graph representing the relationship between the applied voltage and the displacement of the bimorph;

FIG. 21 is a schematic plan view illustrating the movement of the image guide;

FIG. 22 is a cross sectional view showing the detailed construction of the distal end of insertion section of a seventh embodiment of the endoscope according to the invention;

FIGS. 23A and 23B are cross sectional views showing the construction of the distal end of insertion section of an eighth embodiment of the endoscope according to the invention;

FIGS. 24A and 24B are graphs representing the waveform of the driving voltages applied to the bimorphs shown in FIG. 23;

FIGS. 25A-25E are schematic views depicting the movement of the image guide;

FIGS. 26A and 26B are waveforms of the bimorph driving voltages;

FIGS. 27A-27E are schematic views representing the movement of the image guide;

FIGS. 28A and 28B are cross sectional views showing the construction of the distal end of insertion section of a ninth embodiment of the endoscope according to the invention;

FIGS. 29A and 29B are cross sectional views illustrating the detailed construction of the distal end of insertion section of a tenth embodiment of the endoscope according to the invention;

FIG. 30 is a cross sectional view showing the modified embodiment of the endoscope shown in FIG. 28;

FIGS. 32A, 32B and 32C illustrate still another embodiment of the driving voltage, movement of the image guide and brightness variation;

FIGS. 34A and 34B are cross sectional views illustrating the construction of the distal end of an eleventh embodiment of the endoscope according to the invention;

FIGS. 35 is a cross sectional view depicting a modification of the embodiment shown in FIGS. 34A and 34B;

FIGS. 36A and 36B are cross sectional views depicting the distal end of insertion section of a twelfth embodiment of the endoscope according to the invention;

FIG. 39 is a schematic cross sectional view showing the construction of a fourteenth embodiment of the endoscope apparatus according tot he invention;

FIG. 40 is a cross sectional view depicting a modification of the embodiment illustrated in FIG. 39;

FIG. 41 is a perspective view showing the guard pipe accommodating the exit end of image guide;

FIGS. 42A and 42B are cross sectional views representing the construction of the distal end of a fifteenth embodiment of the endoscope according to the invention;

FIG. 43 is a cross sectional view showing the construction of a sixteenth embodiment of the endoscope according to the invention;

FIG. 44 is a schematic view illustrating a seventeenth embodiment of the endoscope apparatus according to the invention;

FIG. 45 is a cross sectional view depicting the construction of the distal end of insertion section of an eighteenth embodiment of the endoscope according to the invention;

FIG. 46 is a cross sectional view showing the construction of the distal end of insertion section of a nineteenth embodiment of the endoscope according to the invention;

FIG. 48 is a cross sectional view showing the construction of the distal end of insertion section of a twenty first embodiment of the endoscope according to the invention;

FIG. 49 is a cross sectional view illustrating the construction of the distal end of insertion section of a twenty second embodiment of the endoscope according to the invention;

FIGS. 50A and 50B are perspective and cross sectional views, respectively depicting the construction of the distal end of insertion section of a twenty third embodiment of the endoscope according to the invention;

FIGS. 51A and 51B are perspective and cross sectional views, respectively showing the distal end of insertion section of a twenty fourth embodiment of the endoscope according to the invention;

FIGS. 52 and 53 are cross sectional views showing two modified embodiments of the bimorph of the endoscope according to the invention;

FIG. 54 is a cross sectional view depicting the construction of the distal end of insertion section of a twenty fifth embodiment of the endoscope according to the invention;

FIGS. 55A and 55B are perspective and cross sectional views, respectively showing the construction of the distal end of a twenty sixth embodiment of the endoscope according to the invention;

FIGS. 61A and 61B are cross sectional views depicting the construction of the distal end of a thirtieth embodiment of the endoscope according to the invention;

FIGS. 62, 63 and 64 are cross sectional views showing the construction of thirty first to thirty third embodiments of the endoscope according to the invention, in which the vibration movement is carried out only at the proximal end of insertion section;

FIGS. 67A and 67B are cross sectional views showing the construction of the distal end of insertion section of a thirty sixth embodiment of the video endoscope according to the invention;

FIG. 68 is a cross sectional view illustrating the construction of the distal end of insertion section of a thirty seventh embodiment of the video endoscope according to the invention;

FIG. 69 is a schematic view showing the whole construction of the endoscope apparatus shown in FIG. 68;

FIGS. 71A to 71E are signal waveforms for explaining the operation of the circuit illustrated in FIG. 70;

FIG. 72 is a schematic view showing the construction of a thirty ninth embodiment of the endoscope apparatus according to the invention;

FIGS. 73 and 74 are cross sectional views illustrating the construction of fortieth and forty first embodiments of the endoscope apparatus according to the invention, in which the vibration movement is effected at the distal end and the television camera attachment, respectively;

FIGS. 75 and 76 are schematic views showing the construction of forty second and forty third embodiments of the endoscope apparatus according to the invention, in which the bimorphs are driven with the aid of the insulating transformer;

FIG. 77 and 78A and 78B are cross sectional views depicting the construction of the distal end of insertion section of forty fourth embodiment of the
a endoscope apparatus according to the invention;

FIGS. 79, 80, 81 and 82 are cross sectional views showing the construction of a forty fifth embodiment and several modifications thereof of the endoscope apparatus, in which the amplitude of the vibration movement is limited;

FIG. 83 is a schematic view showing the construction of a forty sixth embodiment of the endoscope apparatus according to the invention;

FIG. 84 is a perspective view depicting the arrangement of the bimorph showing in FIG. 83;

FIG. 86 is a cross sectional view showing the construction of the distal end of insertion section of a forty eighth embodiment of the endoscope according to the invention;

FIG. 87 is a cross sectional view depicting the construction of the distal end of insertion section of a forty ninth embodiment of the endoscope according to the invention;

FIG. 88 is a cross sectional view illustrating a modification of the embodiment shown in FIG. 87;

FIG. 89 is a cross sectional view depicting the construction of the distal end of insertion section of a fiftieth embodiment of the endoscope according to the invention;

FIG. 90 is a schematic view illustrating the construction of a fifty first embodiment of the endoscope according to the invention;

FIGS. 91A to 91C are signal waveforms for explaining the operation of the endoscope showing FIG. 90;

FIGS. 92 and 93 are cross sectional views representing the construction of the distal end and proximal end of insertion section of the embodiment shown in FIG. 90;

FIG. 94 is a schematic view depicting a modification of the embodiment illustrated in FIG. 90;

FIGS. 96 and 97 are cross sectional views cut along lines A—A and B—B, respectively in FIG. 95;

FIG. 98 is a cross sectional view cut along a line C—C in FIG. 97;

FIG. 101 is a block diagram of the driving circuit for the endoscope shown in FIGS. 99 and 100;

FIGS. 102A-102C are schematic views for explaining the function of the endoscope illustrated in FIGS. 99 and 100;

FIG. 103 is a cross sectional view showing the construction of the distal end of insertion section of a fifty fourth embodiment of the endoscope according to the invention;

FIG. 104 is a cross sectional view cut along a line A—A in FIG. 102;

FIGS. 106 and 107 are cross sectional views cut along a line A—A and B—B, respectively in FIG. 105;

FIG. 108 is a cross sectional view showing the construction of the eyepiece section of a fifty sixth embodiment of the endoscope according to the invention;

FIGS. 109, 110 and 111 are schematic views showing a fifty seventh embodiment of the endoscope according to the invention, in which the bimorphs are driven in a random manner;

FIG. 112 is a schematic view depicting the construction of a fifty eighth embodiment of the endoscope according to the invention;

FIG. 113 is a cross sectional view illustrating the construction of the distal end of endoscope shown in FIG. 112;

FIGS. 114A-114D and 115A-115D are signal waveforms for explaining the operation of the endoscope of FIG. 112;

FIG. 116 is a schematic view showing the construction of a fifty ninth embodiment of the endoscope according to the invention;

FIG. 117 is a cross sectional view depicting the distal end of a modification of the embodiment shown in FIG. 116;

FIGS. 118A-118C are cross sectional views showing several embodiments of the optical element by means of which the image shift is effected;

FIG. 120 is a cross sectional view cut along a line A—A in FIG. 119;

FIG. 121 is a block diagram showing the control circuit;

FIG. 122 is a schematic view illustrating the manner of revolution of the image guide;

FIG. 123 is a schematic plan view representing the movement of optical fibers; and FIGS. 124 and 125 are cross sectional views illustrating other embodiments of the electromagnetic unit.

EXPLANATION OF THE PREFERRED EMBODIMENTS

Figure 31A:
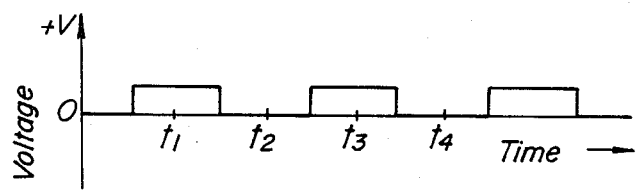
FIGS. 31A, 31B and 31C show another embodiment of the driving voltage, movement of image guide and brightness variation.

FIGS. 1 to 7 show a first embodiment of the endoscope apparatus according to the invention. FIG. 1 is a perspective view showing an outer appearance of an endoscope 1 of the endoscope apparatus. The endoscope 1 comprises an eyepiece section 2, operation section 3, insertion section 4, universal code 5 and connector 6. The eyepiece section 2 comprises an eyepiece lens system, and the operation section 3 includes a handle 3a for moving a distal end 9 of the insertion section 4. To this end, the insertion section 4 comprises a bending portion 8. Within the operation section 3 and insertion section 4, there is arranged an image guide whose proximal end is faced to the eyepiece lens system. A light guide is inserted within the insertion section 4, operation section 3 and universal code 5 and the proximal end of the light guide is projected beyond the connector 6. When the connector 6 is coupled with a socket provided on a light source unit not shown, the proximal end of light guide is faced to a light source lamp. Then, illumination light emitted by the lamp is made incident upon the proximal end of light guide and is transmitted through the light guide to illuminate the object under inspection. An optical image of the illuminated object is formed by an objective lens system arranged in the distal end of insertion section 4 and is transmitted through the image guide to the eyepiece section 2. Therefore, the image of the object can be observed by means of the eyepiece lens system.

FIG. 2 is a schematic view illustrating the internal construction of the endoscope 1. The endoscope 1 includes objective lens system 11, light guide 12 composed of an optical fiber bundle, and eyepiece lens system 13. The objective lens system 11 forms the optical image of the object under inspection on an entrance end surface of a distal end 12a of light guide 12. The image is transmitted through the image guide 12 and is formed on an exit end surface of a proximal end 12b of light guide. This image is observed by an eye with the aid of the eyepiece lens system 13 provided in the eyepiece section 2. In the present embodiment, in the distal end portion 9 of insertion section 4 there is arranged a first elongated piezo-electric bimorph 15 which extends substantially in a longitudinal direction of the insertion section 4. One end 15A of bimorph 15 is secured via a spacer 14 to the distal end 12a of image guide 12 and the other end 15B of bimorph is secured via a spacer 16 to a hard tip member 17 constituting the distal end portion 9 of insertion section 4. Usually the hard tip member 17 is made of a cylinder-like metal block having a plurality of openings through which the light guide, image guide, air and water supply and discharge tubes, forceps channel, etc. are extended. It should be noted that the strip-like bimorph 15 extends in parallel with an optical axis O of the objective lens system 11 and image guide 12. Similarly, in the operation section 3, there is arranged a second elongated piezo-electric bimorph 19 whose one end is secured by means of a spacer 18 to the proximal end 12b of image guide 12 and whose other end is secured via a spacer 20 to a hard member 21 constituting the operation section 3. The second bimorph 19 also extends in parallel with the optical axis O of the image guide 12 and eyepiece lens system 13. Two terminals of the first bimorph 15 are connected to a first driving circuit 24 by means of conductors 22a, 22b and two terminals of the second bimorph 19 are connected to a second driving circuit 25 via conductors 23a, 23b. The first and second driving circuits 24 and 25 are commonly connected to a signal generator 26.

FIG. 3 is a schematic plan view showing the arrangement of optical fiber cores a at the entrance and exit end surfaces of the image guide 12. Each core is surrounded by a clad having a lower refractive index than that of the core and a number of optical fibers are bound with each other with the aid of a binding layer. In FIG. 3 the clad and binding layer are not shown for the sake of clearness. As illustrated in FIG. 3, the cores are not packed densely, and thus the image transmitted through the image guide 12 has a low resolution. Further, when the image transmitted through the image guide is inspected, the annoying black mesh is visible. Particularly, when the image is expanded, the black mesh becomes eyesore to a large extent.

In the present embodiment, a rectangular driving voltage shown in FIG. 4 is applied to the piezo-electric bimorphs 15 and 19 by means of the driving circuit 24 and 25 and conductors 22a, 22b and 23a, 23b, respectively, and then the bimorphs are vibrated in the direction perpendicular to the longitudinal direction, i.e. the optical direction 0. Since the driving circuits 24 and 25 are commonly energized by the signal generator 26 in synchronism with each other, the distal end 12a and proximal end 12b of image guide 12 are vibrated in synchronism with each other. In this case, the vibration directions of these ends of image guide have to be identical with each other viewed on the image. Further, the amplitude $V_1$ of the driving signal shown in FIG. 4 is set such that the amount of displacement of the ends of image guide becomes substantially equal to a half of a distance P between successive cores a.

In the present invention, a fundamental frequency, i.e. a repetition frequency of the driving signal has to be set at most equal to the highest audible frequency. It should be noted that the vibration is preferably invisible in order to remove the annoying flicker. To this end, the fundamental frequency is higher than 10 Hz, preferably higher than 30 Hz. If the ends of image guide are vibrated at a frequency higher than the highest audible frequency, fibers consisting of the image guide might be broken or damaged. Moreover, the high frequency vibration will produce heat which might affect the optical elements together with the heat generated by the piezo-electric bimorphs.

Now it is assumed that the end of image guide is vibrated in a direction shown by an arrow I in FIG. 3, then the image guide is moved between cores a and b as illustrated in FIG. 5, so that the resolution in the horizontal direction I can be increased substantially by two. Since both the ends of image guide are vibrated in the same direction in synchronism with each other, the image viewed through the image guide does not move. When the end of image guide is vibrated in a direction II in FIG. 3 which is inclined to the horizontal direction substantially by 45°, the image guide moves between obliquely aligned cores a and b, so that the resolution can be improved not only in the horizontal direction, but also in the vertical direction.

FIG. 7 is a cross sectional view illustrating the detailed construction of the distal end 9 of the insertion section 4. The objective lens system 11 is held by a cylinder 31 which is fixed to the hard tip member 17 constituting the distal end of insertion section. Onto the distal end 12a of image guide 12 there is clamped a guard pipe 32. The piezo-electric bimorph 15 is arranged within a narrow space formed between the hard tip member 17 and the guard pipe 32 and is extended in the elongated direction of the insertion section 4. Therefore, the diameter of the insertion section is not made large and further the bimorph 15 can have a longer length, and the distal end 12a of image guide 12 can be vibrated by a desired amount. Along the image guide 12 there is further arranged a light guide 33 for transmitting the illumination light, and a concave lens 35 held by a cylinder 34 is arranged at the exit end of light guide 33. The distal end of light guide 33 is covered with a guard pipe 38. There is further provided a bending mechanism 36 for bending the distal end 9 of insertion section 4 into a desired direction by operating the handle 3a on the operation section 3. The hard tip member 17 and bending mechanism 36 are covered with an outer tube 37 made of rubber.

In the first embodiment so far explained, the two bimorphs 15 and 19 are driven by the separate driving circuits 24 and 25, respectively, but when these bimorphs have the same construction, it is possible to drive them by means of a single driving circuit. Further, in the present embodiment, the proximal end 12b of image guide 12 is vibrated by the elongated bimorph 19 which extends in the optical axis O. However, since the proximal end 12b of image guide 12 is out of the insertion section 4 and is arranged in the operation section 3 which is not inserted into the object under inspection and there can be obtained a rather large space for accommodating the bimorph, it is possible to provide a large bimorph. For instance, a bimorph of lamination type may be arranged in the direction perpendicular to the optical axis O of the image guide 12. In this case, the distal end 12b of image guide 12 may be vibrated in the direction precisely perpendicular to the optical axis O, and the distance between the exit surface of image guide and the eyepiece lens system does not fluctuate at all. Therefore, the focusing condition could not be varied and the image can be observed more clearly. This can mitigate the fatigue of the eye of user. Moreover, the focal depth of the eyepiece lens system can be made smaller, so that the eyepiece lens system having a larger numerical aperture can be used.

FIG. 8 is a cross sectional view showing the detailed construction of the distal end of insertion section of a second embodiment of the endoscope apparatus according to the invention. It should be noted that throughout the drawings portions similar to those shown in FIGS. 1-7 are denoted by the same reference numerals as far as possible, and the explanation of similar portions will be omitted to such an extend that the construction could be understood clearly without the detailed explanation. Further, the construction of the driving means at the distal end of insertion section may be equally used as the driving means at the proximal end of insertion section, but in order to avoid the superfluity only one of them will be explained in some of the following embodiments.

In the embodiment shown in FIG. 8, instead of the image guide 12 the objective lens system 11 is vibrated. To this end, the distal end 12b of image guide 12 is secured to the hard tip member 17 by means of an arm 17a, and the cylinder 31 accommodating the objective lens system 11 is connected via the spacer 14 to one end of the piezo-electric bimorph 15 and the other end of the bimorph is secured via the spacer 16 to the hard tip member 17. In front of the objective lens system 11, a cover glass plate 39 is secured to the hard tip member 17 in a liquid tight manner.

When the driving voltage is applied via the conductors 22a, 22b to the piezo-electric bimorph 15, the bimorph is bent and the objective lens system 11 is vibrated in a direction substantially perpendicular to the optical axis O, e.g. in the horizontal direction. In the present embodiment, since the bimorph 15 is extended up to the objective lens 11, the length of the bimorph can be made longer than the previous embodiment, so that the amplitude of the driving voltage may be decreased. This is quite advantageous for the medical endoscope which requires the high safety. Moreover, the weight of the cylinder 31 is reduced as compared with the previous embodiment and the load to the bimorph is decreased, so that the lens can be vibrated easily at a high frequency.

FIG. 9 is a cross sectional view depicting the detailed construction of the distal end of a third embodiment of the endoscope according to the invention. In the present embodiment, both the objective lens system 11 and the distal end 12a of image guide 12 are vibrated in opposite directions. For this purpose, in addition to the second embodiment shown in FIG: 8 there is further provided a piezo-electric bimorph 41 whose one end is secured via a spacer 42 to the front end of guard pipe 32 accommodating the distal end 12a of image guide 12, the other end of bimorph being secured via a spacer 43 to the hard tip member 17. The terminals provided on the bimorph 41 are connected via conductors 43b and 43a to the opposite polarity terminals on the bimorph 15 to which the conductors 22a and 22b are connected, respectively.

When the driving signal is applied to the bimorphs 15 and 41 via the conductors 22a, 22b and 43a, 43b, the two bimorphs are bent in opposite directions in synchronism with each other. Therefore, the amplitude of the driving signal can be reduced, which is advantageous in the view point of safety. In the present embodiment, the bimorphs 15 and 41 are connected to the common driving circuit in parallel with each other, but they may be connected to separate driving circuits.

FIG. 10 is a cross sectional views showing the detailed construction of the distal end of a fourth embodiment of the endoscope according to the invention. In the present embodiment, the image guide 12 is fixed to the hard tip member 17 and the objective lens system 11 is vibrated by means of the bimorph 15. To the cylinder 31 accommodating the objective lens system 11 there is secured a projection 45 which is journaled to an arm 17b secured to the hard tip member 17 with the aid of a shaft 46. At a free end of the bimorph 15 there is secured an operation chip 47 made of hard insulating material such as ceramics and the operation chip is urged against the cylinder 31. Between the cylinder 31 and the hard tip member 17 there is arranged a compressed coil spring 48 to bias the cylinder to rotate in the clockwise direction about the shaft 46. The remaining construction is similar to the previous embodiments.

When the driving signal is applied to the bimorph 15 via the conductors 22a and 22b, the bimorph is bent in the clockwise direction about the spacer 16 so that the objective lens system 11 is rotated in the counterclockwise direction about the shaft 46 against the force of the coil spring 48. Therefore, the direction of the principal light ray in a light flux focused by the objective lens system onto the entrance surface of image guide 12 is changed, and thus the position of the optical image formed on the entrance end surface of image guide 12 is moved leftward in FIG. 10. When the driving voltage becomes zero, the objective lens system 11 is returned into the initial position due to the force of the coil spring 48. By repeating this operation, the same effect as that of the previous embodiments can be attained. It should be noted that in the present embodiment, the objective lens system 11 is moved in the direction substantially perpendicular to the optical axis and at the same time, the objective lens system is tilted. When the objective lens system 11 is tilted, a half of the image formed on the entrance surface of image guide 12 is defocused, but the tilting angle is very small, so that the defocused could be practically ignored.

FIG. 11 is a cross sectional view showing the detailed construction of the distal end of a fifth embodiment of the endoscope according to the invention. In the present embodiment, the entrance end 12a of image guide 12 is vibrated with the aid of a laminated type piezo-electric element. To the guard pipe 32 accommodating the entrance end 12a of image guide 12 is secured a projection 51 which is journaled by means of a shaft 52 to an arm 17c formed integrally with the hard tip member 17. A compressed coil spring 53 is arranged between the hard tip member 17 and the guard pipe 32 to bias the pipe such that the entrance end 12a of image guide 12 is rotated in the counter-clockwise direction about the shaft 52. At the front end of guard pipe 32 there is provided a lag 54 and the hard tip member 17 further has an arm 17d formed integrally therewith. One end of a laminated type piezo-electric element 55 is secured to the arm 17d, and to the other end of piezo-electric element is secured an operation tip 56 made of hard insulating material, e.g. ceramics. The laminated piezo-electric element 55 has an elongated shape and is extended along the longitudinal axis of the insertion section.

When the driving voltage is applied to the piezo-electric element 55 via the conductors 22a, 22b, the element expands in its longitudinal direction, so that the entrance end 12a of image guide 12 is rotated in the clockwise direction about the shaft 52 against the force of the coil spring 53. When the driving voltage becomes zero, the length of the element 55 is reduced and the entrance end 12a of image guide 12 is rotated in the counter-clockwise direction due to the force of the coil spring 53.

Also in this fifth embodiment, the entrance end 12a of image guide 12 is slightly tilted, but the defocus due to this tilting motion is very small and can be ignored.

The amount of expansion of the laminated type piezo-electric element 55 is substantially proportional to the length. Since the elongated element 55 is arranged in the optical axis direction, it is possible to attain a sufficiently large amount of displacement under the low driving voltage, which improves the safety for the medical endoscope.

FIG. 12 is a cross sectional view showing the construction of the distal end of a sixth embodiment of the endoscope according to the invention. In this embodiment, the objective lens 11 and the entrance end 12a of image guide 12 are vibrated in mutually orthogonal directions, for instance, in the horizontal and vertical directions, respectively. The cylinder 31 accommodating the objective lens system 11 is connected via the spacer 14a to one end of a first piezo-electric bimorph 15a whose other end is secured by means of the spacer 16a to the hard tip member 17. The first bimorph 15a is connected to the driving circuit via the conductors 22a and 22b. The guard pipe 32 accommodating the entrance end 12a of image guide 12 is secured via the spacer 14b to one end of a second piezo-electric bimorph 15b whose other end is secured by means of the spacer 16b to the hard tip member 17. The second bimorph 15b is connected to a second driving circuit by means of conductors 22c and 22d.

When the driving voltage is applied to the first bimorph 15a, the objective lens system 11 is vibrated in the horizontal direction and when the driving signal is applied to the second bimorph 15b, the entrance end 12a of image guide 12 is vibrated in the vertical direction, so that the resolution can be improved both in the horizontal and vertical directions. It should be noted that the terms, "horizontal" and "vertical" are not used to intend to denote the directions in the drawings, but are used to indicate the directions on the image. In the present embodiment, the first and second bimorphs 15a and 15b are driven by the separate driving circuits, but they may be driven by the common driving circuit.

FIG. 13 is a cross sectional view showing the detailed construction of the operation section of the sixth embodiment of the endoscope according to the invention. In this embodiment, the eyepiece lens system 13 and the exit end 12b of image guide 12 are vibrated in the horizontal and vertical directions, respectively. To this end, a cylinder 51 accommodating the eyepiece lens system 13 is connected via a spacer 18a to one end of a first piezo-electric bimorph 19a whose other end is secured via a spacer 20a to the hard member 21 such as a housing of the operation section 3. A guard pipe 62 accommodating the exit end 12b of image guide 12 is connected by means of a spacer 18b to one end of a second piezo-electric bimorph 19b whose other end is secured via a spacer 20b to the hard member 21. The first and second bimorphs 19a and 19b are connected to respective driving circuits by means of conductors 23a, 23b and 23c, 23d, respectively. In opposition to the eyepiece lens system 13 there is arranged a glass plate 63.

When the driving voltage synchronized with the driving voltage applied to the bimorph 15a for vibrating the objective lens system 11 in the horizontal direction is applied to the first bimorph 19a, the eyepiece lens system 13 is vibrated in the horizontal direction, and by applying to the second bimorph 19b the driving voltage synchronized with the driving voltage applied to the bimorph 15b for driving the entrance end 12a of image guide 12 in the vertical direction, the exist end 12b of image guide 12 is vibrated in the vertical direction.

FIGS. 14A and 14B are graphs showing the driving voltages $V_1$ and $V_2$ applied to the bimorphs 15a, 19a and 15b, 19b, respectively, and FIG. 15 is a plan view showing the movement of cores of the image guide 12. During a time interval $t_0$-$t_1$, the driving voltages $V_1$ and $V_2$ are zero, the image guide 12 is situated at a position denoted by cores a. For a time interval $t_1$-$t_2$, only the driving voltage $V_1$ applied to the first bimorphs 15a and 19a is in a high level, so that the image guide 12 is moved horizontally into a position denoted by cores b.

During a next time interval $t_2$-$t_3$, the driving voltage $V_2$ for the second bimorphs 15b and 19b is also in the high level, the image guide is shifted in the vertical direction as shown by cores c. In a time period $t_3$-$t_0$, only the voltage $V_1$ becomes zero, so that the image guide is moved horizontally into a position represented by cores d. During the time interval $t_0$-$t_1$, both the voltages $V_1$ and $V_2$ become zero, and therefore the image guide is shifted upward in the vertical direction into the initial position defined by the core a. In this manner, all the cores of the image guide are moved in a square-step manner a→b→c→d→a. It should be noted that the term "vibration" is used to express not only the linear reciprocal movement, but also the square-step movement, the triangular-step movement, the circular-wise movement, etc. By selecting the repetition frequency (1/T) of the driving voltages $V_1$ and $V_2$ to be more than several Hz, the image guide is seen to be existent at the positions denoted by the cores a, b, c and d due to the afterimage of the human eye, and therefore the resolution can be equivalently increased in the horizontal and vertical directions substantially by two times.

The driving voltages $V_1$ and $V_2$ are produced by delaying the output signal from the single signal generator by different times in two separate driving circuits, but they may be produced from two separate signal generators.

FIG. 16 is a schematic plan view showing the arrangement of cores in a modification of the first embodiment shown in FIGS. 1-7. In the first embodiment, the cores of the image guide are arranged at each corners of squares, but in the present embodiment the cores are situated at apexes of triangles. In order to vibrate the image guide in a direction shown by an arrow in FIG. 16, to the bimorphs 15 and 19 is applied a stepwise driving voltage showing FIG. 17. Then, the image guide 12 is moved as illustrated in FIG. 18. That is to say, during a time interval $t_0$-$t_1$, the driving voltage is set to $V_a$ (equal to zero volt) and the image guide is situated at a position denoted by cores a. During a time intervals $t_1$-$t_2$, $t_2$-$t_3$ and $t_3$-$t_4$, the driving voltage is increased in a stepwise manner to values $V_b$, $V_c$ and $V_d$ successively, so that the image guide is moved into positions defined by cores b, c and d, successively. After that, during time intervals $t_4$-$t_5$ and $t_5$-$t_0$, the driving voltage is decreased in stepwise manner to $V_c$, $V_b$ and $V_a$ successively and the image guide is moved in the opposite directions to that during the time interval $t_0$-$t_4$ into the positions c, b and a, successively. In this manner, the image guide 12 can be reciprocally moved in the direction I in FIG. 18. It should be noted that differences between successive voltage values $V_b$-$V_a$, $V_c$-$V_b$ and $V_d$-$V_c$ are not equal to each other in order to compensate the hysteresis of the piezo-electric bimorph so that the amounts of stepwise displacements are made equal to each other. In this modified embodiment, there may be obtained the same function as that is obtained when use is made of an image guide having highly packed cores a, b, c and d, and therefore the resolution can be increased by four times.

FIGS. 19-21 shows another embodiment of the method of driving the image guide having the cores situated at apexes of regular triangles as illustrated in FIG. 17. In the present embodiment, the hysteresis characteristic of the bimorph is compensated for by improving the waveform of the driving voltage. That is to say, the signal generate 26 shown in FIG. 2 produces the driving signal having the waveform illustrated in FIG. 19. FIG. 20 is a graph representing the relation between the voltage applied to the bimorph and an amount of the displacement of the free end of the bimorph. As shown in FIG. 20, the bimorph shows the non-linear characteristic. By driving the bimorph with the driving signal shown in FIG. 19, the cores of image guide are reciprocally moved at a constant speed over a distance S illustrated in FIG. 21. At a timing $t_1$, the core has been shifted into a position at which an adjacent core was situated at a timing $t_0$. Then, the cores are moved backward at the constant speed and is returned into the initial position at the timing $t_0$. By repeating the above mentioned operation, the cores of image guide are vibrated at the constant speed and the non-linearity due to the hysteresis of the bimorph can be compensated for. Therefore, the core can be seen as a straight line depicted by a reference numeral 64, and the cores could not be distinctly seen from each other. In this case, since the image of the object is not moved in the longitudinal direction, the resolution can be improved in this direction. When a lateral distance between adjacent cores is made large, there might be produced black stripes 65 as shown in FIG. 21. However, these black stripes 65 can be completely removed by arranging the cores much more densely in the lateral direction or by increasing slightly the diameter of the core. Further, the black stripes 65 may be removed by vibrating the image guide or lens system in the lateral direction perpendicular to the black stripes like as the embodiment illustrated in FIG. 12.

FIG. 22 is a cross sectional view showing the detailed construction of the distal end of insertion section of a seventh embodiment of the endoscope according to the invention. In the present embodiment, the endoscope is constructed as the so-called side inspection type, whereas the endoscopes of the previous embodiments are all formed as the straight forward inspection type. To this end, in the present embodiment, the objective lens system 11 is secured to the side wall of hard tip member 17 by means of the cylinder 31 and the entrance end 12a of image guide 12 is bent by 90° and its entrance end face is opposed to the objective lens system 11. Similarly the exit end of light guide 31 is bent by 90° and is faced to the concave lens 35 secured to the side wall of hard tip member 17. The guard pipe 32 accommodating the entrance end 12a of image guide 12 is coupled via the spacer 14 to a free end of the laminated piezoelectric element 55 whose other end is secured by means of the spacer 16 to the arm 17d formed integrally with the hard tip member 17. The piezo-electric element 55 has an elongated shape and is extended along the longitudinal direction of the insertion section.

When the driving voltage is applied to the piezo-electric element 55 via the conductors 22a and 22b, the element is expanded and shrunk in its longitudinal direction, so that the entrance end 12a of image guide 12 is vibrated in the direction perpendicular to the optical axis O of the image guide 12 and the resolution can be improved.

In the above embodiments, the driving voltage of one polarity is applied to the piezo-electric bimorph element and laminated piezo-electric element, but it is also possible to use the A.C. voltage having both polarities. Also in case of using the A.C. driving voltage, the hysteresis characteristic of the element can be compensated for by suitably selecting the waveform of the driving voltage. It should be further noted that it is not always necessary to arrange the elongated piezo-electric element along the longitudinal direction of the insertion section, but it may be inclined by an angle smaller than ±45° with respect to the longitudinal direction of the insertion section. Further, the exit end of image guide and the eyepiece lens system may be driven by any other mechanism than the piezo-electric driving element, because there is a large space for arranging the large driving mechanism such as solenoid and permanent magnet in the proximal end of insertion section.

FIG. 23A is a longitudinal cross section showing the distal end of insertion section of an eighth embodiment of the endoscope according to the invention. FIG. 23B is a cross sectional view cut along a line B—B in FIG. 23A. In the present embodiment, the objective lens system and the entrance end of image guide are mutually moved in two orthogonal directions like as the sixth embodiment shown in FIG. 12. In the distal end of insertion section, there are arranged first and second bimorphs 15a and 15b which extend along the optical axis O of the objective lens system 11 and image guide 12. One ends of the bimorphs 15a and 15b are secured via spacers 14a and 14b, respectively to the guard pipe 32 accommodating the entrance end 12a of image guide 12 and the other ends are secured by means of the spacers 16a and 16b, respectively to the hard tip member 17. As clearly shown in FIG. 23B, the first bimorph 15a is arranged such that its main surface situates in the horizontal plane, whereas the second bimorph 15b is arranged in the vertical plane.

When the driving voltages $V_1$ and $V_2$ shown in FIGS. 24A and 24B are applied to the first and second bimorphs 15a and 15b the cores 12-1, 12-2, 12-3 of the image guide 12 are moved two dimensionally as illustrated in FIGS. 25A–25E. That is to say, when the driving voltages are not applied to the bimorphs 15a, 15b, the cores are positioned at a standard position shown in FIG. 25A. During a time period Ta, only the first bimorph 15a is driven by the positive driving voltage $V_1$ so that the cores are first shifted downward as shown in FIG. 25B and then is returned into the standard position. During the successive time periods Tb, Tc and Td, the bimorph 15a is driven with the negative voltage and the bimorph 15b is driven with the positive and negative voltage $V_2$, and thus the cores are moved upward illustrated in FIG. 25C, leftward as depicted in FIG. 25D and rightward as shown in FIG. 25E. In this manner, the entrance end 12a of image guide 12 is moved two-dimensionally in the vertical and horizontal directions.

It should be noted that the exit end of image guide and eyepiece lens system are also mutually moved two-dimensionally in the corresponding manner.

FIGS. 26A and 26B are graphs showing the waveforms of another example of the bimorph driving voltages $V_1$ and $V_2$. In this embodiment, the driving voltages $V_1$ and $V_2$ are phase-shifted by 90° from each other. When no driving voltage is applied to the bimorphs 15a and 15b, the cores 12-1, 12-2 and 12-3 are situated at the standard position shown in FIG. 27A. At a timing $t_1$, the cores are shifted downward as illustrated in FIG. 27B, at a timing $t_2$, the cores are moved leftward as shown in FIG. 27C, at a timing $t_3$, the cores are shifted upward as depicted in FIG. 27D, and at a timing $t_4$, the cores are moved rightward as illustrated in FIG. 27E. Therefore, the cores are rotated along a circle having a center O'.

In the above described embodiment, the two bimorphs 15a and 15b are arranged such that their major surfaces are arranged orthogonally, but they may be arranged differently. Further, the number of bimorphs may be more than two. Moreover, by selecting the waveforms of the driving voltages, it is possible to cause the two-dimensional movement other than those explained above. For instance, the image guide may be moved along an elliptic locus or wave-like locus.

FIGS. 28 and 29 show the detailed construction of the distal end of insertion section of a ninth embodiment of the endoscope according to the invention. In all the previous embodiments, the elongated piezo-electric elements are arranged along the longitudinal direction, but in the present embodiment, use is made of a helically coiled piezo-electric element. FIG. 28A is a longitudinal cross section and FIG. 28B is a lateral cross section cut along a line I—I in FIG. 28A. The endoscope comprises objective lens system 11, image guide 12, a pair of light guides 33a and 33b, forceps channel 66 and air/water supply channel 67. As usual, a forceps can be inserted into the forceps channel 67 and living tissues can be picked up.

The objective lens system 11 is secured to the hard tip member 17 by means of three cylinders 31a, 31b and 31c. The last lens element of objective lens system 11 is directly secured to the entrance end face of image guide 12. In the hard tip member 17 there are formed openings for accommodating the objective lens system 11, light guides 33a, 33b, forceps channel 66 and air/water supply channel 67 and the front end of hard tip member 17 is covered with a front cover 68 made of rubber except for the openings. To the rear end of hard tip member is secured a first joint frame 36a of bending mechanism 36. The hard tip member 17 and bending mechanism 36 are covered with the flexible rubber tube 37 whose front end is secured to the hard tip member 17 with the aid of a string 69.

The entrance end 12a of image guide 12 is accommodated in the guard pipe 32 and the image guide is surrounded by a flexible tube 70 whose front end is coupled with the rear end of the guard pipe 32. The exit ends of light guides 33a and 33b are accommodated in guard pipes 38a and 38b, respectively.

The forceps channel 66 is formed by an opening 66a formed in the hard tip member 17, a metal pipe 66b lamped into the opening 66a and a flexible tube 66c clamped onto the pipe 66b. Similarly the air/water supply channel 67 comprises a metal pipe 67a and a flexible tube 67b and a flexible tube 67b clamped onto the pipe 67a.

In the present embodiment, a helically coiled piezo-electric bimorph 71 is arranged within a space surrounded by the first joint frame 36a of the bending mechanism 36. That is to say, the bimorph 71 is arranged in a plane perpendicular to the optical axis O of the objective lens system 11 and image guide 12. As clearly shown in FIG. 28B, the free end of bimorph 71 is secured with the aid of adhesive agent to the outer surface of guard pipe 32 accommodating the entrance end 12a of image guide 12 and the fixed end of bimorph is secured also with the aid of adhesive agent to an inner surface of first joint frame 36a. When the driving voltage is applied to the bimorph 71, the bimorph is moved in the coiled and uncoiled manner, so that the entrance end 12a of image guide 12 is moved reciprocally along the plane perpendicular to th optical axis O.

In the present embodiment, the exit end of image guide is also moved with the aid of a similar helically coiled bimorph in synchronism with the movement of the entrance end 12a of image guide.

In the present embodiment, since the helically wound bimorph 71 is arranged along the cylindrical joint frame 36a, the length of the bimorph can be made longer. Therefore, the image guide can be moved over the desired distance without increasing the diameter of the distal end of insertion section, and further the driving voltage applied to the bimorph can be decreased, so that the safety can be improved. This is especially important for the medical endoscope.

FIGS. 29A and 29B are cross sectional views showing a tenth embodiment of the endoscope according to the invention. In the present embodiment, the helically wound piezo-electric bimorph 71 is arranged within a space formed between the guard pipe 32 for the image guide 12 and the cylinder 31c for supporting the objective lens system 11. One end of bimorph 71 is cemented to the outer surface of guard pipe 32 and the other end is secured to the inner wall of cylinder 31c. In the present embodiment, the exit end of image sensor and the eyepiece lens system are not mutually moved, but are stationary. It has been experimentally recognized that even if only the objective lens system and the exit end of image guide are mutually moved, it is possible to remove the black mesh and to improve the resolution to a susceptible extent.

FIG. 30 is a cross sectional view showing a modification of the embodiment shown in FIGS. 28A and 28B. In the embodiment illustrated in FIGS. 28A and 28B, the free end of helically coiled bimorph 71 is bent circularly in accordance with the circular shape of the guard pipe 32 and is brought into contact with the guard pipe. In the present embodiment, the end face of the bimorph 71 is brought into contact with the outer surface of guard pipe 32 and is cemented thereto. Therefore, the whole length of the bimorph up to its free end can serve to move the entrance end 12a of image guide 12.

As explained above, according to the invention the black mesh can be removed as well as the resolution can be improved. In case of using the image guide composed of a bundle of fine optical fibers, one or more optical fibers might be broken. Then, there might be produced black dots in the image which deteriorate image quality. According to the invention such black dots can be also removed by causing the relative movement of the objective lens and the image guide over a distance more than the pitch between adjacent fibers. This will be further explained in detail.

Figure 31B:
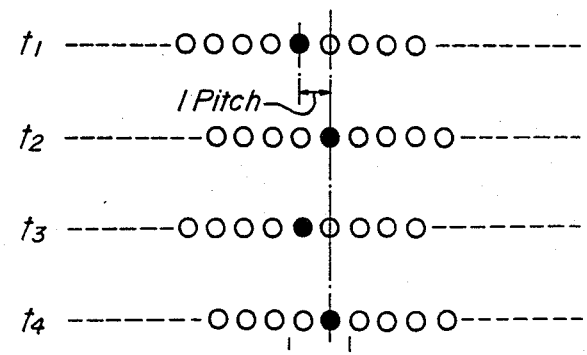
Figure 31C:
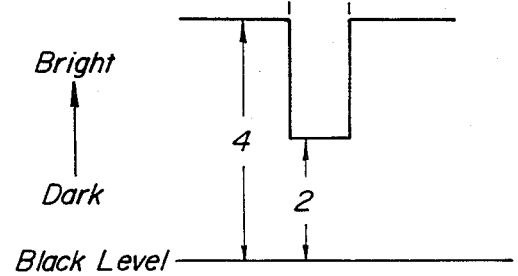

FIG. 31A shows the waveform of the driving voltage similar to that illustrated in FIG. 4, FIG. 31B is a schematic view representing the reciprocal movement of the image guide, and FIG. 31C is a graph representing the relative brightness of light transmitted through the image guide. In FIG. 31B, the broken fibers are denoted by black dots. By selecting the amplitude of the driving voltage such that the image guide is moved over the distance equal to one pitch of the optical fiber array, the black dots are also vibrated over one pitch, and thus normal optical fibers are driven into positions at which the black dots were situated. Therefore, the brightness of core columns including two black dots becomes equal to a half of the brightness of core columns without broken fibers, and the black dots in the image are not manifested. It should be noted that the black mesh and Moire fringe can be also removed and the resolution can be improved.

FIGS. 32A, 32B and 32C show another embodiment of the driving voltage, image guide movement and brightness change. In this embodiment, the driving voltage has two polarities and has amplitude levels which move the image guide over 4 pitches of the optical fiber arrangement. That is to say, the image guide is vibrated on both sides of a standard position $P_0$ over two pitches. By vibrating the image guide over four pitches, a plurality of normal optical fibers are successively driven into a position at which the broken fiber was situated, so that the decrease in the brightness due to the black dots can be further reduced. That is to say, the brightness of core columns including broken fibers can be represented as ¾ and 3.5/4 of that of the normal core column as shown in FIG. 32C.

Figure 33A:
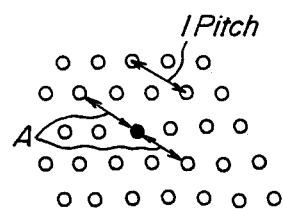
FIGS. 33A, 33B, 33C and 33D depict another embodiment of optical fiber arrangement, driving voltage, movement of the image guide and brightness variation.
Figure 33B:
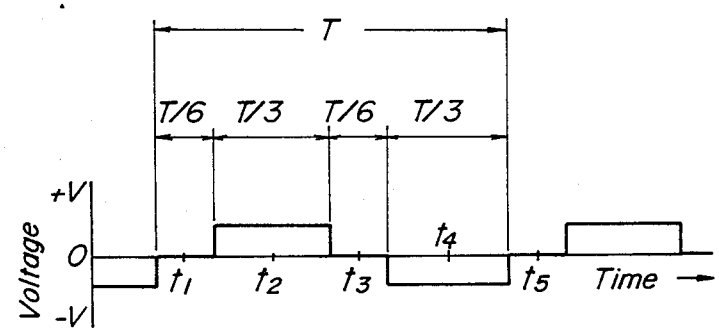

FIGS. 33A and 33B shown still another embodiment of the optical fiber arrangement and the driving voltage. In this embodiment, the optical fibers are arranged at apexes of regular triangles and the driving voltage has two polarities. An amplitude of the driving voltage is selected such that the image guide is moved in the oblique direction over two pitches as shown by arrows A in FIG. 33A.

Figure 33C:
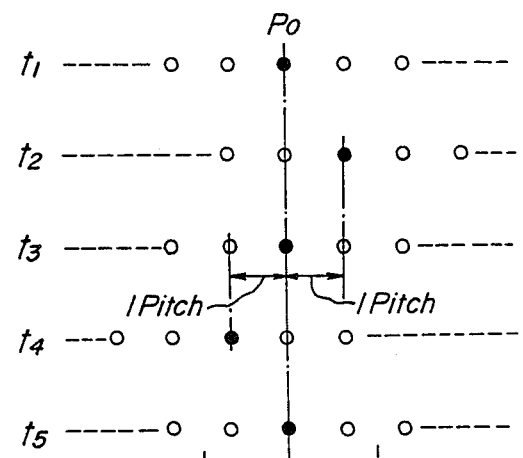
Figure 33D:
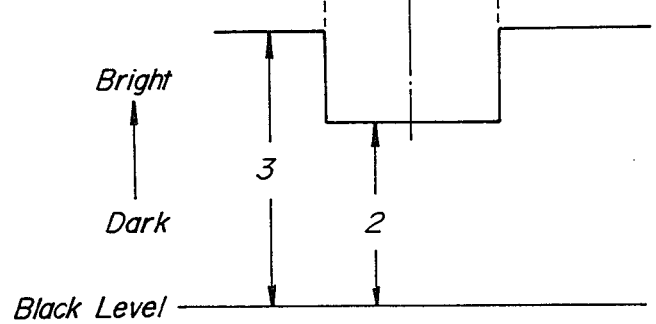

FIGS. 33C and 33D show the movement of the image guide and the brightness when the bimorph is driven by the driving voltage illustrated in FIG. 33B. The image guide is moved over two pitches, i.e. one pitch on both sides of the standard position $P_0$. Therefore, the brightness of the core column including broken fibers becomes ⅔ of that of the core column without broken fibers. As shown in FIGS. 33B, the time intervals during which the optical fibers are situated in the standard position and rightwardly and leftwardly deviated positions are preferably equal to each other, i.e. T/3.

In the endoscope, various kinds of tubes are inserted within the insertion section. In order to reduce the frictional resistance between these tubes, a solid state lubricant is contained in the insertion section. For instance, the solid state lubricant includes as a main composition fine particles of molybdenum disulfide having a particle size of about 1 μm. According to the invention, the entrance end of image guide is moved in order to remove the black mesh, Moire fringe and black dots as well as to improve the resolution. To this end, it is necessary to form a space between the hard tip member and the image guide. Then the solid state lubricant penetrates into the space and might be adhered or applied on the end surface of image guide and objective lens surfaces. This results in the serious deterioration in the optical property of these elements. The similar problem might be produced at the proximal end of insertion section. The embodiment shown in FIGS. 34 and 35 can solve this problem.

FIGS. 34A and 34B are cross sectional views showing eleventh embodiment of the endoscope according to the invention. In this embodiment, the guard pipe 32 accommodating the entrance end 12a of image guide 12 is freely inserted into a hole 72 formed in the hard tip member 17, and an opening of the hole is closed with a ring shaped lid-like member 73 so that the space within the hole 72 is isolated from the environment. The elongated piezo-electric bimorph 15 is arranged in the closed space and its free end is secured to a tip flange 32a integrally formed with the guard pipe 32 and the other end of bimorph is secured to the lid-like member 73. It should be noted that the rear end portion of guard pipe 32 is projected beyond the lid-like member 73. When the driving voltage is applied to the bimorph 71 by means of the conductors 22a and 22b, the bimorph can be bent and the entrance end 12a of image guide 12 can be moved in a direction substantially perpendicular to the optical axis O. In this case, the contact point between the guard pipe 32 and the lid-like member 73 serves as a fulcrum.

In the present embodiment, since the space in which the entrance end 12a of image guide 12 is accommodated is closed by the lid-like member 73, and therefore the solid state lubricant could not be entered into the space and the end face of image guide and objective lens system 11 can be entirely free from the lubricant to keep the optimum optical property for a long time.

FIG. 35 is a cross section illustrating a modification of the eleventh embodiment shown in FIGS. 34A and 34B. In the present embodiment, the fixed end of bimorph 15 is directly secured to the hard tip member 17 and a space between the opening of hole 72 and the guard pipe 32 accommodating the entrance end 12a of image guide 12 is closed by means of a plug member 74 made of a soft adhesive agent such as RTV rubber. In this embodiment, since the plug member 74 has the resiliency, the guard pipe 32 can be easily vibrated and further the manufacturing process becomes simple, so that the cost can be reduced.

FIGS. 36A is a cross sectional view showing the detailed construction of the distal end of insertion section of a twelfth embodiment of the endoscope according to the invention, and FIG. 36B is a cross sectional view cut along a line I—I in FIG. 36A. In the embodiments shown in FIGS. 28, 29 and 30 the helically wound bimorph is used for vibrating the entrance end of image guide. In the present embodiment, instead of the helically wound bimorph, a circularly wound bixmorph 75 is used. That is to say, within the space surrounded by the first joint frame 36a, there is arranged the circularly wound bimorph 75 whose free end is secured to one end of connecting rod 76 and whose other end is secured to the outer surface of guard pipe 32 accommodating the image guide 12 As illustrated in FIG. 36B, the circularly wound bimorph 75 extends along the inner wall of the first joint frame 36a substantially over 360°, and there is formed a small space 77 between the both ends of bimorph. The fixed end of bimorph 75 is secured via a spacer 78 to the inner wall of first joint frame 36a. By applying the driving voltage to the bimorph 75, the entrance end 12a of image guide 12 is vibrated in the direction perpendicular to the optical axis O. Also in this embodiment, since use is made of the circularly wound bimorph 75, the long bimorph can be arranged within the small space. Therefore, the sufficiently large displacement of the image guide 12 can be attained with the driving voltage having the lower amplitude without increasing the diameter and length of the distal end of insertion section.

Figure 37:
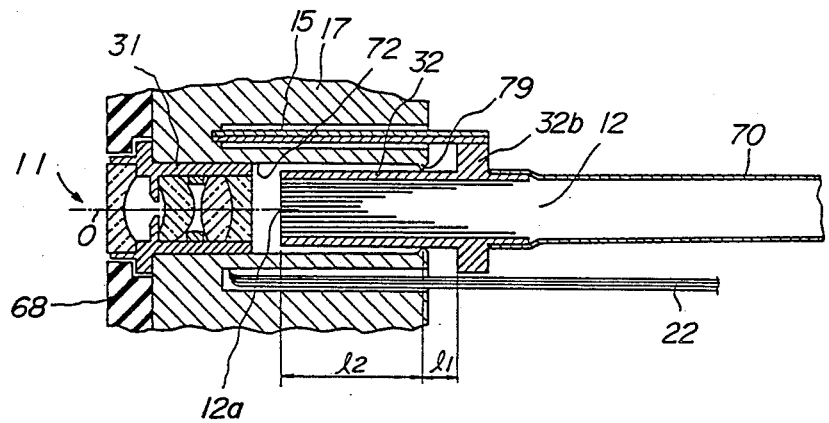
FIG. 37 is a cross sectional view illustrating the distal end of insertion section of a thirteenth embodiment of the endoscope according to the invention.

FIG. 37 is a cross sectional view illustrating the construction of the distal end of insertion section of a thirteenth embodiment of the endoscope according to the invention. In the present embodiment, the entrance end 12a of image guide 12 is freely inserted into the hole 72 formed in the hard tip member 17. At the opening of hole 72 there are formed a fulcrum projection 79 which is urged against the outer surface of the guard pipe 32 accommodating the image guide 12. Near the rear end portion of the guard pipe 32 there is formed a flange 32b. As shown in FIG. 37, a length l1 between fulcrum projection 79 and the flange 32b is shorter than a length l2 between the fulcrum projection and the entrance end face of image guide 12 (l1<l2). The elongated piezoelectric bimorph 15 is extended in the longitudinal direction of the insertion section. One end of bimorph 15 is secured to the flange 32b and the other end is connected to the hard tip member 17. By applying the driving voltage to the bimorph 15 via the conductors 22, the bimorph is bent and the entrance end 12a of image guide 12 is vibrated in the direction substantially perpendicular to the optical axis O. In this case, the guard pipe 32 is swung about the fulcrum projection 79 just like as the cantilever. Therefore, even if the amplitude of swinging motion is small at the rear end of guard pipe 32, the front end of guard pipe is vibrated over a long distance. Therefore, the amplitude of the driving voltage may be decreased and the length of the bimorph 15 may be shortened.

Figure 38:
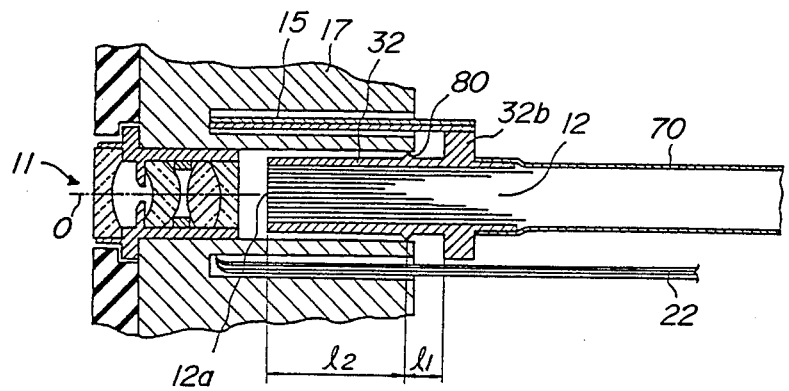
FIG. 38 is a cross sectional view showing a modification of the embodiment shown in FIG. 37.

FIG. 38 is a cross sectional view illustrating the construction of the distal end of insertion section of a modification of the embodiment shown in FIG. 37. In the present embodiment, on the outer surface of guard pipe 32, there is formed a fulcrum projection 80 which is urged against the inner wall of hole 72 near its openings. Also in this embodiment, the distance l1 is smaller than the distance l2. The remaining construction of the present embodiment is entirely same as the previous embodiment illustrated in FIG. 37.

FIG. 39 is a schematic cross section showing the construction of a fourteenth embodiment of the endoscope apparatus according to the invention. The construction of the distal end 9 of insertion section 4 and the operation section 3 is similar to that of the first embodiment illustrated in FIG. 2. That is to say, the elongated piezo-electric bimorph 15 is arranged in the hole 72 formed in the hard tip member 17 along the longitudinal direction of the insertion section. One end of bimorph 15 is secured at its one end to the flange 32a provided at the front end of guard pipe 32 accommodating the entrance end 12a of image guide 12 and the other end of bimorph is secured to the hard tip member 17. At the proximal end 12b of image guide 12 arranged in the operation section 3, there is arranged the elongated piezo-electric bimorph 19 whose one end is secured to a flange 62a of guard pipe 62 accommodating the exit end 12b of image guide 12, the other end of bimorph being secured to the hard member 21 of the operation section 3. The bimorph 15 arranged in the distal end 9 of insertion section 4 is connected to a pulse generator 81 via the conductors 22a and 22b and similarly the bimorph 19 provided in the proximal end of insertion section is connected by means of the conductors 23a and 23b to the pulse generator. As schematically illustrated in FIG. 39, the conductors 22a, 22b and 23a, 23b are extended in the universal code 5 and the pulse generator 81 is arranged outside the endoscope 1 separately from the light source unit 82. To the pulse generator 81 there is connected a switch 83. When the switch 83 is closed, the pulse generator 81 generates the pulsatory driving voltage on the conductors 22a, 22b, 23a, 23b.

In the present embodiment, the bimorphs 15 and 19 are constructed to have the same specification and the guard pipes 32 and 62 are also formed to have the same specification, so that the substantially same vibration moment are applied to the guard pipes. Therefore, when the driving voltage is commonly applied to the bimorphs 15 and 19, the distal end 12a and the proximal end 12b of image guide 12 can be vibrated under the substantially same conditions, i.e. same amplitude, same frequency and same phase. Then, the black mesh and Moire fringe can be effectively removed without deteriorating the image quality. Moreover, the bimorphs 15, 19 and the guard pipes 32, 62 can be manufactured commonly and further the single pulse generator 81 is sufficient, so that the whole apparatus can be made simple in construction, small in size and cheap in cost.

FIG. 40 is a cross sectional view illustrating the construction of a modification of the embodiment shown in FIG. 39. In the present embodiment, instead of vibrating the distal end and proximal ends of image guide, parts of the objective lens system and eyepiece lens system are vibrated by means of the elongated bimorphs extending in the longitudinal direction of the insertion section. That is to say, a lens element 11a of the objective lens system 11 is arranged in a separate cylinder 31b from a cylinder 31a accommodating the remaining lens elements of the objective lens system. One end of bimorph 15 is secured to the cylinder 31a and the other end of bimorph is coupled with the lid-like member 73 which closes the opening of hole 72. Similarly, a single lens element 13a of the eyepiece lens system 13 is accommodated in a cylinder 61b separately provided from a cylinder 61a supporting the remaining lens elements of the eyepiece lens system. One end of bimorph 19 is secured to the cylinder 61b and the other end of bimorph is connected to a lid-like member 84 which closes a hole 85 formed in the hard member 21. As explained above with reference to FIG. 34A, the lid-like members 73 and 84 serve to prevent the solid state lubricant from being introduced into the holes 72 and 85. The bimorphs 15 and 19 are commonly connected to the single pulse generator 81 via the conductors 22a, 22b and 23a, 23b. When the driving voltage is applied to the bimorphs 15 and 19 by closing the switch 83, the lens elements 11a and 13a are vibrated in the direction substantially perpendicular to the optical axis O over the substantially same amplitude at the same frequency and phase. In the present embodiment, the total weight of the lens 11a and cylinder 31b is substantially equal to that of the lens 13a and cylinder 61b, so that the lenses 11a and 13a are subjected to the almost same vibration moments.

In the embodiment illustrated in FIG. 39, the guard pipes 32 and 62 accommodating the distal and proximal ends 12a and 12b of image guide 12 have the same shape and weight. However, these guard pipes 32 and 62 may be formed differently from each other. In such a case, in order to apply the substantially same vibration moments to the distal end and proximal end, one of the guard pipes, for instance, the guard pipe 62 at the proximal end of insertion section may be formed differently from the guard pipe 32 at the distal end of insertion section. For instance, a recess 86 may be formed in the outer surface of the guard pipe 62 as depicted in FIG. 41, so that the distal end and proximal end are subjected to the substantially same vibration moments. Further, the guard pipes 32 and 62 may be made of metals having different specific gravities.

Figure 42B:
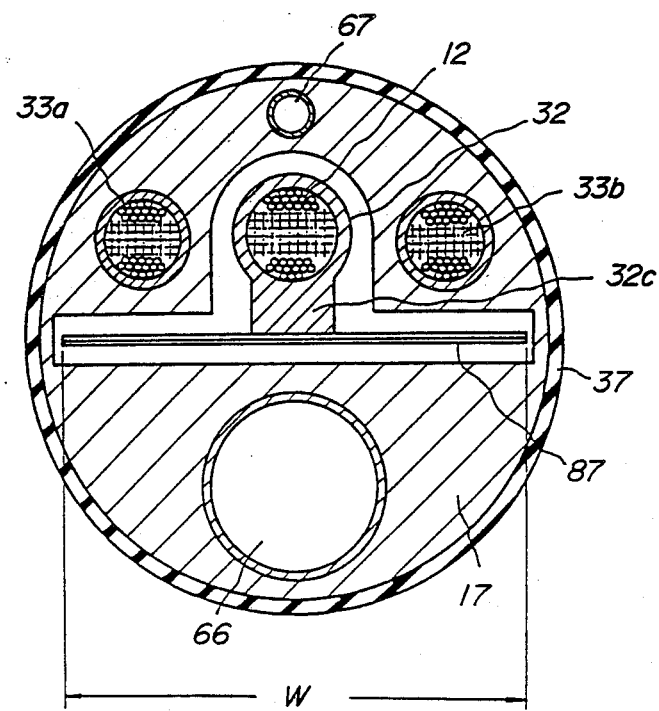

FIGS. 42A and 42B are cross sectional views showing the detailed construction of the distal end of insertion section of a fifteenth embodiment of the endoscope apparatus according to the invention. This embodiment is similar to the ninth embodiment illustrated in FIGS. 28A and 28B. In the ninth embodiment, the helically coiled piezo-electric bimorph 71 is arranged along the inner wall of the first joint frame 36a. In the present embodiment, a relatively wide plate-like piezo-electric bimorph 87 is arranged substantially in a plane passing through the center of the distal end of insertion section. That is to say, as clearly shown in FIG. 42B, the width direction of the bimorph 87 is substantially coincided with the diameter direction of the cylindrical hard tip member 17. One end of bimorph 87 is secured with the aid of an adhesive 88 to a projection 32c integrally formed with the guard pipe 32 at its front end. The other end of bimorph 87 is secured to a supporting member 89 which is coupled with the first joint frame 36a by means of a screw 90. In the supporting member 89 there is formed an opening 89a through which the image guide 12 is freely inserted. To the rear end of guard pipe 32 are connected double flexible tubes 70a and 70b. The front rubber cap 68 is secured to the hard tip member 17 by means of a fitting 91, and a protection ring 92 made of rubber is screwed around the outer surface of hard tip member 17. The remaining construction is the same as that of the embodiment shown in FIGS. 28A, 28B. In the present embodiment, since the bimorph 87 is arranged in the plane passing through the center of the hard tip member 17, the width W of the bimorph can be increased substantially up to the diameter of the hard tip member, and therefore the bimorph can produce a large force for vibrating the distal end 12a of image guide 12. In this connection it should be noted that the bending force of the bimorph is proportional to its width, while the bending amount is proportional to its length. In the present embodiment, since the bimorph 87 extends in the longitudinal direction of the insertion section, the length of the bimorph can be also increased without prolonging the distal end of insertion section.

FIG. 43 is a cross sectional view illustrating the construction of a sixteenth embodiment of the endoscope apparatus according to the invention. In the embodiments shown in FIGS. 39 and 40, the pulse generator 81 for generating the driving voltage for the bimorphs 15, 19 is provided as the independent unit separately from the endoscope 1 and the light source unit 82. In the present embodiment, the signal generator 81 is provided in the operation section 3 and the switch 83 for controlling the actuator of the signal generator is provided on the hard member 21 constituting the housing the operation section. The remaining construction of the present embodiment is entirely same as that of the embodiment illustrated in FIG. 39. That is to say, the entrance end 12a of image guide 12 is vibrated in the direction substantially perpendicular to the optical axis O by means of the elongated bimorph 15 extending along the longitudinal direction of the insertion section 4, and similarly the exit end 12b of image guide 12 is vibrated in the same direction as that in which the entrance end 12a is vibrated, by means of the elongated bimorph 19 which also extends in the longitudinal direction of the insertion section 4. It should be noted that the power supply source for the signal generator 81 is provided in the light source unit and is connected to the signal generator by means of conductors arranged within the universal code.

In the present embodiment, since the signal generator 81 for driving the bimorphs 15 and 19 is arranged within the operation section 3, the whole construction of the endoscope 1 could not be made large. Further, the on-off switch 83 is provided on the operation section 3, it can be handled easily.

FIG. 44 is a schematic view illustrating the whole construction a seventeenth embodiment of the endoscope apparatus according to the invention. In the embodiments so far explained, the endoscope is formed as the so-called optical endoscope in which the light guide and image guide are arranged in the insertion section. Nowadays, there has been developed the video endoscope in which a small solid state image sensor is arranged in the distal end of insertion section and the image of object is displayed on a monitor. The present embodiment shows such a video endoscope. The video endoscope 101 comprises an insertion section 102 and an operation section 103. In a distal end of insertion section 102, there are arranged an illumination lens 104, an objective lens system 105, a solid state image sensor 106 including the charge coupled device (CCD) and a driving device 107 for vibrating CCD. Within the insertion section 102, there are inserted a light guide 108, a cable 109 having one end connected to CCD 106 and a cable 110 having one end connected the driving device 107. The other end of the cable 110 is connected to a signal generator 111 arranged within the operation section 103. The driving device 107 serves to vibrate the objective lens system 107 in a direction substantially perpendicular to the optical axis thereof, and may be formed by any driving means. For instance, the piezo-electric vibrating element may be provided in the driving device 107. The cable 109 connected to CCD 106 is further extended within a univerted code 112 together with the light guide 108 and a power supply line 113 for the signal generator 111. The universal code 112 is detachably coupled with an external unit 114 with the aid of a connector 115. The external unit 114 includes a light source unit 116, a power source unit (PS) 117 and a video processor unit (VP) 118. The power supply line 113 is connected to the power source unit 117 and the cable 109 is connected to the video processor unit 118. The incident end of light guide 108 is optically coupled with the light source unit 116. The video processor unit 118 supplies the driving signal for CCD and processes the electric signal supplied from CCD to derive an image signal which is supplied to a monitor 119 to display the endoscopic image of object under inspection. An on-off switch 120 connected to the signal generator (Ge) 111 is arranged on the housing of the operation section 103. Also in the present embodiment, the signal generator 111 generating the driving signal for the driving device 107 such as the piezo-electric bimorph is arranged in the operation section 103, so that the size of the video endoscope could be kept small and the operation of the switch 120 can be effected easily.

FIG. 45 is a cross sectional view showing the detailed construction of the distal end of insertion section of an eighteenth embodiment of the endoscope according to the invention. In the embodiments so far explained, the piezo-electric vibrating elements are secured to the hard members 17 and 21 of the endoscope. In general, the hard members 17, 21 are made of electrically conductive metal, so that there is a fear that the patient and doctors might be subjected to the electric shock when the electrodes of the piezo-electric elements are brought into contact with the hard members. In the present embodiment, such a danger can be effectively removed by connecting the piezo-electric element to the hard member by means of an electrically insulating member. As shown in FIG. 45, the elongated piezo-electric bimorph 15 is freely arranged within the hole 72 formed in the hard tip member 17, the bimorph extending along the image guide 12. Generally, the bimorph 15 is manufactured by sintering piezo-electric ceramic layers 15-1, 15-2 onto both major surfaces of a resilient metal plate 15-3 and applying electrode layers onto ceramic layers. The free end of bimorph 15 is secured to the flange 32c formed at a front end of guard pipe 32 accommodating the entrance end 12a of image guide 12. At the other end of bimorph 15, the ceramic layers 15-1 and 15-2 are removed so that the metal plate 15-3 is exposed. This exposed end of metal plate 15-3 is secured to one end of electrically insulating member 90, the other end of insulating member being secured to the hard tip member 17. In this way, the piezo-electric bimorph 15 is secured to the hard tip member 17 by means of the electrically insulating member 90 and the electrodes of the bimorph 15 are not electrically connected to the hard tip member 17, so that the patient as well as the doctor are effectively protected against the electric shock.

FIG. 46 is a cross sectional view depicting the construction of the distal end of insertion section of a nineteenth embodiment of the endoscope according to the invention. In this embodiment, the piezo-electric bimorph 15 is completely covered with an electrically insulating member 91 in order to prevent the electric shock much more positively.

Figure 47A:
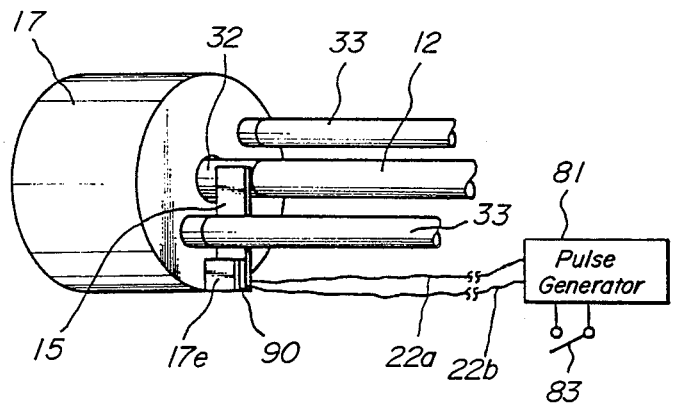
FIGS. 47A and 47B are perspective and cross sectional views, respectively illustrating the construction of the distal end of insertion section of a twentieth embodiment of the endoscope according to the invention.
Figure 47B:
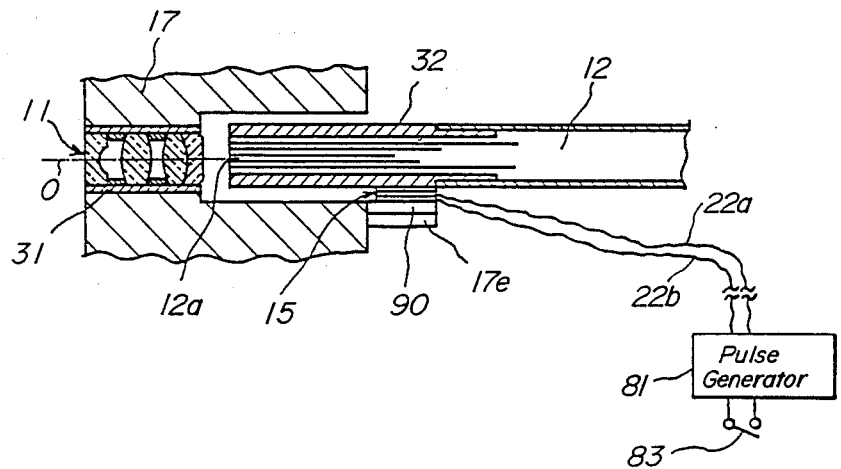

FIGS. 47A and 47B are perspective and cross sectional views, respectively illustrating the construction of the distal end of insertion section of a twentieth embodiment of the endoscope according to the invention. In the present embodiment, a piezo-electric bimorph 15 is extended in a radial direction of the hard tip member 17 and one end of the bimorph is secured to the guard pipe 32 accommodating the entrance end 12a of image guide. The other end of bimorph 15 is secured via an electrically insulating member 90 to an arm 17e formed integrally with the hard tip member 17. When the bimorph 15 is driven by applying the driving voltage from the pulse generator 81 to the bimorph via the conductors 22a, 22b, the bimorph is bent reciprocally in the plane perpendicular to the optical axis O, and thus the entrance end 12a of image guide 12 is also vibrated in the direction perpendicular to the optical axis O.

FIG. 48 is a cross sectional view showing the construction of the distal end of insertion section of a twenty first embodiment of the endoscope according to the invention. In the present embodiment, the elongated piezo-electric bimorph 15 is freely arranged within the hole 72 formed in the hard tip member 17. The free end of bimorph 15 is secured to the flange 32c formed integrally with the guard pipe 32 at its front end by means of a resilient adhesive layer 91. Similarly the other end of bimorph 15 is secured to the hard tip member 17 by means of a resilient adhesive layer 92. Therefore, the bimorph 15 can vibrate over its whole length, and therefore the amplitude of the vibrating motion of the entrance end 12a of image guide 12 is increased. In this case, since the ends of bimorph are secured to the guard pipe 32 and the hard tip member 17 via the resilient adhesive layers 91 and 92, the bimorph is hardly separated from the solid members.

FIG. 49 is a cross sectional view illustrating the construction of the distal end of insertion section of a twenty second embodiment of the endoscope according to the invention. In the present embodiment, the ends of bimorph 15 are secured by means of the adhesive layers 91 and 92 to the flange 32c of guard pipe 32 and the hard tip member 17 over smaller lengths than the embodiment shown in FIG. 48. The remaining construction of this embodiment is entirely same as the previous embodiment of FIG. 48.

FIGS. 50A and 50B are perspective and cross sectional views, respectively representing the construction of the distal end of insertion section of a twenty third embodiment of the endoscope according to the invention. In this embodiment, the piezo-electric bimorph 15 is arranged in the radial direction of the hard tip member 17 like as the embodiment shown in FIGS. 47A and 47B. One end of bimorph 15 is connected to the guard pipe 32 by means of the resilient adhesive layer 91 and the other end of bimorph is secured to the arm 17e integrally formed with the hard tip member 17 by means of the resilient adhesive layer 92.

FIGS. 51A and 51B are perspective and cross sectional views, respectively showing the distal end of insertion section of a twenty fourth embodiment of the endoscope according to the invention. In the present embodiment, a part of the objective lens system 11 is vibrated in the direction perpendicular to the optical axis O by means of the bimorph 15 extending in the radial direction of the hard tip member 17. To this end, one end of bimorph 15 is secured via the resilient adhesive layer 91 to one end of an arm 93 extending along the optical axis O, the other end of arm being secured to the cylinder 31b accommodating a lens 11a of the objective lens system 11. The remaining lenses of the objective lens system 11 are arranged in the cylinder 31a which is fixed to the hard tip member 17. The other end of bimorph 15 is secured to the arm 17e via the resilient adhesive layer 92.

FIGS. 52 and 53 are cross sectional views showing the construction of modified embodiments of the bimorph provided in the distal end of the endoscope according to the invention. The embodiment shown in FIG. 52 is similar to that illustrated in FIG. 36B and the embodiment depicted in FIG. 53 is similar to that shown in FIG. 28B. In the embodiment of FIG. 52, the circular bimorph 75 is arranged along the inner wall of first joint frame 36a, and ends of bimorph are secured via the resilient adhesive layers 91 and 92 to the guard pipe 32 of the image guide 12 and the first joint frame 36a, respectively.

FIG. 54 is a cross sectional view illustrating the distal end of insertion section of a twenty fifth embodiment of the endoscope according to the invention. In the embodiments so far explained except for that shown in FIG. 45, the bimorph has the piezo-electric ceramic layers applied on the surfaces of the resilient metal plate over its whole length. Then, the portions of bimorph which are secured to the movable portion and the fixed portion are also vibrated, so that there is produced a relatively large force at the connection points and the bimorph tends to be separated partially or completely from the movable and fixed portions during the long time period. Then, the vibration movement could no more be produced properly so that the resolution becomes lower and the black mesh and Moire fringes could not be removed effectively. In order to prevent the bimorph from being separated from the movable and fixed members, in the present embodiment, both ends of the metal plate 15-3 are free from the piezo-electric ceramic layers 15-1 and 15-2 and the exposed ends of metal plate 15-3 are firmly secured by adhesive to the flange 32c of guard pipe 32 accommodating the entrance end 12a of image guide 12 and to the hard tip portion 17.

FIGS. 55A and 55B are perspective and cross sectional views, respectively showing the distal end of insertion section of a twenty sixth embodiment of the endoscope according to the invention. In the present embodiment, the bimorph 15 having both ends of metal plate 15-3 exposed from the ceramic layers 15-1 an 15-2 is arranged in the radial direction of the hard tip member 17. One end of metal plate 15-3 is firmly secured to the outer surface of guard pipe 32 and the other end is firmly secured to the arm 17e formed integrally with the hard tip member 17.

Figure 56A:
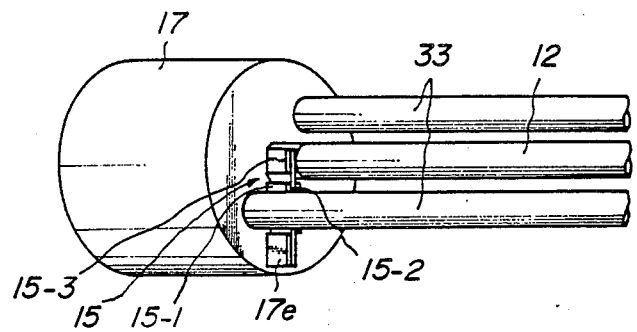
FIGS. 56A and 56B are perspective and cross sectional views representing the construction of the distal end of a twenty seventh embodiment of the endoscope according to the invention.
Figure 56B:
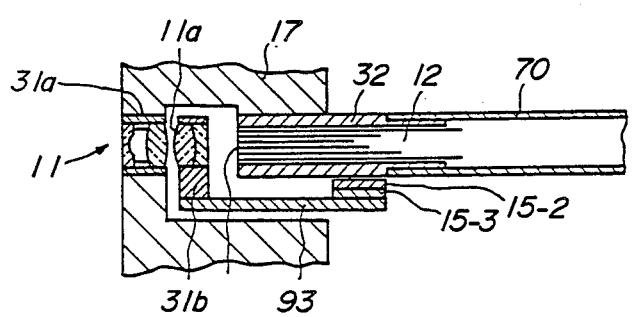

FIGS. 56A and 56B are perspective and cross sectional views, respectively depicting the construction of the distal end of insertion section of a twenty seventh embodiment of the endoscope according to the invention. Also in the present embodiment, use is made of the bimorph 15 extending in the radial direction of the hard tip member 17. The exposed one end of metal plate 15-3 of bimorph 15 is secured to one end of the arm 93 whose other end is secured to the cylinder 31b accommodating the lens 11c of the objective lens system 11. The other exposed end of metal plate 15-3 is secured to the arm 17e formed integrally with the hard tip member 17.

Figure 57:
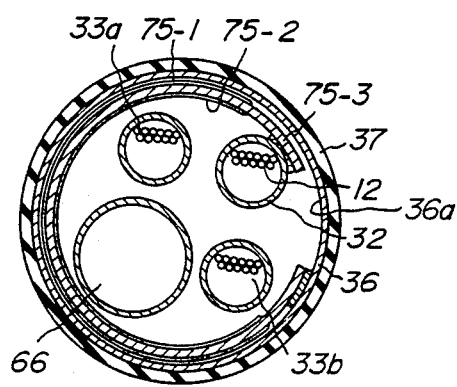
FIGS. 57 and 58 are cross sectional views depicting modifications of the embodiments shown in FIGS. 52 and 53, respectively.
Figure 58:
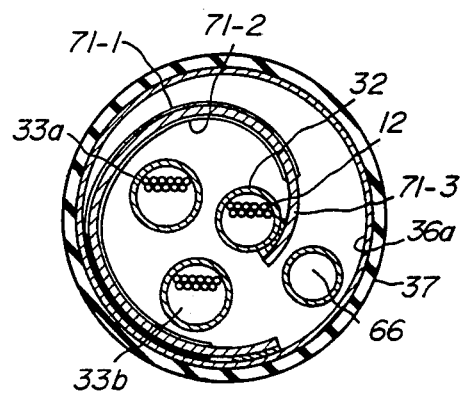

FIGS. 57 and 58 are cross sectional views showing modifications of the embodiments illustrated in FIGS. 52 and 53, respectively. In the embodiment shown in FIG. 57, both ends of the circularly wound metal plate 75-3 are free from the ceramic layers 75-1, 75-2 and are exposed. The exposed ends are secured to the guard pipe 32 accommodating the entrance end 12a of image guide 12 and the first joint frame 36a, respectively. In the embodiment illustrated in FIG. 58, both ends of helically wound metal plate 71-3 are free from the ceramic layers 71-1, 71-2 and are secured to the guard pipe 32 and the first joint frame 36a, respectively.

Figure 59:
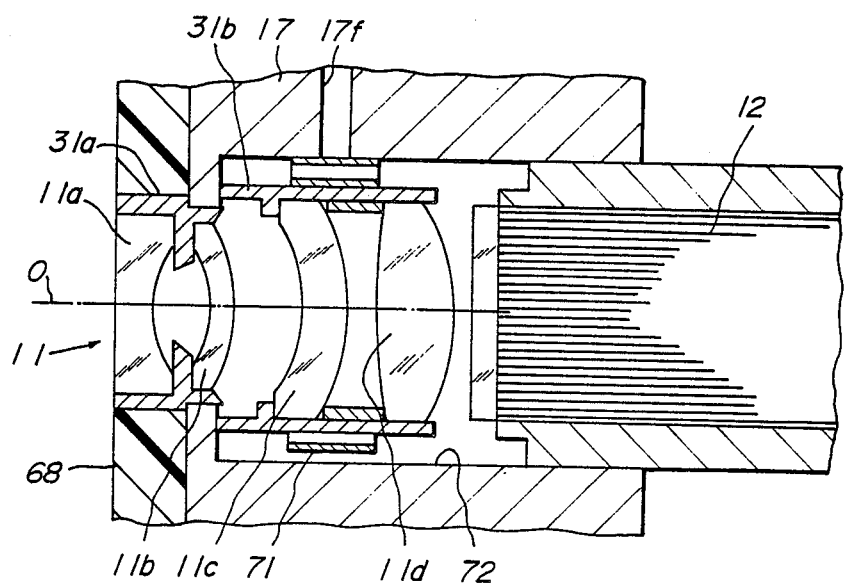
FIG. 59 is a cross sectional view showing the construction of the distal end of insertion section of a twenty eighth embodiment of the endoscope according to the invention.

FIG. 59 is a cross sectional view showing the construction of the distal end of insertion section of a twenty eighth embodiment of the endoscope according to the invention. In the present embodiment, the helically wound piezo-electric bimorph 71 is used to vibrate a part of the objective lens system 11. To this end, lenses 11a, 11b are arranged in the cylinder 31a and lenses 11c, 11d are provided in the cylinder 31b which is freely arranged in the hole 72 formed in the hard tip member 17. The helically coiled bimorph 71 is arranged along the inner wall of hole 72, and one end of the bimorph is secured to the outer surface of cylinder 31b and the other end is secured to the inner wall of hole 72. In a portion of the hard tip member 17 at which the other end of bimorph is secured to the hard tip member, there is formed a lateral hole 17f through which an adhesive agent can be applied to the connection point between the bimorph and the hard tip member.

Figure 60:
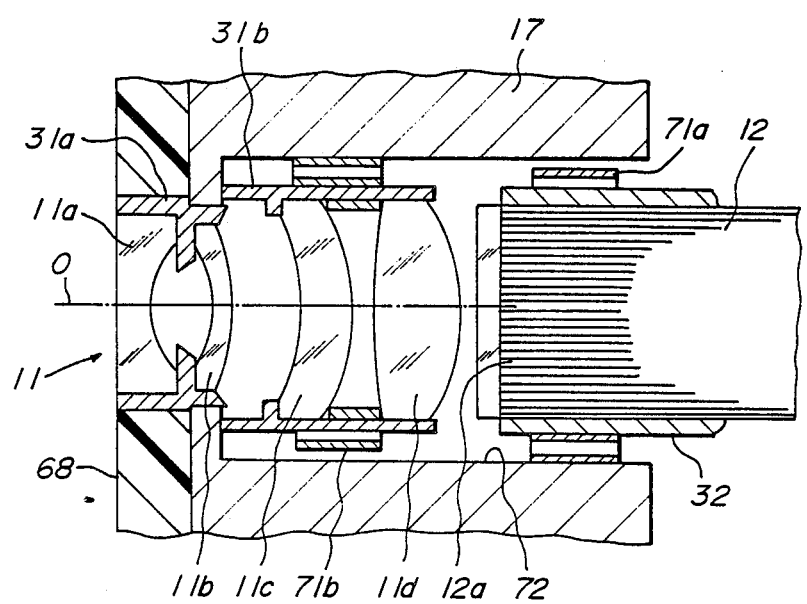
FIG. 60 is a cross sectional view illustrating the construction of the distal end of insertion section of a twenty ninth embodiment of the endoscope according to the invention.

FIG. 60 is a cross sectional view showing the construction of the distal end of insertion section of a twenty ninth embodiment of the endoscope according to the invention. In the present embodiment, in the hole 72 there are arranged first and second bimorphs 71a and 71b both of which are wound helically along the inner wall of hole 72. One end of the first bimorph 71a is secured to the guard pipe 32 accommodating the entrance end 12a of image guide 12 and the other end is secured to the inner wall of hole 72. Similarly, one end of second bimorph 71b is connected to the lens holding cylinder 31b supporting the lens elements 11c and 11d of the objective lens system 11. It should be noted that the first and second bimorphs 71a and 71b are polarized such that the entrance end 12a of image guide 12 and the lens elements 11c, 11d are vibrated in opposite directions.

FIGS. 61A and 61B are cross sectional views illustrating the construction of the distal end of a thirtieth embodiment of the endoscope according to the invention. In the present embodiment, a spirally coiled piezoelectric bimorph 94 is arranged in a space between the guard pipe 32 for the entrance end 12a of image guide 12 and the lens supporting cylinder 31c of the objective lens system 11. It should be noted that the term "spirally" means that the bimorph is extended in the axial direction, while the term "helically" means that the bimorph is not extended in the axial direction.

In the embodiments so far explained, the vibrating movement is effected at both the distal end and proximal end of insertion section or only at the distal end of insertion section, however the present invention is not limited to such embodiments, but the vibration movement may be generated only at the proximal end of insertion section. Now a few embodiments in which the vibration is effected only at the proximal end of insertion section will be explained.

Figure 62:
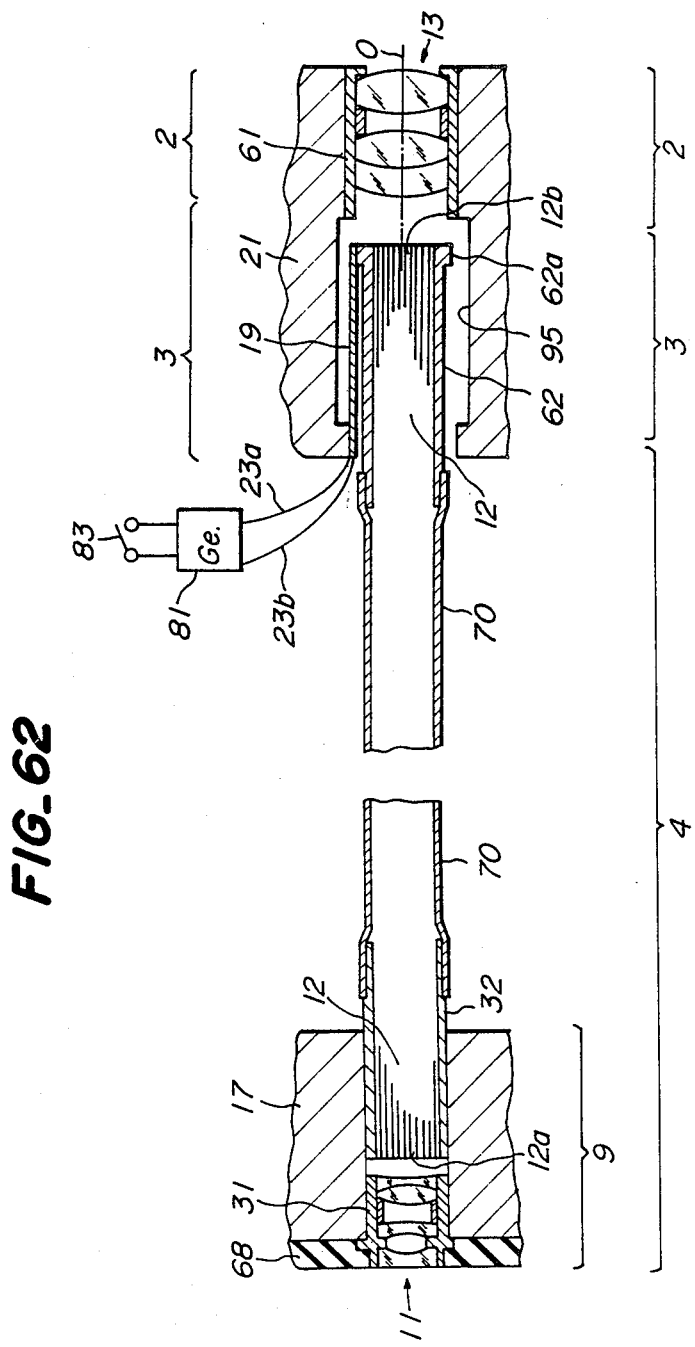

FIG. 62 is a cross sectional view showing the construction of a thirty first embodiment of the endoscope according to the invention. In the present embodiment, the construction of the distal end 9 of insertion section is entirely same as that of the known endoscope, and the objective lens system 11 and entrance end 12a of image guide 12 are fixed within the hard tip member. In the operation section 3, the exit end 12b of the image guide 12 is freely arranged in a hole 95 formed in the hard member 21. In the space between the guard pipe 62 clamped onto the exit end 12b of image guide 12 and the inner wall of hole 95, there is arranged the elongated piezo-electric bimorph 19 extending along the longitudinal direction of the image guide 12. One end of bimorph 19 is secured to a flange 62a formed integrally with the guard pipe 62 and the other end is secured to the hard member 21 at the opening of hole 95. In this embodiment, when the switch 83 is closed and the driving voltage is applied to the bimorph 19, the exit end 12b of image guide 12 is vibrated in a direction substantially perpendicular to the optical axis O, and therefore the annoying black mesh can be removed and the resolution can be increased.

Figure 63:
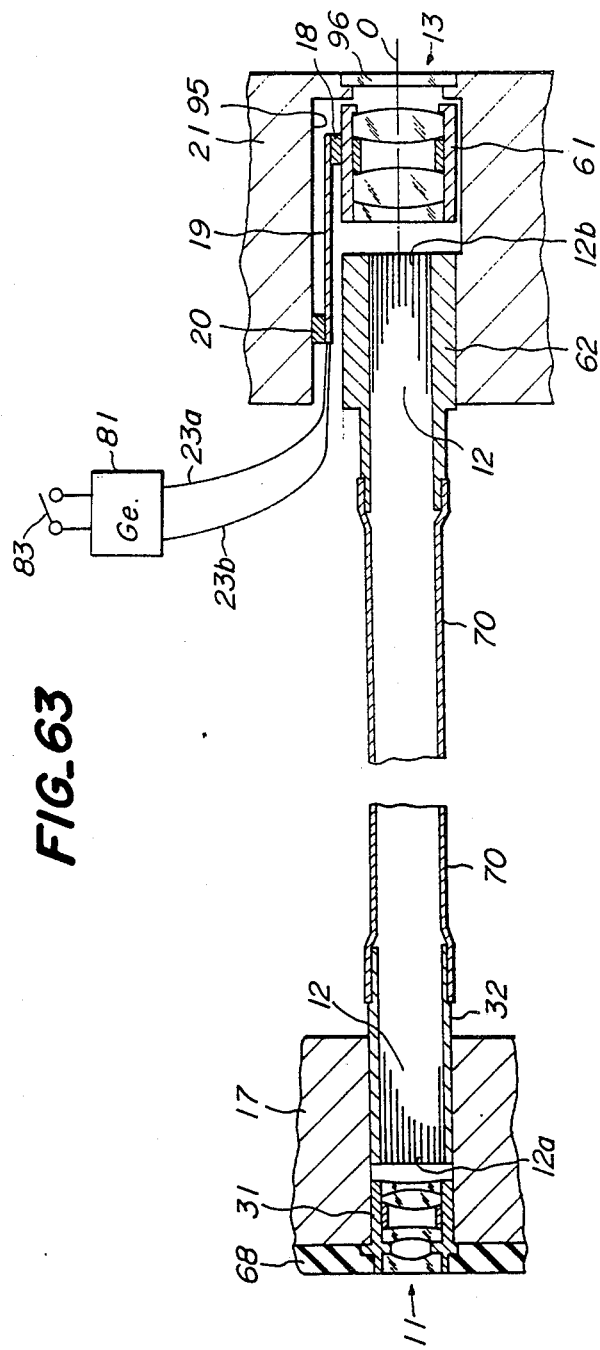

FIG. 63 is a cross sectional view depicting the construction of the proximal end of insertion section of a thirty second embodiment of the endoscope according to the invention. In the present embodiment, the eyepiece lens system 13 instead of the image guide 12 is vibrated by means of the elongated bimorph 19. For this purpose, the cylinder 61 supporting the eyepiece lens system 13 is arranged freely within the hole 93 formed in the hard member 21. One end of bimorph 19 extending along the optical axis O is secured by means of the spacer 18 to the cylinder 61 and the other end is secured via the spacer 20 to the hard member 21. In this manner, the eyepiece lens system 13 is vibrated in the direction substantially perpendicular to the optical axis O. At the opening of hole 95 there is arranged a glass plate 96.

FIG. 64 is a cross sectional view showing the construction of a thirty third embodiment of the endoscope according to the invention. In the present embodiment, first and second elongated bimorphs 19a and 19b are arranged in the hole 95 formed in the hard member 21, and the exist end 12b of image guide 12 and the eyepiece lens system 13 are vibrated in opposite directions substantially perpendicularly to the optical axis O.

Figure 65:
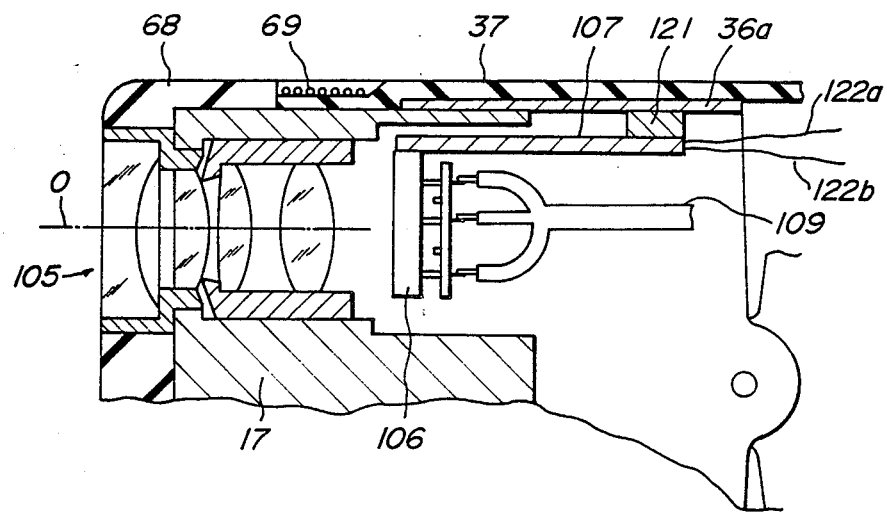
FIGS. 65 and 66 are cross sectional views illustrating the construction of the distal end of insertion section of thirty fourth and thirty fifth embodiments of the video endoscope according to the invention, in which the solid state image sensor is vibrated.

FIG. 65 is a cross sectional view showing the construction of the distal end of insertion section of a thirty fourth embodiment of the endoscope according to the invention. In the present embodiment, the endoscope is formed as the video endoscope like the embodiment illustrated in FIG. 44. The solid state image sensor 106 such as CCD is arranged in the distal end of insertion section such that it converts the optical image of the object formed by the objective lens system 105 into the electric signal which is transmitted to the video processor unit arranged separately from the endoscope by means of the signal cable 109. In the present embodiment, the elongated bimorph 107 is arranged along the longitudinal direction of the insertion section, and one end of bimorph is secured to CCD 106 and the other end is secured to the first joint frame 36a via a spacer 121. To the terminal of the bimorph 107 are connected conductors 122a, 122b which are extended in the insertion section to the signal generator producing the driving voltage for the bimorph. When the driving voltage is applied to the bimorph 107 via the conductors 122a, 122b, the bimorph is bent reciprocally and CCD 106 is also vibrated in the direction substantially perpendicular to the optical axis O of the objective lens system 105. Therefore, the Moire fringe can be effectively prevented from appearing in the video image and the resolution is improved.

Figure 66:
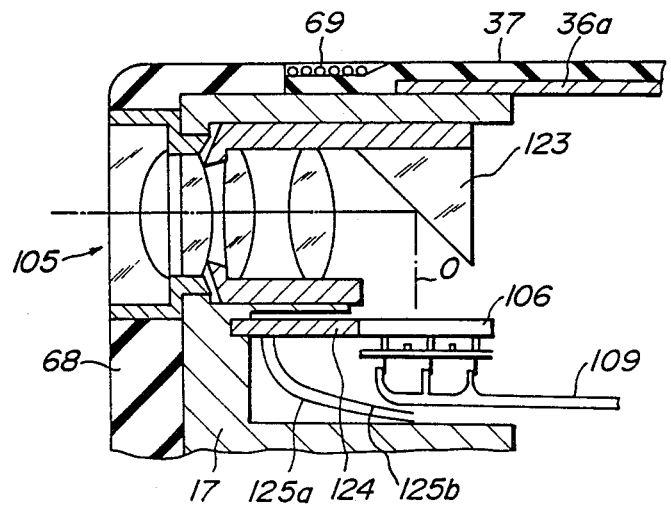

FIG. 66 is a cross sectional view representing the construction oft he distal end of a thirty fifth embodiment of the video endoscope according to the invention. In the present embodiment, the objective lens system 105 includes a triangular prism 123 and CCD 106 is arranged in a plane parallel to the longitudinal direction of the insertion section. There is arranged a laminated type piezo-electric element 124 which also extends in the longitudinal direction of the insertion section. One end of laminated piezo-electric element 124 is secured to CCD 106 and the other end is clamped into a recess formed in the hard tip member 17. When the driving voltage is applied to the laminated piez-electric element 124 by way of conductors 125a, 125b, the element is reciprocally expanded and shrunk in its longitudinal direction, so that CCD 106 is vibrated in the direction perpendicular to the optical axis O.

FIGS. 67A and 67B are cross sectional views depicting the construction of the distal end of a thirty sixth embodiment of the video endoscope according to the invention. In the present embodiment, the solid state image sensor, i.e. CCD 106 is vibrated by means of a helically wound bimorphs 126. That is to say, one end of helically coiled bimorph 126 is secured to CCD 106 and the other end is coupled with an inner wall of a hard sleeve 127 which is clamped into the hole formed in the hard tip member 17. Also in this embodiment, CCD 106 can be vibrated in a direction perpendicular to the optical axis O of the objective lens system 105.

FIG. 68 is a cross sectional view showing the construction of the distal end of insertion section of a thirty seventh embodiment of the video endoscope according to the invention. In the present embodiment, the objective lens system 105 is designed such that the focusing condition can be adjusted by moving one of lens elements in the optical direction. In order to make the construction image, it is advantageous that the focusing lens is not vibrated in the direction perpendicular to the optical axis. However, it has been experimentally confirmed that if one or more lenses which are stationary for the focus control are vibrated in order to remove the Moire fringe, the image is defocused. In the present embodiment, in order to avoid such a drawback, the focusing lens is vibrated in the direction perpendicular to the optical axis O.

As shown in FIG. 68, the objective lens system 105 is composed of eight lens elements 105a to 105h. The first and second lens elements 105a and 105b are arranged in a resilient ring 128 which is clamped into an opening formed in the hard tip member 17. The third lens element 105c is provided in a cylinder 129 and the fourth lens element 105 is arranged in a cylinder 130 which is slidably inserted into the cylinder 129 in the direction of the optical axis O. In the cylinder 129 there is formed a slit 129a through which a projection 130a formed integrally with the cylinder 130 is projected outwardly. To the projection 130a, a distal end of a focusing wire 131 is connected, the focusing wire being extended into the insertion section up to a driving unit which will be explained later. By moving the focusing wire 131 in both directions as shown by a double headed arrow A, the fourth lens element 105d is moved along the optical axis O to adjust the focus condition. The remaining lens elements 105e to 105h are arranged in a cylinder 132 which is secured to the hard tip member 17.

The elongated bimorph 107 is arranged within a space formed in the hard tip member 17, and one end of bimorph is secured to the outer surface of cylinder 129 and the other end is secured to the hard tip member 17. Therefore, when the driving voltage is applied to the bimorph 107 via the conductors 122a and 122b, the cylinders 129 and 130 are vibrated in the direction substantially perpendicular to the optical axis O. Between the cylinder 129 and the hard tip member 17 is arranged an O-ring 133.

As shown in FIG. 69, the focusing wire 131 connected to the projection 130a of cylinder 130 is extended up to a driving force transmission device (DT) 134 provided in the operation section 103. The driving force transmission device 134 is coupled with an electric driving device 135 (DD) which is connected to a focusing control circuit (FC) 136 provided in the external device 114 via the universal code 112. Further, to the electric driving device 135 is connected a driving switch 137. The cable 109 connected to CCD 106 is extended up to the video processor unit (VP) 118 to which the monitor 119 is connected. The conductors 122a, 122b connected to bimorph 106 is extended to the signal generator (SG) 111 provided in the external device 114. In the present embodiment, in order to effect the automatic focus control, the output signal from CCD 106 is processed in the video processor unit 118 to derive a focusing error signal which is supplied to the focus control circuit 136.

When the switch 137 provided on the operation section 103 is actuated, the electric driving device 135 is driven by the automatic focus control signal supplied from the focus control circuit 136 and the movement of the device 135 is transmitted to the wire 131 by means of the driving force transmission device 134. Then the fourth lens element 105d is moved in the direction of the optical axis O and the correct focusing condition is attained automatically. At the same time, the driving voltage generated from the signal generator 111 is applied to the bimorph 107 and the third and fourth lens elements 105c and 105d are vibrated in the direction substantially perpendicular to the optical axis O. In this manner, the correctly focused image having the good resolution is always displayed on the monitor 119, while the annoying Moire fringe is not appeared.

In the embodiments shown in FIGS. 44 and 65-69, the solid state image sensor, i.e. CCD and at least one lens element of the objective lens system are vibrated relative to each other. In general, the resolution of the image picked up by CCD under the vibration movement can be improved, but when the moving object is picked up, there might be generated a pseudo signal. That is to say, when the movement of the image formed on CCD amounts to more than an area of one pixel of CCD, a pseudo signal is produced at the edge of the moving object and the displayed image becomes very deteriorated. This disadvantage can be mitigated by suppressing a pseudo color signal appearing at the edge of the moving object.

Figure 70:
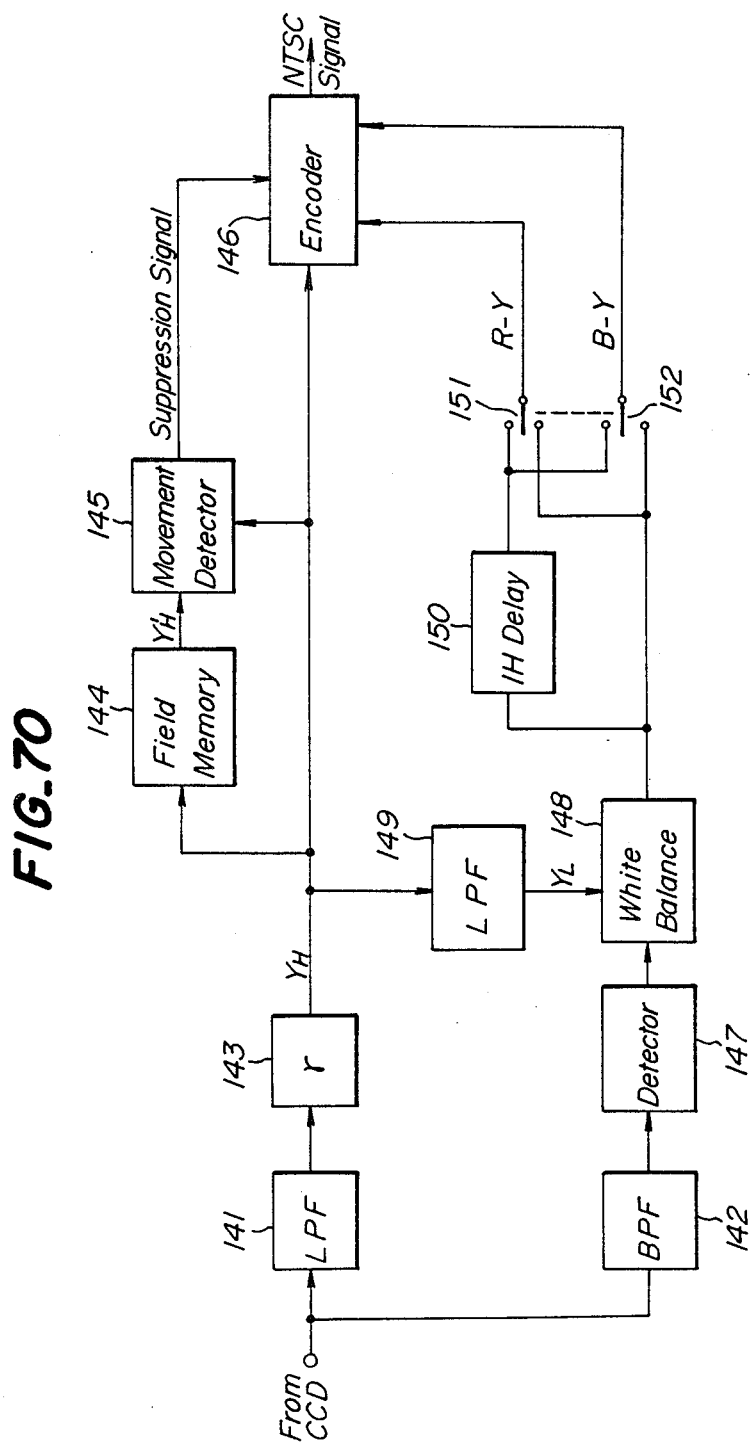
FIG. 70 is a block diagram illustrating an embodiment of the video processing circuit of the video endoscope apparatus according to the invention.

FIG. 70 is a clock diagram illustrating a signal processing circuit provided in the video processor unit 118, which circuit suppresses the color signal at the edge of the moving object by comparing the brightness signal components $Y_H$ for successive fields to derive an amount of the movement. The output signal from CCD is supplied parallelly to low pass filter 141 and band pass filter 142 to separate brightness and color signals from each other. The brightness signal separated by LPF 141 is passed through a $\gamma$ correction circuit 143 to attain a desired tonal property. The brightness signal $Y_H$ supplied from the $\gamma$ correction circuit 143 is stored in a field memory 144 which functions to delay the brightness signal for one field period. The brightness signal $Y'_H$ delayed for one field period is supplied to a movement detection circuit 145 together with the non-delayed current brightness signal $Y_H$. The movement detection circuit 145 compares the delayed and nondelayed brightness signals $Y'_H$ and $Y_H$ to detect the movement in the image. The movement detection circuit 145 supplies a movement detection signal to an encoder 146 as a color suppression signal.

The color signal separated by the band pass filter 142 is supplied to a detection circuit 147 to detect the color component. When CCD is of a inter-line type, color difference signals are appeared on alternate lines. The color difference signals are supplied to a white balance circuit 148 to achieve the white balance at respective color temperatures. Low frequency component $Y_L$ of the brightness signal $Y_H$ is also supplied to the white balance circuit 148 by means of a low pass filter 149. The color difference signals from the white balance circuit 148 is supplied to an 1H delay 150 for delaying the color difference signals by one horizontal scanning period H. Then the output signals from the white balance circuit 148 and 1H delay 150 are supplied to switches 152 and 153 which are driven at the horizontal scanning period H such that the switches 152 and 153 always derive R-Y and B-Y color difference signals, respectively. These color difference signals R-Y, B-Y are supplied to the encoder 146. In this manner, the encoder 146 receives the brightness signal $Y_H$, the Color difference signals R-Y, B-Y and the color suppression signal generated from the movement detection circuit 145.

Now the operation of the circuit will be explained also with reference to waveforms shown in FIGS. 71A to 71E. FIGS. 71A and 71B show the delayed brightness signal $Y'_H$ and the non-delayed brightness signal $Y_H$, and FIG. 71C represents the difference between the delayed and the non-delayed brightness signals. The movement detection circuit 145 produces the difference signal shown in FIG. 71C as the color suppression signal. If the color suppression is not effected, the pseudo signal might be produced at the edge of the moving object as illustrated in FIG. 71D. FIGS. 71D and 71E illustrate the color sub-carrier. In the present embodiment, as shown in FIG. 71E the color sub-carrier is suppressed by means of the color suppression signal depicted in FIG. 71C so that the amplitude of the sub-carrier is decreased to remove the pseudo signal. In this manner, although the objective lens system and the solid state image sensor are mutually vibrated, the generation of the pseudo signal can be effectively avoided.

FIG. 72 is a schematic view showing the construction of a thirty ninth embodiment of the endoscope apparatus according to the invention. In the present embodiment, use is made of the optical endoscope 1 comprising the eyepiece section 2, operation section 3 and insertion section 4. In the distal end 9 of insertion section 4, there is provided a first driving device 161 for causing the relative vibration movement between the objective lens system 11 and the entrance end 12a of image guide 12. In the present embodiment, the exit end 12b of image guide 12 and the eyepiece lens system 13 are fixed. To the eyepiece section 2 a television camera attachment 162 including a solid state image sensor, i.e. CCD 163 is detachably secured. In the television camera attachment 162, there is further provided a second driving device 164 for vibrating CCD 163. The first and second driving devices 161 and 164 may be formed by any suitable driving mechanism such as the piezo-electric vibrating element, permanent magnet and solenoid. The first and second driving devices 161 and 164 are connected to a vibration control circuit 165 so that there are produced the vibration movements in the distal end 9 of insertion section 4 and the television camera attachment 162 in the same direction at the same amplitude, frequency and phase. In this manner, the black mesh due to the image guide 12 and the Moire fringe due to the interference between the image guide and CCD can be effectively removed and further the resolution can be increased.

In the embodiment shown in FIG. 72, the vibration-movements are effected both at the distal end and the television camera attachment, but according to the invention it is also possible to effect the vibration movement at one of the distal end of insertion section and the television camera attachment.

FIG. 72 is a cross sectional view showing schematically the construction of a fortieth embodiment of the endoscope apparatus according to the invention, in which the vibration movement is taken place only at the distal end of insertion section.

In the fortieth embodiment shown in FIG. 73, the elongated piezo-electric bimorph 15 is arranged in the distal end 9 of insertion section 4, and one end of bimorph is secured to the flange 32c of guard pipe 32 accommodating the entrance end 12a of image guide 12 and the other end is secured to the hard tip member 17. Therefore, the entrance end 12a of image guide 12 is vibrated in the direction substantially perpendicular to the optical axis O. In the operation section 3, the guard pipe 62 accommodating the exit end 12b of image guide 12 is fixed to the hard member 21. In the television camera attachment 162, the CCD 163 is fixed to a hard member 16c constituting the housing of attachment 162.

In the forty first embodiment illustrated in FIG. 74, both the entrance and exit ends 12a and 12b of image guide 12 are fixed to the hard members 17 and 21, respectively. In the television camera attachment 162, an elongated piezo-electric bimorph 167 is arranged and one end of the bimorph is secured to CCD 163 and other end is connected to the hard member 166 of the attachment 162. By driving the bimorph 167, CCD 163 is vibrated in the direction substantially perpendicular to the optical axis.

FIGS. 75 and 76 are schematic views showing forty second and forty third embodiments of the endoscope apparatus according to the invention. In these embodiments, the piezo-electric elements for causing the vibration movement are energized with a voltage obtained from a secondary coil of an insulating transformer inherently provided in the light source unit.

In the embodiment shown in FIG. 75, a lens element 11a of the objective lens system 11 is vibrated in the direction substantially perpendicular to the optical axis O by means of the bimorph 15. Similarly, a lens element 13a of the eyepiece lens system 13 is vibrated substantially perpendicularly to the optical axis O by means of the bimorph 19. To the eyepiece section 2 is detachably secured a still camera attachment 171 which takes a photograph of the image of the object transmitted through the objective lens system 11, image guide 12 and eyepiece lens system 13 on a photographic film 172.

The light source unit 82 comprises an insulating transformer 173 whose primary coil is connectable to the commercially available power supply line by means of a socket 174. The primary coil of insulating transformer 170 is connected to a D.C. power supply circuit 175 which is connected to a DC/AC converter 17b provided in the operation section 3 by means of a conductor 177 extended in the universal code 5 and the connector 6. From the A.C. voltage generated by the secondary coil of insulating transformer 173 there is derived D.C. voltage of 24 V by means of the D.C. power supply circuit 175. Then, the DC/AC converter 176 generates the A.C. driving voltage having the frequency of the commercially available A.C. power supply voltage, i.e. 50 Hz or 60 Hz. The driving voltage thus generated is applied to the bimorphs 15 and 19 to vibrate the lens elements 11a and 13a of the objective and eyepiece lens systems 11 and 13 in the direction substantially perpendicular to the optical axis O, so that the black mesh and Moire fringe can be removed and the resolution can be improved.

The still camera attachment 171 comprises a control circuit (CT) 178 for controlling shutter, stop and motor, and an I/O circuit 179. When the still camera attachment 171 is secured to the eyepiece section 2 of the endoscope 1, the control circuit 178 is connected to the conductor 177 so that the D.C. voltage is applied to the control circuit 178. The light source unit 82 further comprises an exposure control circuit (EC) 180, an illumination lamp 181 and an I/O circuit 182. When the connector 6 is connected to the light source unit 82, the entrance end of light guide 33 is faced to the illumination lamp 181. The control circuit 178 in the still camera attachment 171 is connected to the exposure control circuit 180 by means of the I/O circuit 179, conductor 183 and I/O circuit 182. The exposure control circuit 180 controls the illumination lamp 181 as well as the control circuit 178 in the still camera attachment 171 such that the image of the object can be taken on the film 172 in the correct manner.

In the present embodiment, the voltage derived from the secondary coil of the insulating transformer 173 provided in the light source unit 82 can be advantageously utilized to drive the bimorphs 15 and 19 as well as the still camera attachment 171, and therefore, the whole endoscope apparatus can be made small in size, simple in construction and cheap in cost. Moreover, the endoscope apparatus can be handled easily.

In the embodiment illustrated in FIG. 76, the illumination lamp 181 and the bimorphs 15 and 19 are directly driven by the A.C. voltage obtained from the secondary coil of the insulating transformer 173 inherently provided in the light source unit 82. In this manner, the D.C. power supply circuit 175, DC/AC converter 176 and the exposure control circuit 180 in the embodiment shown in FIG. 75 are dispensed with, and the endoscope apparatus can be further made small in size and cheap in cost.

FIGS. 77, 78A and 78B illustrate the construction of the distal end of insertion section of a forty fourth embodiment of the endoscope according to the invention. FIG. 77 is a lateral cross sectional view and FIGS. 78A and 78B are longitudinal cross sectional views cut along a line A—A in FIG. 77. In the present embodiment, in order to attain the necessary amplitude of the vibration motion by means of piezo-electric elements having a shorter length under the lower driving voltage, a plurality of piezo-electric elements are arranged such that they are at least partially overlapped with each other. In the present embodiment, two elongated bimorphs 15a and 15b are arranged in the direction of the optical axis O, these bimorphs being arranged one above the other in the direction perpendicular to the optical axis O. One end of the bimorph 15a is secured to the outer surface of the guard pipe 32 accommodating the entrance end 12a of image guide 12 and the other end is secured to an inner wall of a first supporting ring 191. One end of bimorph 192 is secured to the outer wall of first supporting ring 191 and the other end is connected to an inner wall of a second supporting ring 192. As clearly shown in FIG. 77 the first and second supporting rings 191 and 192 are arranged concentrically with the guard pipe 32.

By applying the driving voltage to the bimorphs 15a and 15b, the bimorphs are bent as illustrated in FIG. 78B so that the entrance end 12a of image guide 12 is vibrated in the direction substantially perpendicular to the optical axis O as depicted by a double headed arrow in FIG. 78B. In this case, an amount of the displacement of the image guide 12 is equal to a sum of amounts of the displacement of the bimorphs 15a and 15b, so that the image guide can be vibrated with the desired amplitude by means of the bimorphs having shorter length. Further, the amplitude of the driving voltage is not necessary to be large, so that the safety can be attained.

FIG. 79 is a cross sectional view showing the construction of a forty fifth embodiment of the endoscope according to the invention. In some embodiments of the endoscopes according to the invention, the vibration movement is effected at the distal and proximal ends of insertion section in order to remove the black mesh and Moire fringe. In this case, in order to achieve the desired effect, the amplitudes of the vibrations at both ends have to be made equal to each other. However in practice, it is sometimes difficult to vibrate, for instance the entrance end and exit end of image guide at the same amplitude. In the present embodiment, the amplitudes of the vibration movements at the distal end and proximal end of insertion section can be precisely made identical with each other by providing amplitude limiting members of simple construction. As shown in FIG. 79, in the distal end of insertion section, there are arranged two bimorphs 15a and 15b in opposition to each other with respect to the guard pipe 32 accommodating the entrance end 12a of image guide 12. One ends of bimorphs 15a and 15b are secured to the outer surface of guard pipe 32 and the other ends are coupled with the hard tip member 17. To the hard tip member 17 there is further secured an amplitude limiting ring 195. Similarly, bimorphs 19a and 19b are arranged in the hole formed in the hard member 21, and one ends of bimorphs are secured to the outer surface of guard pipe 62 accommodating the exit end 12b of image guide 12 and the other ends are connected to the hard member 21. To the hard member 21 there is further secured an amplitude limiting ring 196. A distance $d_1$ between the guard pipe 32 and the amplitude limiting ring 195 is made equal to a distance $d_2$ between the guard pipe 62 and the amplitude limiting ring 196. Therefore, when the bimorphs 15a, 15b and 19a, 19b are driven, the entrance end 12a and exit end 12b of image guide 12 are vibrated in the direction shown by double headed arrows by the same amount. It should be noted that the amplitude of the driving voltage for the bimorphs has to be determined such that if the amplitude limiting rings 195, 196 are not provided, the entrance end 12a and exit end 12b of image guide 12 are moved slightly beyond the amplitude limiting rings.

FIG. 80 is a cross sectional view showing a first modification of the embodiment illustrated in FIG. 79. In the present embodiment, the amplitude limiting rings 195 and 196 are secured to the hard members 17 and 19, respectively at positions closer to the objective lens system 11 and eyepiece lens system 13, respectively. Further, the orientation of the bimorphs 15a, 15b and 19a, 19b is reversed with respect to that of the embodiment shown in FIG. 79. That is to say, the free ends of bimorphs 15a, 15b are secured to the guard pipe 32 at positions closer to the objective lens system 11.

FIG. 81 is a cross sectional view showing a second modification of the embodiment of FIG. 79. In this modified embodiment, at one ends of the guard pipes 32 and 62 remote from the objective lens system 11 and the eyepiece lens system 13, respectively, there are formed flange-like amplitude limiting projections 32d and 62d, respectively.

FIG. 82 is a cross sectional view depicting a third modification of the embodiment shown in FIG. 79. In this embodiment, the flange-like amplitude limiting projections 32d and 62d are provided at that ends of guard pipes 32 and 62 which are closer to the objective lens system 11 and eyepiece lens system 13, respectively. It should be noted that the orientation of the bimorphs 15a, 15b and 19a, 19b is reversed to that shown in FIG. 81.

FIG. 83 is a schematic view showing the construction of a forty sixth embodiment of the endoscope apparatus according to the invention. In case of inspecting the image of the object with the naked eye by means of the optical endoscope, it is sometimes desired not to cause the vibration movement, because the contrast of the image is decreased. However in case of monitoring the endoscopic image of the object with the aid of the solid state image sensor, it is always desired to effect the vibration movement in order to avoid Moire fringe. In the present embodiment, when the television camera attachment is secured to the eyepiece section of endoscope, the vibration movement is automatically effected. The entrance end 12a of image guide 12 is vibrated relative to the objective lens system 11 by means of the bimorph 15 and the exit end 12b of image guide is vibrated relative to the eyepiece lens system 13 by means of the bimorph 19. The bimorphs 15 and 19 are connected to the driving voltage generator 81 provided in the light source unit 82. As illustrated in FIG. 84, the one end of bimorph 15 is secured to the guard pipe 32 accommodating the entrance end 12a of image guide 12 by means of the spacer 16. In the outer surface of the guard pipe 32 there is formed a flattened portion 32e and the bimorph 15 is extended along this portion, while a small space is formed therebetween. Therefore, the distal end of insertion section can be made much smaller and the load to the bimorph can be reduced. To the eyepiece section 2 of endoscope 1 is detachably secured the television camera attachment 162 having CCD 163. The CCD 163 is connected to the video processor unit 118 arranged separately from the light source unit 82, and the image is displayed on the monitor 119. The eyepiece section 2 and television camera attachment 162 include electric contacts 197a, 197b and 198a, 198b, respectively, these contacts being connected to each other when the attachment 162 is secured to the eyepiece section 2. The television camera attachment 162 includes a resistor R2 connected across the contacts 198a and 198b. The light source unit 82 further comprises a comparator 199 whose one input is connected to the supply voltage V via a resistor R1, the other input being connected to a reference potential $V_{ref}$. The contact 197a is connected to the ground potential and the contact 197b is connected to the one input of comparator 199, when the universal code 5 is connected to the light source unit 82.

When the television camera attachment 162 is secured to the eyepiece section 2 of endoscope 1, the contacts 197a 197b are connected to the contacts 198a, 198b so that the potential at a connection point P between the resistors R1 and R2 is decreased than the reference potential $V_{ref}$. Then, the comparator 199 produces the signal to the driving signal generator 81 and the generator begins to supply the driving voltage to the bimorphs 15 and 19. Therefore, the distal end 12a and proximal end 12b of image guide 12 are vibrated in the same direction at the same amplitude, frequency and phase. In this manner, it is possible to display on the monitor 119 the image of object free from the Moire fringe and black mesh. When the television camera attachment 162 is removed from the eyepiece section 2, the potential at the point P is increased to the supply voltage +V higher than the reference potential $V_{ref}$. Then, the comparator 199 does not ignite the driving signal generator 81, and thus the bimorphs 15 and 19 are not vibrated. In this manner, the operator can inspect the image of the object having the high contrast. It should be noted that the decrease in contrast of the image due to the vibration movement can be compensated for electrically, so tat the image displayed on the monitor has the high contrast. It should be further noted that the connection of the television camera attachment can be detected by means of any detecting device other than that shown in FIG. 83. For instance, a switch provided in the eyepiece section may be actuated by a projection provided on the television camera attachment.

Figure 85:
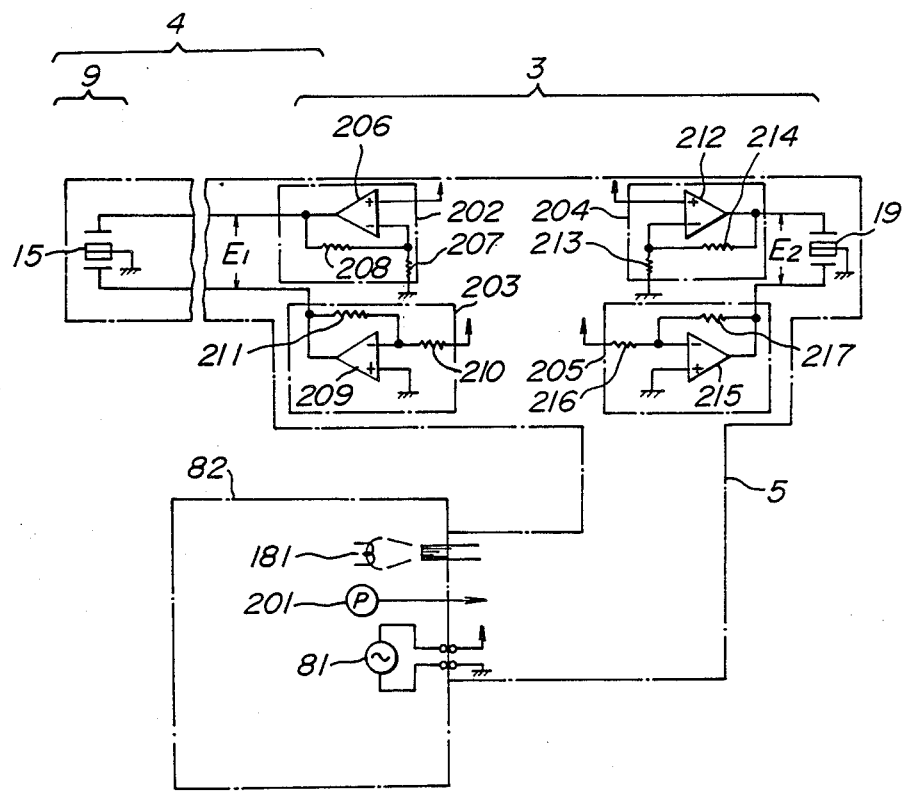
FIG. 85 is a schematic view showing a forty seventh embodiment of the endoscope according to the invention.

In the embodiments shown in FIGS. 39 and 40, the bimorphs 15 and 19 are driven by means of the single driving signal generator 81 so that the bimorphs are vibrated at the amplitude, frequency and phase. However, in practice, these bimorphs are not always vibrated in the same manner. Then, it is difficult to remove the black mesh and Moire fringe sufficiently. In a forth seventh embodiment shown in FIG. 85, in order to avoid such a drawback, variable amplifiers are arranged in respective conductors connected the bimorphs. As illustrated in FIG. 85, the light source unit 82 comprises the common driving signal generator 81 in addition to the light source 181 and a pump 201 for supplying the air/water into the distal end 9 of insertion section 4. The driving signal generator 81 generates the driving voltage which is applied to tee bimorphs 15 and 19 by means of variable gain control circuits 202-205.

Each of the variable gain control circuits comprises a differential amplifier and two resistors, but their connection is somewhat different from each other. That is to say, the variable gain control circuit 202 and 204 comprise differential amplifiers 206 and 212 whose positive inputs are connected to the output of the driving signal generator 82, the negative inputs being connected to the ground potential by means of resistors 207 and 213, respectively as well as to the outputs of differential amplifiers via resistors 208 and 214, respectively. In the variable gain control circuits 203 and 205, negative inputs of differential amplifiers 209 and 215 are connected to the output of the driving signal generator 81 via resistors 210 and 216, respectively as well as to outputs of differential amplifiers 209 and 215 by means of resistors 211 and 217, respectively. The positive inputs of differential amplifiers 209 and 215 are connected to the ground potential.

It should be noted that an amount (d) of the bending displacement of the bimorph having a length (l) under the driving voltage (E) can be represented as follows;

$$d = kl^2 E$$

wherein k is a constant. Now it is assumed that the resistors 207, 208, 210, 211, 213, 214, 216 and 217 have resistance values of R207, R208, R210, R211, R213, R214, R216 and R217, respectively. Then, amplification factors A202-A205 of the gain control circuits 202-205 are represented as follows.

$$A202 = R208/R207 + 1$$

$$A203 = R211/R210$$

$$A204 = R214/R213 + 1$$

$$A205 = R217/R216$$

It is further assumed that the length (L) of the bimorph 15 is a half of the length (2L) of the bimorph 19 and the driving voltages $E_1$ and $E_2$ are applied to the bimorphs 15 and 19, respectively. In order to vibrate the bimorphs 15 and 19 over the same amplitude, the following equation has to be satisfied.

$$K(L)^2 E_1 = k(2L)^2 E_2$$

Therefore, the resistance values of the resistors have to be so selected that $E_1 = 4E_2$ is satisfied. In this manner, by suitably selecting the resistance values, the bimorphs 15 and 19 can be vibrated at the same amplitude although the loads applied to the bimorphs are different from each other. In the embodiment shown in FIG. 85, the gain control circuits 202 and 203 are inserted in the conductors connected to respective, and therefore the bimorphs 15 and 19 can be vibrated symmetrically with respect to the stationary position. However, if it is allowed to vibrate bimorph non-symmetrically, a gain control circuit may be inserted to one of the conductors connected to the bimorph.

According to one aspect of the invention, a part of the lens system is vibrated in the direction substantially perpendicular to the optical axis in order to improve the resolution. In this case, it is desired to make the weight of the lens part to be vibrated as light as possible. That is to say, in preferable embodiments of the endoscope according to the invention, only one or more lens elements which contribute to the improvement in the resolution in the most efficient manner are vibrated.

FIG. 86 is a cross sectional view illustrating the construction of the distal end of insertion section of a forty eighth embodiment of the endoscope according to the invention. In this embodiment, the objective lens system 11 comprises a first lens group formed by a single flat-concave lens 11a and a second compound lens group consisting of a convex lens 11b and a meniscus lens 11c. the objective lens system 11 further comprises a stop 11d. The lens element 11a is held by the cylinder 31a which is secured to the hard tip member 17, and the compound second lens group 11b, 11c is supported by the cylinder 32. When the second lens group 11b, 11c is moved in the direction perpendicular to the optical axis O, the optical axis is varied to a large extent. Therefore, one end of bimorph 15 is secured to the guard pipe 32 accommodating the entrance end 12c of image guide 12 and the other end is secured to the hard tip member 17 by means of the supporting member 73.

FIG. 87 is a schematic cross sectional view illustrating the construction of the distal end of insertion section of a forty ninth embodiment of the endoscope according to the invention. In this embodiment, the objective lens system 11 comprises the flat-concave lens 11a, the compound lens 11b, 11c, stop 11d and a plane parallel plate 11e. The plane parallel plate 11e is arranged in the cylinder 31a such that the plate is inclined with respect to the optical axis O. The free end of bimorph 15 is secured to the cylinder 31a. Therefore, by swinging the plane parallel plate 11e as shown by a double headed arrow by means of the bimorph 15, the optical axis is varied between a range denoted by dotted lines $L_1$ and $L_2$, so that the image of object formed by the lenses 11a-11c is shifted on the entrance surface of image guide 12.

FIG. 88 is a cross sectional view depicting a modification of the embodiment illustrated in FIG. 87. In this embodiment, one end of the laminated type piezo-electric element 55 is connected to the cylinder 31a holding the plane parallel plate 11e, and the other end is secured to the hard tip member 17. When the element 55 is driven, the plane parallel plate 11e is vibrated in the direction of the optical axis O as shown by an arrow A so that the image of object projected on the entrance end surface of image guide 12 is reciprocally shifted in the direction perpendicular to the optical axis O as illustrated by an arrow B.

FIG. 89 is a cross sectional view showing the construction of the distal end of insertion section of a fiftieth embodiment of the endoscope according to the invention. In the present embodiment, the second lens group 11b, 11c serves to change the focus position. Therefore, by moving the second lens group 11b, 11c in the direction of the optical axis O by means of the laminated type piezo-electric element 55 as shown by an arrow A, the focus position of the image of object formed by the objective lens system 11 is vibrated in the direction of the optical axis O with respect to the entrance end surface of image guide 12. The, the focal depth of the objective lens system 11 becomes increased and the resolution in the direction of the optical axis is improved. It is advantageous to combine the change in the angle of view with the change in the focus position.

FIG. 90 is a schematic view illustrating the construction of fifty first embodiment of the endoscope according to the invention. As stated above, in order to remove the black mesh and Moire fringe and to improve the resolution, the vibration movements at the distal end and proximal end of insertion section has to be made identical. That is to say, for instance, the entrance end and exit end of image guide have to be vibrated in synchronism with each other. In the present embodiment, in order to attain the synchronous movement, there are provided sensors for detecting the vibration movements at both the ends and the phases of driving voltages applied to the bimorphs are controlled in accordance with output signals from the vibration sensors. The endoscope 1 comprises the bimorphs 15 and 19 for vibrating the entrance and exit ends of image guide. Near the respective ends of image guide there are arranged vibration sensors 221 and 222. The light source unit 82 comprises a reference oscillator (OSC) 223 for generating a reference signal shown in FIG. 91A. The reference signal is supplied parallelly to phase locked loops (PLL) 224 and 225 to which output signals generated by the sensors 221 and 222 are also supplied, respectively. Output signals from PLLs 224 and 225 are supplied to voltage controlled oscillators (VCO) 226 and 227, respectively as the frequency control voltage. The VCOs 226 and 227 are connected to the bimorphs 15 and 19, respectively so that the bimorphs are driven by the output voltages generated from VCOs 226 and 227, respectively.

When the output signals from the vibration sensors 221 and 222 are phase-shifted with respect to the reference signal as shown by broken lines in FIGS. 91B and 91C, PLLs 224 and 225 operate to reduce the phase differences, until the phase of output signals from the vibration sensors become identical with that of the reference signal. In this manner, the phases of the vibration movements at the distal end and proximal end of insertion section are always kept identical with each other.

FIGS. 92 and 93 are cross sectional views depicting the construction of the distal end and proximal end of insertion section in the present embodiment. The vibration sensors 221 and 222 comprise light emitting parts 221a, 222a, light reflecting plates 221b, 222b secured to the guard pipes 32 and 62, respectively and light receiving parts 221c, 222c which receive light fluxes reflected from the reflecting plates 221b, 222b. When the entrance end 129 of image guide 12 is vibrated in the direction substantially perpendicular to the optical axis O as represented by an arrow A, the beam spot reflected by the mirror plate 221b and received the light receiving portion 22c is moved on the light receiving portion in a direction of the optical axis O. In this manner, the light receiving portion 211c produces the output signal which represent the position of the entrance end 12a of image guide 12 during the vibration movement.

FIG. 94 is a schematic view showing a modification of the embodiment shown in FIG. 92. In the present embodiment, the circuits 223-227 for controlling the vibration movements of the bimorphs 15 and 19 are provided in the operation section 3 of endoscope 1. The remaining construction is the same as the previous embodiment and its explanation is omitted.

In the above explained embodiment shown in FIGS. 23A and 23B, the entrance end 12a of image guide 12 is vibrated in two different directions by means of the two bimorphs 15a and 15b. However, in this case the free ends of bimorphs 15a, 15b are secured directly to the guard pipe 32 accommodating the entrance end 12a of image guide 12 so that each bimorphs show resistance against the bending motion of other bimorphs. That is to say, the bimorph is hardly bent in a direction perpendicular to the bending direction. For instance, the first bimorph 15a shown in FIG. 23A is hardly bent in the direction perpendicular to the plane of the drawing of FIG. 23A, and the second bimorph 15b is hardly bent in the direction parallel to the plane of the drawing. Therefore, the entrance end of image guide could not be vibrated efficiently. According to further aspect of the invention, the above drawback can be mitigated by providing an intermediate vibration member, and arranging the first and second bimorphs in a space between the image guide and intermediate vibration member and the hard tip member, respectively.

Figure 95:
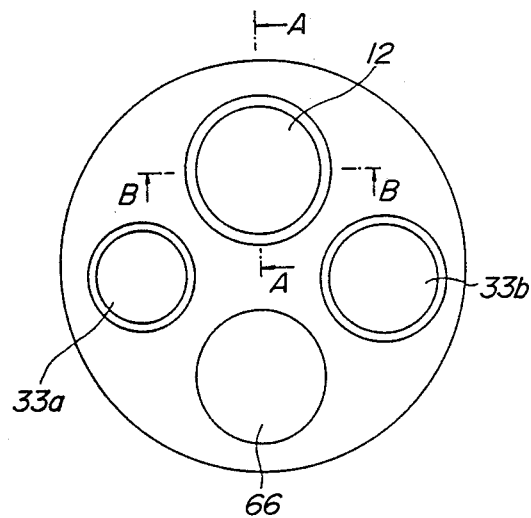
FIG. 95 is a front view of the distal end of insertion section of a fifty second embodiment of the endoscope according to the invention.
Figure 96:
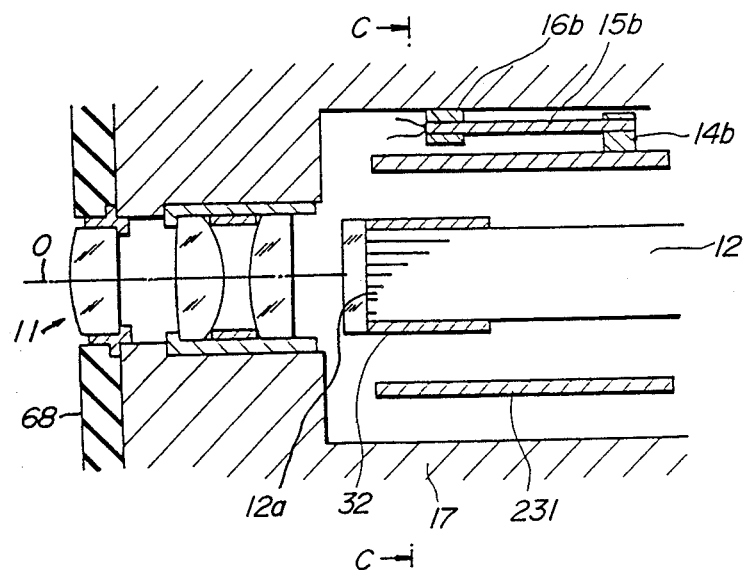

FIGS. 95-98 show the construction of a fifty second embodiment of the endoscope according to the invention. FIG. 95 is a front view of the distal end of insertion section, FIGS. 96 and 97 are cross sectional views cut along lines A—A and B—B, respectively in FIG. 95, and FIG. 98 a cross section cut along a line C—C in FIG. 96. The first bimorph 15a is arranged in a space between the image guide 12 and an intermediate vibration member 231 formed by a sleeve and the second bimorph 15b is provided in a space between the intermediate vibration member 231 and the hard tip member 17. The fee end of first bimorph 15a is secured to the guard pipe 32 via the spacer 14a and the other end is secured to the inner surface of intermediate vibration member 231 by means of the spacer 16a. The fee end of second bimorphs 15b is secured to the outer surface of intermediate vibration member 231 by means of the spacer 14b and the other end is connected to the hard tip member 17 via the spacer 16b. Then, by driving the first bimorph 15a, the entrance end 12a of image guide 12 is vibrated in a first direction perpendicular to the optical axis O and when the driving voltage is applied to the second bimorph 15b, the entrance end 12a of image guide 12 is vibrated together with the intermediate vibration member 231 in a second direction which is perpendicular to the optical axis O and the first direction. Therefore, by driving the first and second bimorphs 15a and 15b simultaneously, the entrance end 12a of image guide 12 can be moved reciprocally along any desired locus such as circular and ellipse.

Figure 99:
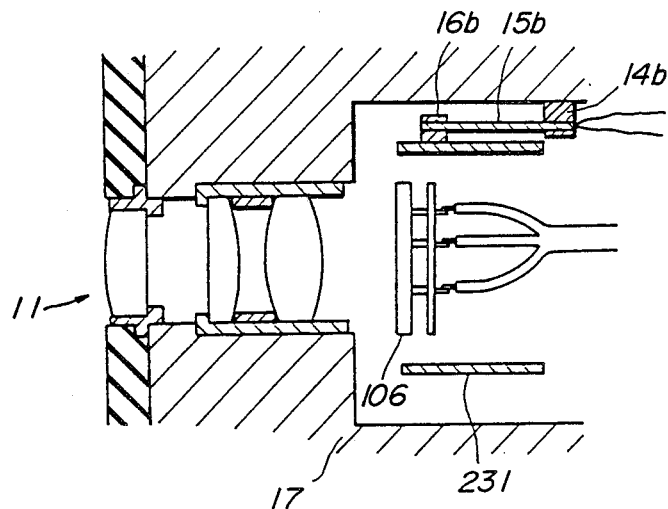
FIGS. 99 and 100 are cross sectional views depicting the distal end of insertion section of a fifty third embodiment of the endoscope according to the invention.
Figure 100:
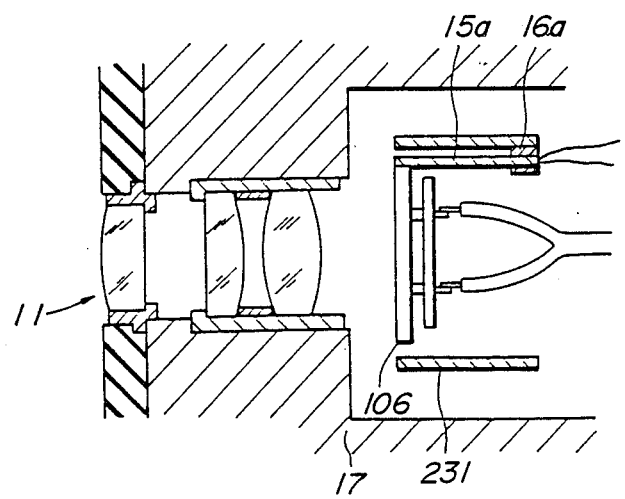

FIGS. 99 and 100 are cross sectional view illustration the construction of the distal end of insertion section of a fifty third embodiment of the video endoscope according to the invention. In the present embodiment, the CCD 106 arranged in the distal end of insertion section is vibrated in two orthogonal directions by means of the first and second bimorphs 15a and 15b with the aid of the sleeve-like intermediate vibration member 231.

FIG. 101 is a block diagram showing the driving circuit for the bimorphs 15a, 15b and CCD 106. The driving circuit includes a synchronizing signal generator 232 for generating synchronizing signals which are supplied to a CCD driving signal generating circuit 233. Then the CCD driving signal generating circuit 233 supplies the driving signal including horizontal and vertical transfer pulses and reset pulse to CCD 106. The synchronizing signal generated from the synchronizing signal generator 232 is also supplied to driving voltage generating circuit 234 which supplies the driving voltages to the first and second bimorphs 15a and 15b for driving CCD 106 in orthogonal directions. In this case, the first bimorph 15a serves to vibrate CCD in the horizontal direction over a distance equal to a half of a horizontal pitch l of pixels, and the second bimorph 15b operates to vibrate CCD in the vertical direction over a distance equal to a half of a vertical pitch m of pixels as illustrated in FIG. 102A. Therefore, the pixel $A_{11}$ is moved into positions $B_{11}$, $D_{11}$ and $C_{11}$ successively. Therefore, the number of pixels is equivalently increased by four times and the resolution can be improved. FIGS. 102B and 102C illustrate the waveforms of the driving voltages applied to the first and second bimorphs 15a and 15b, respectively. The repetition period of the driving voltage for the first bimorph 15a is a half of that for the second bimorph 15b.

FIGS. 103 and 104 are cross sectional views showing the construction of the distal end of insertion section of a fifty fourth embodiment of the endoscope according to the invention. In the present embodiment, use is made of a rod-like intermediate vibration member 23 instead of the sleeve-like intermediate vibration member 231. The free end of first bimorph 15a is secured to the guard pipe 32 via the spacer 14a and the other end is secured to the rod-like intermediate vibration member 235 to which the free end of second bimorph 15b is also secured. As best shown in FIG. 104 the first and second bimorphs 15a and 15b are extended in the orthogonal planes.

Particularly, at the eyepiece side, the positional relation between the image guide and the eyepiece lens system has to be precisely set because the magnification of the eyepiece lens system has to be large and the objective lens system has to be moved in the direction of the optical axis for adjusting the visibility. If the positional relation between the image guide and the eyepiece lens system is slightly deviated from the ideal condition, the sharpness of the image is lost and the resolution could not be improved even by causing the vibration movement. In this case, the position of the image guide may be directly adjusted, but then it is necessary to provide an adjusting mechanism between the image guide and the bimorph and the whole construction becomes quite complicated. According to another aspect of the invention, the above mentioned problem can be solved by providing a fitting frame to which the fixed end of bimorph is secured and a supporting frame to which said fitting frame is movably secured. By this measure, the image guide can be positioned accurately and simply with respect to the eyepiece lens system.

Figure 105:
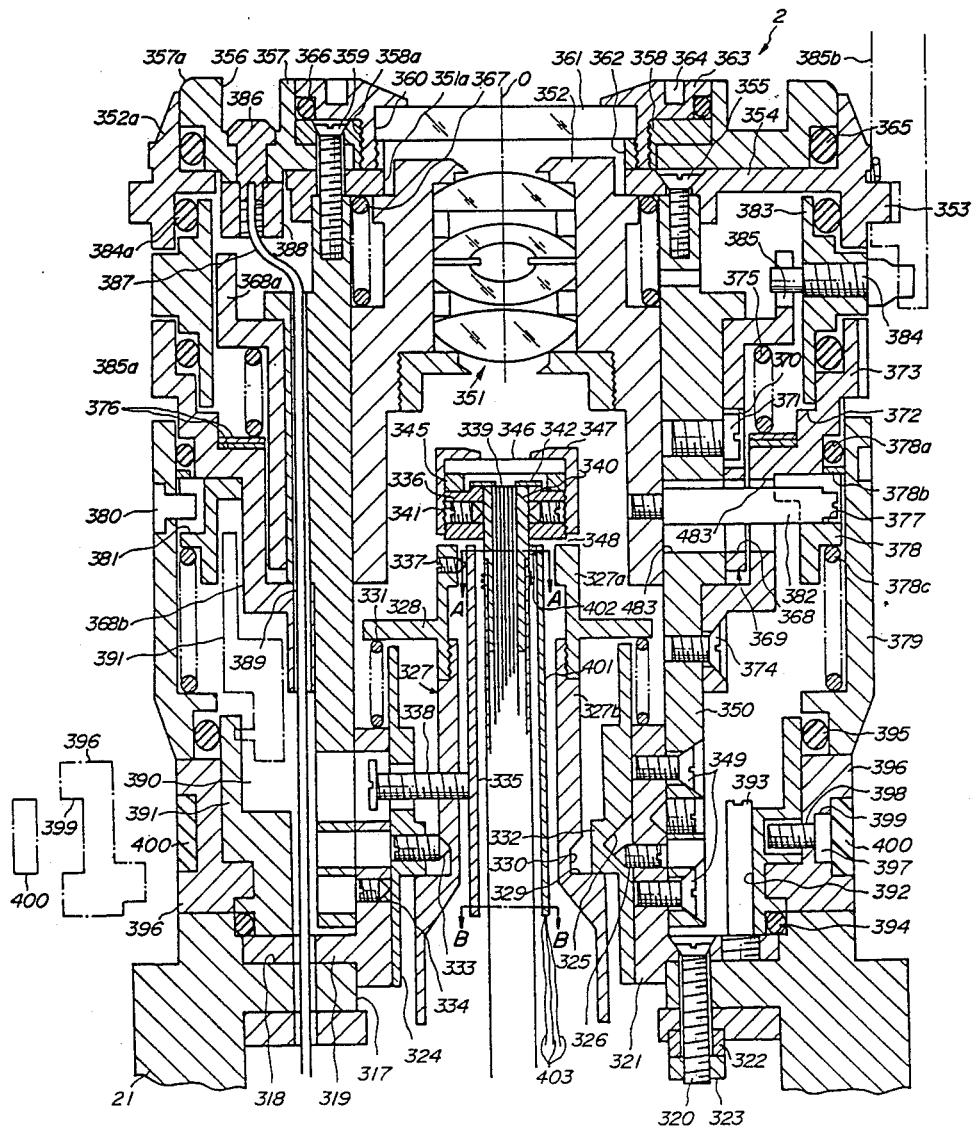
FIG. 105 is a cross sectional view illustrating the construction of the eyepiece section of a fifty fifth embodiment of the endoscope according to the invention.

FIG. 105 is a cross sectional view showing the detailed construction of the eyepiece section of a fifty fifth embodiment of the endoscope according to the invention. The eyepiece section 2 comprises a supporting sleeve 321 which is secured to the hard member 21 of the operation section with a screw 320 by means of a flange 319 which is inserted into a recess 318 formed in a fitting hole 317 formed in the hard member 316. In order to electrically isolate the eyepiece section 2, the screw 320 is secured to the hard member 21 by means of an insulating member 322 made of ceramics and a nut 323. In the supporting sleeve 321 an adjusting sleeve 324 is inserted movably in the direction of the optical axis O. In the outer surface of adjusting sleeve 324 there is formed a first recesses 325 each having a V-shaped cross section. Into the first recesses 325, conical tips of a plurality of first adjusting screws 326 are inserted, the screws being threaded through the supporting sleeve 321. Therefore, by turning the first adjusting screws 326, the adjusting sleeve 324 is displaced.

In the adjusting sleeve 324, there is inserted a holding frame 327 consisting of first and second sleeves 327a and 327b. Around the outer surface of first sleeve 327a there is formed a flange 328, and in the outer surface of second sleeve 327b there are formed a step portion 329 and second recesses 330. Between the flange 328 and the upper edge of supporting sleeve 321 there is arranged a coiled spring 331 which biases the holding frame 327 upward. The step 329 is engaged with a projection 332 formed on the inner wall of holding frame 327 for limiting the upward movement of the holding frame 327. Into the second recesses 330 are inserted conical tips of a plurality of adjusting screws 333 threaded through the adjusting sleeve 324. Therefore, by means of the first adjusting screws 326, the supporting sleeve 321 is moved together with the adjusting sleeve 324 in the axial direction, i.e. up and down directions, and by means of the second adjusting screws 333 the holding frame 327 is moved in the radial direction, i.e. in the direction perpendicular to the axial direction. In the supporting sleeve 21, there is threaded a fixing screw 334 for fixing the adjusting sleeve 324 to the supporting sleeve 321 after the adjusting sleeve has been positioned in the axial direction.

Into the holding frame 327 is inserted a fitting frame 335. The upper edge of fitting frame 335 is swingably supported by a plurality of supporting screws 337 threaded through the holding frame 327. The tilting angle of the fitting frame 335 can be adjusted by a plurality of third adjusting screws 338 threaded through the second sleeve 327a of the holding frame 327. In the fitting frame 335, the exit end of image guide 339 is freely inserted, and a guard pipe 340 accommodating the exit end of image guide 339 is clamped into a holding member 336 and is secured thereto by means of a fixing screw 341. The exit end face of image guide 339 is aligned with the upper surface of holding member 336, and a mask 342 is secured to the exit end face of image guide.

The exit end face of image guide 339 is covered with a transparent cover plate 346 by means of a spacer 345, the cover plate 346 is fixed by means of a clamping body 347 screwed to the holding member 336.

FIGS. 105 and 106 are cross sectional views cut along lines A—A and B—B in FIG. 104. The fitting frame 335 has a slit formed therein, said slit extending in the axial direction. In the slit there is arranged an elongated bimorph 401, and a free end of bimorph is secured to the guard pipe 340 via a spacer 402 and a fixing end of bimorph is secured to the fitting frame 35. The conductors 403 connected to the bimorph 401 is connected to the pulse generator. The positioning of the fitting frame 335 with respect to the holding frame 327 in the axial direction is effected by inserting a spacer (not shown) in a space 448 formed between the upper edge of holding frame 327 and the lower edge of holding member 336.

To the supporting sleeve 21 is fixed an eyepiece sleeve 350 by means of a plurality of fixing screws 347, and a lens holder 352 accommodating the eyepiece lens system 551 is inserted into the eyepiece sleeve 350 movably in the axial direction. To the upper edge of eyepiece sleeve 350 is secured a connecting plate 354 by means of screws 355, said connecting plate including a first hole 351a having a diameter smaller than that of the eyepiece sleeve 350, a peripheral wall 352a projecting in the axial direction and a plurality of claws 53 extending from the lower portion of peripheral wall. On the connecting plate 354 is secured an intermediate plate 357 having a ring-shaped recess 356 formed in its upper surface. The intermediate plate 357 is fixed to the eyepiece sleeve 350 by means of a pushing plate 358 having a female screw 358a and screws 359. The female screw 358a of plate 358 is engaged with a fitting plate 363 having a second hole 360 in which a cover glass 361 is secured with the aid of a ring 362. In the fitting plate 363 there are formed a plurality of holes 364 by means of which the fitting plate 363 can be removed from the pushing plate 358 so that the cover glass 361 can be easily exchanged. The periphery 57a of intermediate plate a 357 is ground off in order to protect the eye of user. Between the connecting plate 354 and the intermediate plate 357 is arranged a first O-ring 365, and between the intermediate plate 357 and the fitting plate 363 is inserted a second O-ring 366. Further a coiled spring 367 is arranged between the lens holder 352 and the connecting plate 354 so that the lens holder is biased downward.

Around the eyepiece sleeve 50 there is rotatably arranged a photographing cam sleeve 369 having large diameter portion 368, small diameter portion 368b and a cam hole 368 formed in the small diameter portion. In the cam sleeve 369 there is formed a rotating limit recess 370 into which is engaged a pin 371 screwed to the eyepiece sleeve 350. Around the cam sleeve 369 there is arranged a petitioning sleeve 373 having a plurality of steps 372, the petitioning sleeve being secured to the eyepiece sleeve 350 by means of a screw 374. There is inserted a coiled spring 375 between the cam sleeve 369 and the upper edge of the lower most step 372 so that the cam sleeve is biased upward. On the surface of this step 372 two ring-shaped sheets 376 made of lubricant material such as teflon are provided. Around the petitioning sleeve 373 there is rotatably arranged a cam sleeve 378 having a cam recess 377 formed therein. Around the cam sleeve 378 there is further rotatably provided a visibility adjusting ring 379 by means of a third O-ring 378a. In the adjusting ring 379 there is provided a pin 380 which is engaged with the recess 381 formed in the cam sleeve 378. Therefore, when the adjusting ring 379 is rotated, the cam sleeve 78 is rotated in conjunction therewith. At the upper edge of cam sleeve 378 there is arranged a ring 378b for preventing the O-ring 378a from being removed. The cam sleeve is biased upward with the aid of a coiled spring 378c which is stronger than the spring 367 biasing the lens holder 352 downward. Into the cam recess 377 of cam sleeve 378 there is inserted a cam pin 382 secured to the lens holder 352, the cam pin 382 extending through holes 483 formed in the eyepiece sleeve 350 and petitioning sleeve 373 and the cam hole 368 formed in the cam sleeve 369. Therefore, when the cam sleeve 398 is rotated, the cam pin 382 is moved up and down along the cam recess 397 and the lens holder 352 is moved in conjunction with the cam pin 382. Between the upper edge of petitioning sleeve 373 and the lower edge of peripheral wall 352a there is rotatably arranged a photograph ring 383 by means of fourth and fifth O-rings 384a and 385a. Through the photograph ring 383 is threaded a pin 384 whose one end is engaged with a recess 385 formed in the large diameter portion 368a of the photography cam sleeve 369. The other end of pine 384 is engaged with a photography adapter 385b which is detachably secured to the claw portion 353 of connecting plate 354. When the photography adapter 385b is rotated over a given angle in order to fix the adapter, the photography ring 383 is rotated by means of the pin 384 and then the photography cam sleeve 369 is moved in conjunction therewith. When the cam sleeve 369 is rotated, the lens holder 352 is moved upward and the eyepiece lens system 351 is also moved into the photography position from the inspection position. When a still camera is fixed to the adapter 385b, a contact pin 386 provided in the recess 356 of connecting plate 354 is connected to the camera, so that various kinds of signals can be supplied to the camera via the contact 386. A lead wire 387 is soldered to the contact 386. The folding portion is protected by an insulating ring 388. The lead wire 387 extends in a passage 389 formed in the eyepiece sleeve 350.

Between the lower edge of visibility adjusting ring 379 and the upper edge of hard member 21 of operation section, there is formed a ring-shaped space 390 into which the first, second and third adjusting screws 326, 333 and 338 can be extended. In the space 390, there is arranged a sliding sleeve 391 movably up and down, the outer diameter of sliding sleeve being slightly smaller than the inner diameter of cam sleeve 378. In the inner surface of sliding sleeve 391 there are formed a plurality of recesses 392 extending in the axial direction, and guide pins 393 secured to the flange portion 319 of supporting sleeve 321 are engaged with the recesses. Therefore, the sliding sleeve 391 can be moved up and down without being rotated along the guide pins 393. The upper and lower edges of sliding sleeve 391 is coupled with the hard member 21 and adjusting ring 399 by means of sixth and seventh O-rings 394 and 395. On the sliding sleeve 391 there is detachably provided an outer ring 396 which is divided into two sections. The outer ring sections are detachably secured to the sliding sleeve 391 by projecting screws 397 into recesses 398 formed in the sliding sleeve. In the outer surface of outer ring 396 there is formed a recess 399 into which a rubber ring 400 is clamped. The rubber ring 400 has a color identifying the kind of endoscope.

Now the adjustment will be explained. Before the fitting frame 335 is secured to the holding frame 327 by means of the screw 337, the spacer is inserted into the space 348 between the upper edge of holding frame 327 and the lower edge of holding member 336, so that the positioning of the fitting frame 335 in the rotational direction is carried out. In this manner, the deviation between the orientation of the image at the entrance end of image guide and that at the exit end of image guide can be compensated for. Then, the fitting frame 335 is secured to the holding frame 327 by means of the screw 337 and the spacer is removed from the space 348. Then the eyepiece section is composed.

Before providing the outer ring 396 on the outer surface of sliding sleeve 391, the sliding sleeve is moved upward and a space 390 is exposed. By adjusting the first adjusting screw 326, the adjusting sleeve 324 is moved up and down and the holding frame 327 is also moved up and down. In this manner, the position of the exit end face of image guide 339 can be adjusted in the axial direction. Next, by means of the second adjusting screw 333, the holding frame 327 is moved in the radial direction so that the optical axis of the image guide 339 is made coincident with the optical axis of the eyepiece lens system 351. Further, by adjusting the third adjusting screw 338, the fitting frame 335 is tilted about the screw 337 so that the exit end face of image guide 339 can be made perpendicular to the optical axis of the eyepiece lens system 351. In this manner, in the present embodiment, the three kinds of adjustments of the image guide 339 with respect to the eyepiece lens system 351 can be effected independently from each other, so that the adjustment can be carried out precisely and easily.

FIG. 108 is a cross sectional view showing the construction of the eyepiece section of a fifty sixth embodiment of the endoscope according to the invention. In the embodiment illustrated in FIG. 105, since the field limiting mask 342 is secured to the exit end face of image guide, when the image guide is vibrated, the mask is also vibrated, so that the periphery of the image might be blurred. In the present embodiment, the mask is provided on the non-vibrated member near the exit end face of image guide. That is to say, the upper end of fitting frame 335 is inserted into the holding member 336 and is secured thereto by means of the screw 341. The upper edge of fitting frame 335 is slightly projected beyond the exit end face of image guide 339, and the mask 342 is secured to the upper end face of fitting frame 335, so that there is formed a narrow space between the exit end face of image guide and the mask. When the driving voltage is applied to the bimorph 401, the exit end of image guide is vibrated in the direction substantially perpendicular to the optical axis, but the mask 342 is remained stationary. The remaining construction of the eyepiece section is entirely same as that shown in FIG. 105 and its detailed explanation is omitted.

In the embodiments in which the entrance and exit ends of image guide are vibrated, the entrance and exit ends are moved regularly, there might be observed Moire fringes. In order to mitigate this drawback, the entrance and exit ends of image guide may be moved at random.

FIG. 109 is a schematic view showing the construction of a fifty seventh embodiment of the endoscope according to the invention. In this embodiment, there is provided a random noise generator 501 and the random noise voltage is applied to the bimorphs 15 and 19 via an amplifier 502. The bimorphs 15 and 19 serve to move the entrance and exit ends 12a and 12b of image guide in the same direction. The driving voltage applied to the bimorphs 15 and 19 has the amplitude which changes at random, Moire fringe is no more visible.

FIG. 110 is a schematic view showing a modification of the embodiment illustrated in FIG. 110. In this embodiment, the entrance end 12a and exit end 12b of image guide are moved in two orthogonal directions by means of the bimorphs 15a, 15b and 19a, 19b. There are provided two random noise generators 505 and 506 and amplifiers 507 and 508. The random noise voltage generated from the generator 505 is applied via the amplifier 507 to the bimorphs 15a and 19a and the random noise voltage from the generator 506 is applied via the amplifier 508 to the bimorphs 15b and 17b.

FIG. 111 shows a modification of the embodiment shown in FIG. 110. In this embodiment, the random noise voltage generated from the random noise generator 501 is applied via the amplifier 502 to all the bimorphs 14a, 14b, 19a and 19b.

In case of inspecting the image of the object with the naked eye or the television camera, it is sufficient to cause the vibration movement of a relatively low frequency such as several tens cycles per second. However, in case of taking a photograph of a moving object with the aid of the still camera, the black mesh could not be removed sufficiently. In order to overcome such a drawback, the vibration frequency may be set to a high frequency more than 1 KHz. Then, the vibrating mechanism might wear soon. In a fifty eighth embodiment shown in FIG. 112, the vibration frequency is increased only when the photograph is taken. In this embodiment, the objective lens system 11 and eyepiece lens system 13 include plane parallel plates 11a and 13a. As clearly shown in FIG. 113, the plates 11a, 13a are clamped within frames 11b, 13b between semispherical tips 509, 510 secured to piezo-electric elements 15, 19 and dampers 511, 512, respectively.

To the eyepiece section 2 of endoscope 1, the still camera attachment 513 is detachably fixed. The still camera attachment 513 includes an imaging lens 514, shutter 515, photographic film 516 and shutter release button 517. The piezo-electric elements 15, 19 are connected to a driving signal generator 517 generating the driving voltage for the piezo-electric elements. The driving signal generator 517 is connected to a control circuit 518 to which is also connected the shutter release button 517. There is further provided a power supply circuit 519 for energizing the control circuit 518.

Now the operation will be explained with reference to waveforms shown in FIGS. 114 and 115.

When the photograph is not taken, the driving signal generator 517 generates the driving voltage being a low frequency such as 20 Hz. When the shutter release button 517 on the still camera attachment 513 is pushed, a release signal is supplied to the control circuit 518 as shown in FIG. 114B. Then, the driving signal generator 517 generates the driving signal having a higher frequency than 1 KHz, preferably about 10 KHz for a time interval during which the shutter 515 is opened as illustrated in FIGS. 114A and 114C. When it is desired to effect flash illumination, the flash lamp is ignited for a period at least equal to one cycle period of the driving signal. The flash lamp may be ignited several times during the shutter open period. Further, the light emitting period of the flash lamp is shorter than the one period of the driving signal of the high frequency, the flash lamp may be ignited several times during the one period of the driving signal as illustrated in FIGS. 115A–115D.

FIG. 116 is a schematic cross sectional view showing the construction of a fifty ninth embodiment of the endoscope according to the invention. In the present embodiment, plane parallel plates 520 and 521 arranged at the entrance and exit ends of image guide 12 is rotated by means of ultrasonic motors 522 and 523, respectively. That is to say, the plates 520 and 521 are arranged in rotors 522a and 523a which are provided in stators 522b and 523b, respectively. The stators 522b and 523b are connected to a control circuit 524 which is connected to a pulse generator 525. When the driving signal is supplied from the pulse generator 525 via the control circuit 524 to the stators 522b and 523b, the rotators 522a and 523b the rotators 522a and 523a are rotated in synchronism with each other.

FIG. 117 is a cross sectional view showing the construction of the distal end of a modification of the embodiment shown in FIG. 117. In the present embodiment, lens elements 11a–11c are fixed to the lens holder 31a, but lens elements 11d and 11e are arranged movably in the direction of the optical axis O to effect the focus adjustment. To this end, the lens elements 11d, 11e are arranged in a rotor 526a of an ultrasonic motor 526 and the rotor is arranged in a stator 526b. The rotor 526a has a projection 526c which is engaged with a spiral recess 526d formed in the inner surface of stator 526b. Therefore, when the ultrasonic motor 526 is energized by means of the circuits 524 and 525, the rotor 526a is rotated and thus is moved along the optical axis O to effect the focus adjustment. The remaining construction is the same as the embodiment shown in FIG. 117.

In the embodiments shown in FIGS. 117 and 118, the vibration movement is caused by rotating the plane parallel plate arranged in an inclined manner with respect to the optical axis. However, as illustrated in FIG. 118A, use may be made of a lens 531 having an optical axis O' shifted from the optical axis O of the image guide 12, or an optical fiber plate 523 may be obliquely arranged with respect to the optical axis O as shown FIG. 118B, or the optical fiber plate 532 may be arranged off-axis with respect to the optical axis of the image guide 12 as depicted in FIG. 118C. By rotating the above optical elements 531, 532, the image formed at the entrance end face of image guide is shifted or vibrated in the direction substantially perpendicular to the optical axis O.

Figure 119:
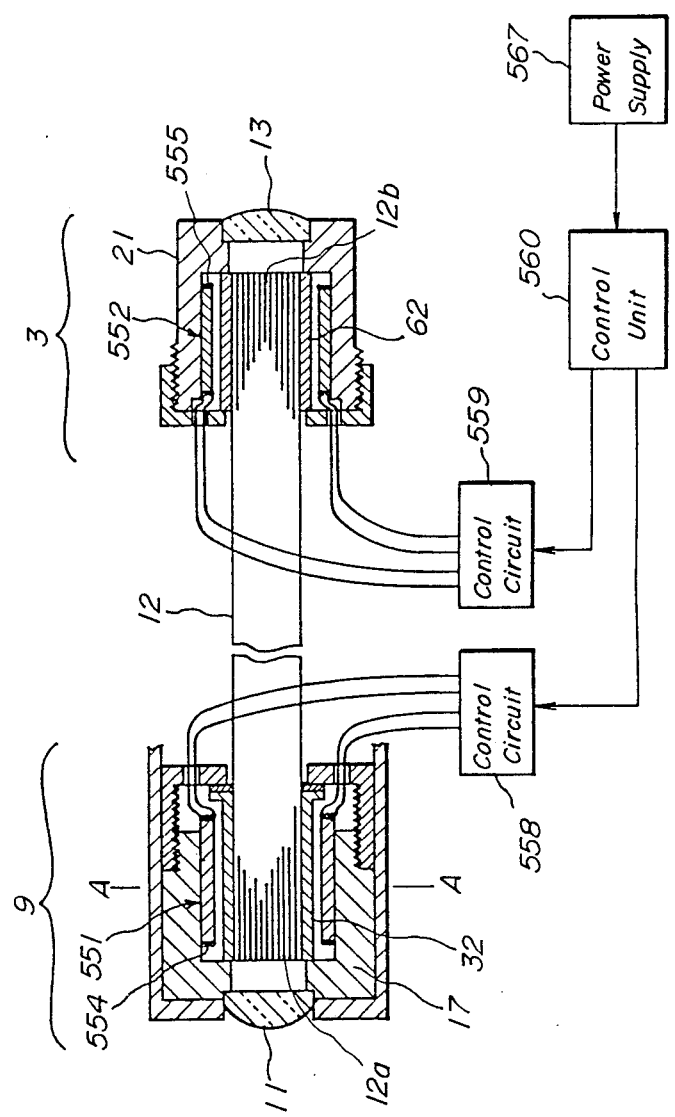
FIG. 119 is a schematic view showing the construction of a sixtieth embodiment of the endoscope according to the invention.

FIGS. 119 and 120 are schematic cross sectional views showing the construction of a sixtieth embodiment of the endoscope according to the invention. In the present embodiment, the entrance end 12a and exit end 12b of image guide 12 are moved by means of electromagnetic units 551 and 552 each having a plurality of poles. In order to rotate the image guide within the electromagnetic unit the guard pipes 32 and 62 accommodating the entrance and exit ends of image guide are made of magnetic material. As shown in FIG. 120, the electromagnetic unit 551 has a plurality of poles 553 and coils 554 are wound around respective poles. The construction of the electromagnetic unit 552 for rotating the exit end 12b of image guide 12 has the same construction.

As shown in FIG. 121, the coils 554-1~554-n of the electromagnetic unit 551 and coils 555-1~555-n of the electromagnetic unit 552 are connected to analog switches 556 and 557, respectively provided in control circuits 558 and 559, respectively. These control circuits 558 and 559 are connected to a control unit 560 comprising I/O circuit 561, CPU 562, RAM 563, ROM 564 and switch 565. The control unit 560 is connected to power source 566 provided in a power supply unit 567.

When the switch 565 provided on the operation section of endoscope, CPU 562 in the control unit 560 sends a command via the I/O circuit 561 to the analog switches 556 and 557, so that the analog switches supply the driving currents to the coils 554-1, 554-2 ... 554-n and 555-1, 555-2 ... 555-n successively in synchronism with each other. Then, the successive poles of the electromagnetic units 551 and 552 are magnetized and the guard pipes 32 and 62 are attracted to the energized poles. In this manner, the guard pipes 32 and 62 are revolved as illustrated in FIG. 122 in synchronism with each other.

It should be noted that the clearance between the guard pipe and the poles is set to 0.5–2.0 times of the diameter of the optical fiber constituting the image guide 12. When the clearance is selected to the diameter of the fiber, the fibers are moved as represented in FIG. 123. When fibers A and B are revolved, their centers trace circles a and b, respectively. That is to say, the fibers are vibrated two-dimensionally at an amplitude equal to the diameter of the fiber, so that the resolution can be improved in all directions.

FIGS. 124 and 125 are cross section showing another embodiments of the electromagnetic unit. In FIG. 124, a guard pipe 571 is formed elliptically and the poles 572 of the electromagnetic unit are arranged along also elliptically. In FIG. 125, a guard pipe 573 has a square cross section and poles 574 of electromagnetic unit are arranged along a square. It should be further noted that a sleeve made of magnetic material may be applied on the guard pipe, when the guard pipe is made of nonmagnetic material.

What is claimed is:

1. An endoscope apparatus for inspecting an object comprising
    an insertion section insertable into the object under inspection and having a distal end and a proximal end;
    an image guide arranged within the insertion section and having an entrance end arranged at the distal end of insertion section and an exit end arranged at the proximal end of insertion section;
    an objective lens system arranged at the distal end of insertion section for forming an optical image of the object onto the entrance end of image guide;
    an eyepiece lens system arranged at the proximal end of insertion section for projecting the optical image transmitted through the image guide onto an obsevating position;
    a first driving means arranged at the distal end of insertion section and including at least one piezoelectric vibrating element which extends substantially in a longitudinal direction of the insertion section for causing a first vibrating movement of the optical image formed by the objective lens system and the entrance end of image guide relative to each other over a predetermined distance in a direction substantially perpendicular to an optical axis of the image guide; and
    a second driving means arranged at the proximal end of insertion section for causing a second vibrating movement of the optical image projected from the exit end of image guide and the eyepiece lens system relative to each other over said predetermined distance in the same direction as that of said first vibrating movement viewed on the optical image in synchronism with said first vibrating movement.

2. An endoscope apparatus according to claim 1, wherein said piezo-electric vibrating element is formed by a piezo-electric bimorph having a resilient metal plate and piezo-electric ceramic layers applied on both surfaces of the metal plate.

3. An endoscope apparatus according to claim 1, wherein said piezo-electric vibrating element is formed by a laminated type piezo-electric element.

4. An endoscope apparatus according to claim 1, wherein one end of said piezo-electric vibrating element is secured to the entrance end of image guide and the other end is secured to a hard member constituting the distal end of insertion section so that the entrance end of image guide is vibrated.

5. An endoscope apparatus according to claim 1, wherein one end of said piezo-electric vibrating element is secured to at least a part of the objective lens system and the other end is secured to a hard member constituting the distal end of insertion section.

6. An endoscope apparatus according to claim 2, wherein said bimorph is arranged in a plane passing through a center axis of the insertion section and has a width which is slightly smaller than a diameter of the insertion section.

7. An endoscope apparatus according to claim 1, wherein said second driving means comprises at least one piezo-electric vibrating element which extends in the longitudinal direction of the insertion section.

8. An endoscope apparatus according to claim 7, wherein said piezo-electric element of the second driving means is formed by a piezo electric bimorph having a resilient metal plate and piezo-electric ceramic layers applied on both surfaces of the resilient metal plate.

9. An endoscope apparatus according to claim 8, wherein one end of said piezo-electric vibrating element is secured to the exit end of image guide and the other end is secured to a hard member constituting the proximal end of insertion section so that the exit end of image guide is vibrated.

10. An endoscope apparatus according to claim 8, wherein one end of said piezo-electric vibrating element is secured to at least a part of the eyepiece lens system and the other end is secured to a hard member constituting the proximal end of insertion section.

11. An endoscope apparatus according to claim 1, wherein said first driving means comprises a first piezo-electric vibrating element for moving at least one of the entrance end of image guide and a part of the objective lens system in a first direction and a second piezo-electric vibrating element for moving at least one of the entrance end of image guide and a part of the objective lens system in a second direction, said first and second directions being substantially perpendicular to the optical axis and said second driving means comprises a first piezo-electric vibrating element for moving at least one of the exit end of image guide and a part of the eyepiece lens system in a first direction and a second piezo-electric vibrating element for moving at least one of the exit end of image guide and a part of the eyepiece lens system in a second direction, said first and second directions being substantially perpendicular to the optical axis.

12. An endoscope apparatus according to claim 11, wherein said first and second directions are set to the same direction.

13. An endoscope apparatus according to claim 11, wherein said first and second directions are set to opposite directions to each other.

14. An endoscope apparatus according to claim 11, wherein said first and second directions are set to be perpendicular to each other.

15. An endoscope apparatus according to claim 11, wherein each of said first and second driving means further comprises an intermediate member and said first piezo-electric vibrating element is arranged between the image guide and the intermediate member and said second piezo-electric vibrating element is arranged between the intermediate member and a hard member.

16. An endoscope apparatus according to claim 7, wherein said piezo-electric vibrating elements of the first and second driving means are vibrated to such an amount that the first and second vibrating movements having an amount of displacement at least equal to a twice of a pitch of optical fiber arrangement of the image guide.

17. An endoscope apparatus according to claim 7, further comprising a driving signal source which applies driving voltages to said piezo-electric elements of the first and second driving means.

18. An endoscope apparatus according to claim 17, wherein said driving voltages have a repetition frequency lower than the maximum audible frequency.

19. An endoscope apparatus according to claim 17, wherein said driving signal source applies the same driving voltage commonly to said first and second piezo-electric vibrating elements.

20. An endoscope apparatus according to claim 17, wherein the apparatus further comprises a light source unit having a lamp for illuminating the object through a light guide inserted within the insertion section and an insulating transformer for energizing the lamp, and said driving signal source is energized by means of said insulating transformer.

21. An endoscope apparatus according to claim 20, wherein said driving voltage is directly derived from a secondary coil of said insulating transformer.

22. An endoscope apparatus according to claim 17, wherein the apparatus further comprises an operation section for handling the insertion section and said driving signal source is arranged within said insertion section.

23. An endoscope apparatus according to claim 4, wherein said entrance end of image guide is freely inserted into a hole formed in the hard member constituting the distal end of insertion section, an opening of the hole is closed by a lid-like member through which the entrance end of image guide is extended into said hole, and said one end of said bimorph is secured to the entrance end of image guide and the other end is fixed to said lid-like member.

24. An endoscope apparatus according to claim 4, wherein said bimorph is wingably supported by a fulcrum provided on one of the entrance end of image guide and the hard member, said one end of the bimorph is secured to the image guide at a position which is far from the entrance end thereof with respect to the fulcrum and the other end is secured to the hard member, whereby a distance between the entrance end of image guide and the fulcrum is longer than a distance between the fulcrum and the position on the image guide at which the one end of bimorph is secured.

25. An endoscope apparatus according to 1, wherein the apparatus further comprises a hard member constituting the distal end of insertion section and an insulating member inserted between the hard member and the piezo-electric vibrating element.

26. An endoscope apparatus according to claim 5, wherein said objective lens system comprises a plurality of lens elements and said piezo-electric vibrating element is coupled with one or more lens elements which serve to move the optical image formed by the objective lens system to the most efficient manner.

27. An endoscope apparatus according to claim 5, wherein said objective lens system comprises a plurality of lens elements including a focus adjusting lens element and said piezo-electric vibrating element is secured to said focus adjusting lens element.

28. An endoscope apparatus according to claim 2, wherein both ends of said bimorph are free from the piezo-electric ceramic layers.

29. An endoscope apparatus according to claim 2, wherein both ends of said bimorph have resilient layers applied thereon.

30. An endoscope apparatus according to claim 1, wherein each of said first and second driving means further comprises a member for limiting an amount of the vibrating movement.

31. An endoscope apparatus according to claim 17, wherein the apparatus further comprises vibration sensors for detecting the first and second vibration movements to derive vibration signals and said vibrating signal source is controlled in accordance with said vibration signals such that the vibration movements of said first and second vibrating means are synchronized with each other.

32. An endoscope apparatus according to claim 17, wherein the apparatus further comprises gain control circuits each inserted in conductors connected between the driving signal source and respective piezo-electric vibrating elements.

33. An endoscope apparatus according to claim 18, wherein the apparatus further comprises a detection circuit for detecting the condition that a television camera attachment is fixed to the endoscope apparatus to device a camera detection signal and said driving signal source is activated when the camera detection signal is generated.

34. An endoscope apparatus according to claim 18, wherein the apparatus further comprises a switch for activating said driving signal source such that the driving signal is generated as long as the switch is closed.

35. An endoscope apparatus according to claim 9, wherein the apparatus further comprises a mask for restricting a field of view of the image guide, said mask being arranged opposite to the exit end of image guide and fixed to a member which is not vibrated.

36. An endoscope apparatus according to claim 9, wherein the apparatus further comprises means for adjusting the position of the exit end of image guide with respect to the eyepiece lens system and including a holding frame arranged around the exit end of image guide, a fitting frame arranged movably within a space between the holding frame and the exit end of image guide, and means for fixing the fitting frame to the holding frame at an adjusted position with respect to the exit end of image guide, whereby said other end of the bimorph is secured to said fitting frame.

* * * * *